United States Patent [19]

Smart et al.

[11] Patent Number: 5,707,810
[45] Date of Patent: Jan. 13, 1998

[54] METHOD OF DIAGNOSING RENAL TISSUE DAMAGE OR DISEASE

[75] Inventors: John E. Smart, Weston; Hermann Oppermann, Medway; Engin Ozkaynak, Milford; Thangavel Kuberasampath, Medway; David C. Rueger, Hopkinton, all of Mass.; Roy H. L. Pang, Etna, N.H.; Charles M. Cohen, Medway, Mass.

[73] Assignee: Creative BioMolecules, Inc., Hopkinton, Mass.

[21] Appl. No.: 643,563

[22] Filed: May 6, 1996

Related U.S. Application Data

[63] Continuation of Ser. No. 278,729, Jul. 20, 1994, Pat. No. 5,650,276, which is a continuation of Ser. No. 938,021, Aug. 28, 1992, which is a continuation-in-part of Ser. No. 752,861, Aug. 30, 1991, abandoned, which is a continuation-in-part of Ser. No. 667,274, Mar. 11, 1991, abandoned.

[51] Int. Cl.$^6$ .................................................. C12Q 1/68
[52] U.S. Cl. ................................................ 435/6; 435/7.21
[58] Field of Search ......................................... 435/6, 7.21

[56] References Cited

U.S. PATENT DOCUMENTS

| | | | |
|---|---|---|---|
| 4,968,590 | 11/1990 | Kuberasampath et al. | 530/326 |
| 4,980,281 | 12/1990 | Housey et al. | 435/29 |
| 5,011,691 | 4/1991 | Oppermann et al. | 424/423 |

FOREIGN PATENT DOCUMENTS

| | | |
|---|---|---|
| WO89/09787 | 10/1989 | WIPO . |
| WO89/09788 | 10/1989 | WIPO . |
| WO90/00619 | 1/1990 | WIPO . |
| WO91/02744 | 3/1991 | WIPO . |

OTHER PUBLICATIONS

Huggins, MD. (1931), "The Formation of Bone Under the Influence of Epithelium of the Urinary Tract," 22 *Arch. Surgery* 377–408.

Urist (1965), "Bone: Formation by Autoinduction," 150 *Science* 893–899.

Needleman et al. (1970), "A General Method Applicable to the Search for Similarities in the Amino Acid Sequence of Two Proteins," 48 *J. Mol. Biol.*, 443–453.

Reddi et al. (1972), "Biochemical Sequences in the Transformation of Normal Fibroblasts in Adolescent Rats," 69 *Pro. Natl. Acad. Sci. USA*, 1601–1605.

Dayhoff et al. (1978), "A Model of Evolutionary Change in Proteins," 5 *Atlas of Protein Sequence and Structure*, 345–352.

Reddi (1981), "Cell Biology and Biochemistry of Endochondral Bone Development," 1 *Coll. Res.*, 209–226.

Sampath et al. (1983), "Homology of Bone-Inductive Proteins from Human, Monkey, Bovine, and Rat Extracellular Matrix," 60 *Proc. Natl. Acad. Sci. USA*, 6591–6595.

Von Heijne (1986), "A New Method for Predicting Signal Sequence Cleavage Sites," 14 *Nucleic Acids Research*, 4683–4690.

Chomczynski et al. (1987), "Single-Step Method of RNA Isolation by Acid Guanidinium Thiocyanate-Phenol-Chloroform Extraction", 162 *Anal. Biochem*, 156–159.

Miller et al. (1987), "Phenotypic Modulation of the Swarm Rat Chondrosarcoma Induced by Morphogenetic Bone Matrix," 42 *Cancer Research*, 3589–3594.

Padgett et al. (1987), "A Transcript from a Drosophila Pattern Gene Predicts a Protein Homologous to the Transforming Growth Factor-β Family," 325 *Nature*, 81–84.

Weeks et al. (1987), "A Maternal MRNA Localizd to the Vegetal Hemisphere in Xenopus Eggs Codes for a Growth Factor Related to TGF-β," 5 *Cell*, 861–867.

Rosen et al., Wang et al. and Wozney et al., (1988) 42 *Calcified Tissue Int.* (Suppl.):A35 (Abstr. No. 136), A37 (Abstr. Nos. 146, 147).

Wang et al., (1988), "Purification and Characterization of Other Distinct Bone–Inducing Factors," 85 *Proc. Natl. Acad. Sci. USA*, 9484–9488.

Wozney et al. (1988), "Novel Regulators of Bone Formation: Molecular Clones and Activities," 242 *Science*, 1528–1534.

Boyd (1989), "Examination of the Effects of Epidermal Growth Factor on the Production of Urokinase and the Expression of the Plasminogen Activator Receptor in a Human Colon Cancer Cell Line,"49 *Cancer Research*, 2427–2432.

Lyons et al. (1989), "VGR-1, A Mammalian Gene Related to Xenopus VG-1, is a Member of the Transforming Growth Factor β Gene Superfamily," 86 *Proc. Natl. Acad. Sci. USA* 4554–4558.

Rosen et al. (1989), "Purification and Molecular Cloning of a Novel Group of BMPS and Localization of BMP MRNA in Developing Bone," 20 *Connective Tissue Research*, 313–319.

Wozney (1989), "Bone Morphogenetic Proteins,"1 *Progress in Growth Factor Research*, 267–280.

Celeste et al. (1990), "Identification of Transforming Growth Factor β Family Members Present in Bone–Inductive Protein Purified from Bovine Bone,"87 *Proc. Natl. Acad. Sci. USA*, 9843–9847.

Katagiri et al. (1990), "The Non–Osteogenic Mouse Pluripotent Cell Line, C3H10T1/2, is Induced to Differentiate into Osteoblastic Cells By Recombinant Human Bone Morphogenetic Protein-2," 172 *Biochemical and Biophysical Research Communications*, 295–299.

(List continued on next page.)

*Primary Examiner*—James Ketter
*Attorney, Agent, or Firm*—Testa, Hurwitz & Thibeault, LLP

[57] ABSTRACT

In one aspect, the present invention provides a method of diagnosing renal tissue damage or disease by measuring endogenous expression of OP-1 by renal tissue of a mammal (e.g., a human) in which a depression of endogenous expression relative to undamaged or undiseased mammalian renal tissue indicates a diagnosis that the mammal is afflicted with renal tissue damage or disease. Also disclosed are methods of diagnosing renal tissue damage or disease in a mammal. The methods involve detecting and/or measuring the expression of the OP-1 (BMP-7) gene or protein in the mammal. Depression of OP-1 expression may be used to diagnose renal tissue damage or disease.

27 Claims, 3 Drawing Sheets

OTHER PUBLICATIONS

Ozkaynak et al. (1990), "OP-1 CDNA Encodes an Osteogenic Protein in the TGF-β Family," 9 *The EMBO Journal*, 2085–2093.

Panganiban et al. (1990), "Biochemical Characterization of the *Drosophila dpp* Protein, a Member of the Transforming Growth Factor β Family of Growth Factors," 10 *Molecular and Cellular Biology*, 2669–2677.

Rosen et al. (1990), "An Alternative Method for the Visualization of RNA in Formaldehyde Agarose Gels," 12 *Focus*, 23–24.

Rosen et al., Celeste et al. (1990), *J. Cell. Biochem.*, Supplement 14E 33 (Abstr. No. 004), 54 (Abstr. No. 105).

Sampath, et al. (1990), "Bovine Osteogenic Protein Is Composed of Dimers of OP-1 and BMP-2A, Two Members of the Transforming Growth Factor–β Superfamily," 265 *J. Biol. Chem.*, 13198–13205.

Wang et al. (1990), "Recombinant Human Bone Morphogenetic Protein Induces Bone Formation," 87 *Proc. Natl. Acad. Sci. USA*, 2220–2324.

Wozney et al. (1990), "Growth Factors Influencing Bone Development," *J. Cell Sci.*, Suppl. 13, 149–156.

D'Allessandro et al. (1991), "Wound Repair," *J. Cell. Biochem.*, 166 (Abstr. No. Q105).

Israel et al. (1991), "Wound Repair," *J. Cell. Biochem.*, 168 (Abstr. No. Q111).

Lee (1991), "Expression of Growth/Differentiation Factor 1 in the Nervous System: Conservation of a Bicistronic Structure," 88 *Proc. Natl. Acad. Sci. USA*, 4250–4254.

Ozkaynak et al. (1991), "Murine Osteogenic Protein (OP-1): High Levels of MRNA in Kidney," 179 *Biochemical and Biophysical Research Communications*, 116–123.

Takuwa et al. (1991), "Bone Morphogenetic Protein–2 Stimulates Alkaline Phosphatase Activity and Collagen Synthesis in Cultured Osteoblastic Cells, MC3T3-E1," 174 *Biochem. Biophys. Res. Comm.*, 96–101.

Wharton et al. (1991), "Drosophila 60A Gene, Another Transforming Growth Factor β Family Member, is Closely Related to Human Bone Morphogenetic Proteins," 88 *Proc. Natl. Acad. Sci. USA*, 9214–9218.

Yamaguchi et al. (1991), "Recombinant Human Bone Morphogenetic Protein–2Stimulates Osteoblastic Maturation and Inhibits Myogenic Differentiation in Vitro," 113 *J. Cell Biol.*, 681–687.

Zhou et al. (1991) "Retinoic Acid Modulation of mRNA Levels in Malignant, Nontransformed, and Immortalized Osteoblasts," 6 *J. Bone & Min. Res.* 7:767–777.

Israel et al. (1992), "Expression and Characterization of Bone Morphogenetic Protein–2 in Chinese Hamster Ovary Cells," 7 *Growth Factors*, 139–150.

Rogers et al. (1992), "Bone Morphogenetic Proteins–2 and –4 are Involved in the Retinoic Acid–Induced Differentiation of Embryonal Carcinoma Cells," 3 *Mol. Biol. Cell*, 189–196.

Rosen et al., Celeste et al., Wozney et al. (1992), "Growth and Differentiation Factors in Vertebrate Development," *J. Cell. Biochem.*, Suppl. 18F, 103(Abstr. No. W513), 100(Abstr. No. W502), 76(Abstr. No. W026).

Thies et al. (1992), "Recombinant Human Bone Morphogenetic Protein–2 Induces Osteoblastic Differentiation in W–20–17 Stromal Cells," 130 *Endocrinol.*, 1318–1324.

Wozney (1992), "The Bone Morphogenetic Protein Family and Osteogenesis," 32 *Molecular Reproduction and Development*, 160–167.

Padgett et al. (1993), "Human BMP Sequences Can Confer Normal Dorsal–Ventral Patterning in the *Drosophila Embryo*," 90 *Proc. Natl. Acad. Sci. USA*, 2905–2909.

Piqueras et al. (1993), "Localization of Osteogenic Protein–1 (OP-1) mRNA and Protein Expression in Kidney," 4 *J. Amer. Soc. Nephrol.* 3:700(A).

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..97
        ( D ) OTHER INFORMATION: /label=GENERIC-SEQ-1
        / note= "EACH XAA INDICATES ONE OF THE 20 NATURALLY
        OCCURRING L- ISOMER, ALPHA-AMINO ACIDS, OR A
        DERIVATIVE THEREOF"

( x i ) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
 1               5                   10                  15
Xaa Xaa Xaa Xaa Xaa Xaa Xaa Xaa Cys Xaa Xaa Xaa Cys Xaa Xaa Xaa
                20                  25                  30
Xaa Xaa Xaa Xaa Xaa Xaa Xaa Xaa Xaa Xaa Xaa Xaa Xaa Xaa Xaa Xaa
            35                  40                  45
Xaa Xaa Xaa Xaa Xaa Xaa Xaa Xaa Xaa Xaa Xaa Xaa Cys Cys Xaa Xaa
     50                      55                  60
Xaa Xaa Xaa Xaa Xaa Xaa Xaa Xaa Xaa Xaa Xaa Xaa Xaa Xaa Xaa Xaa
65                      70                  75                  80
Xaa Xaa Xaa Xaa Xaa Xaa Xaa Xaa Xaa Xaa Xaa Xaa Xaa Cys Xaa Cys
                85                  90                  95
Xaa
```

( 2 ) INFORMATION FOR SEQ ID NO:2:

( i ) SEQUENCE CHARACTERISTICS:
        ( A ) LENGTH: 97 amino acids
        ( B ) TYPE: amino acid (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label=GENERIC-SEQ-2
            / note= "EACH XAA INDICATES ONE OF THE 20 NATURALLY
            OCCURING L- ISOMER, ALPHA-AMINO ACIDS, OR A
            DERIVATIVE THEREOF"

(xi) SEQUENCE DESCRIPTION: SEQ ID NO:2:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Cys Xaa Cys
            85                  90                  95

Xaa (2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label=GENERIC-SEQ-3
            / note= "WHEREIN EACH XAA IS INDEPENDENTLY SELECTED FROM
            A GROUP OF ONE OR MORE SPECIFIED AMINO ACIDS AS DEFINED
            IN THE SPECIFICATION"

(xi) SEQUENCE DESCRIPTION: SEQ ID NO:3:

Leu Tyr Val Xaa Phe Xaa Xaa Xaa Gly Trp Xaa Xaa Trp Xaa Xaa Ala
1               5                   10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Leu
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65              70                  75                  80

Val Xaa Leu Xaa Xaa Xaa Xaa Xaa Met Xaa Val Xaa Xaa Cys Gly Cys
            85                  90                  95

Xaa (2) INFORMATION FOR SEQ ID NO:4:

(i) SEQUENCE CHARACTERISTICS:

(A) LENGTH: 102 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..102
(D) OTHER INFORMATION: /label=GENERIC-SEQ-4
/ note= "WHEREIN EACH XAA IS INDEPENDENTLY SELECTED FROM A GROUP OF ONE OR MORE SPECIFIED AMINO ACIDS AS DEFINED IN THE SPECIFICATION"

(xi) SEQUENCE DESCRIPTION: SEQ ID NO:4:

```
Cys Xaa Xaa Xaa Xaa Leu Tyr Val Xaa Phe Xaa Xaa Xaa Gly Trp Xaa
 1               5                  10                      15
Xaa Trp Xaa Xaa Ala Pro Xaa Gly Xaa Xaa Ala Xaa Tyr Cys Xaa Gly
             20              25                      30
Xaa Cys Xaa Xaa Pro Xaa Xaa Xaa Xaa Xaa Xaa Xaa Xaa Asn His Ala
         35              40                      45
Xaa Xaa Xaa Xaa Leu Xaa Xaa Xaa Xaa Xaa Xaa Xaa Xaa Xaa Xaa Xaa
     50              55                      60
Xaa Cys Cys Xaa Pro Xaa Xaa Xaa Xaa Xaa Xaa Xaa Xaa Leu Xaa Xaa
 65              70                      75                   80
Xaa Xaa Xaa Xaa Xaa Val Xaa Leu Xaa Xaa Xaa Xaa Xaa Met Xaa Val
                 85              90                      95
Xaa Xaa Cys Gly Cys Xaa
             100
```

(2) INFORMATION FOR SEQ ID NO:5:

(i) SEQUENCE CHARACTERISTICS:
(A) LENGTH: 139 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..139
(D) OTHER INFORMATION: /note= "HOP-1 (MATURE FORM)"

(xi) SEQUENCE DESCRIPTION: SEQ ID NO:5:

```
Ser Thr Gly Ser Lys Gln Arg Ser Gln Asn Arg Ser Lys Thr Pro Lys
 1               5                  10                      15
Asn Gln Glu Ala Leu Arg Met Ala Asn Val Ala Glu Asn Ser Ser Ser
             20              25                      30
Asp Gln Arg Gln Ala Cys Lys Lys His Glu Leu Tyr Val Ser Phe Arg
         35              40                      45
Asp Leu Gly Trp Gln Asp Trp Ile Ile Ala Pro Glu Gly Tyr Ala Ala
     50              55                      60
Tyr Tyr Cys Glu Gly Glu Cys Ala Phe Pro Leu Asn Ser Tyr Met Asn
 65              70                      75                   80
Ala Thr Asn His Ala Ile Val Gln Thr Leu Val His Phe Ile Asn Pro
                 85              90                      95
Glu Thr Val Pro Lys Pro Cys Cys Ala Pro Thr Gln Leu Asn Ala Ile
                 100             105                     110
Ser Val Leu Tyr Phe Asp Asp Ser Ser Asn Val Ile Leu Lys Lys Tyr
             115             120                     125
```

```
              Arg  Asn  Met  Val  Val  Arg  Ala  Cys  Gly  Cys  His
                   130                 135
```

( 2 ) INFORMATION FOR SEQ ID NO:6:

( i ) SEQUENCE CHARACTERISTICS:
      ( A ) LENGTH: 139 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..139
      ( D ) OTHER INFORMATION: /note= "MOP-1 (MATURE FORM)"

( x i ) SEQUENCE DESCRIPTION: SEQ ID NO:6:

```
Ser  Thr  Gly  Gly  Lys  Gln  Arg  Ser  Gln  Asn  Arg  Ser  Lys  Thr  Pro  Lys
  1              5                  10                 15

Asn  Gln  Glu  Ala  Leu  Arg  Met  Ala  Ser  Val  Ala  Glu  Asn  Ser  Ser  Ser
              20                  25                 30

Asp  Gln  Arg  Gln  Ala  Cys  Lys  Lys  His  Glu  Leu  Tyr  Val  Ser  Phe  Arg
         35                  40                 45

Asp  Leu  Gly  Trp  Gln  Asp  Trp  Ile  Ile  Ala  Pro  Glu  Gly  Tyr  Ala  Ala
         50                  55                 60

Tyr  Tyr  Cys  Glu  Gly  Glu  Cys  Ala  Phe  Pro  Leu  Asn  Ser  Tyr  Met  Asn
 65                  70                 75                            80

Ala  Thr  Asn  His  Ala  Ile  Val  Gln  Thr  Leu  Val  His  Phe  Ile  Asn  Pro
                   85                  90                     95

Asp  Thr  Val  Pro  Lys  Pro  Cys  Cys  Ala  Pro  Thr  Gln  Leu  Asn  Ala  Ile
              100                 105                110

Ser  Val  Leu  Tyr  Phe  Asp  Asp  Ser  Ser  Asn  Val  Ile  Leu  Lys  Lys  Tyr
         115                 120                125

Arg  Asn  Met  Val  Val  Arg  Ala  Cys  Gly  Cys  His
         130                 135
```

( 2 ) INFORMATION FOR SEQ ID NO:7:

( i ) SEQUENCE CHARACTERISTICS:
      ( A ) LENGTH: 139 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..139
      ( D ) OTHER INFORMATION: /note= "HOP-2 (MATURE FORM)"

( x i ) SEQUENCE DESCRIPTION: SEQ ID NO:7:

```
Ala  Val  Arg  Pro  Leu  Arg  Arg  Arg  Gln  Pro  Lys  Lys  Ser  Asn  Glu  Leu
  1              5                  10                 15

Pro  Gln  Ala  Asn  Arg  Leu  Pro  Gly  Ile  Phe  Asp  Asp  Val  His  Gly  Ser
              20                  25                 30

His  Gly  Arg  Gln  Val  Cys  Arg  Arg  His  Glu  Leu  Tyr  Val  Ser  Phe  Gln
         35                  40                 45

Asp  Leu  Gly  Trp  Leu  Asp  Trp  Val  Ile  Ala  Pro  Gln  Gly  Tyr  Ser  Ala
         50                  55                 60

Tyr  Tyr  Cys  Glu  Gly  Glu  Cys  Ser  Phe  Pro  Leu  Asp  Ser  Cys  Met  Asn
 65                  70                 75                            80
```

```
Ala  Thr  Asn  His  Ala  Ile  Leu  Gln  Ser  Leu  Val  His  Leu  Met  Lys  Pro
                    85                      90                      95

Asn  Ala  Val  Pro  Lys  Ala  Cys  Cys  Ala  Pro  Thr  Lys  Leu  Ser  Ala  Thr
               100                      105                      110

Ser  Val  Leu  Tyr  Tyr  Asp  Ser  Ser  Asn  Asn  Val  Ile  Leu  Arg  Lys  His
               115                      120                      125

Arg  Asn  Met  Val  Val  Lys  Ala  Cys  Gly  Cys  His
     130                      135
```

( 2 ) INFORMATION FOR SEQ ID NO:8:

( i ) SEQUENCE CHARACTERISTICS:
        ( A ) LENGTH: 139 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..139
        ( D ) OTHER INFORMATION: /note= "MOP-2 (MATURE FORM)"

( x i ) SEQUENCE DESCRIPTION: SEQ ID NO:8:

```
Ala  Ala  Arg  Pro  Leu  Lys  Arg  Arg  Gln  Pro  Lys  Lys  Thr  Asn  Glu  Leu
1                    5                      10                      15

Pro  His  Pro  Asn  Lys  Leu  Pro  Gly  Ile  Phe  Asp  Asp  Gly  His  Gly  Ser
               20                      25                      30

Arg  Gly  Arg  Glu  Val  Cys  Arg  Arg  His  Glu  Leu  Tyr  Val  Ser  Phe  Arg
               35                      40                      45

Asp  Leu  Gly  Trp  Leu  Asp  Trp  Val  Ile  Ala  Pro  Gln  Gly  Tyr  Ser  Ala
     50                      55                      60

Tyr  Tyr  Cys  Glu  Gly  Glu  Cys  Ala  Phe  Pro  Leu  Asp  Ser  Cys  Met  Asn
65                        70                      75                       80

Ala  Thr  Asn  His  Ala  Ile  Leu  Gln  Ser  Leu  Val  His  Leu  Met  Lys  Pro
                    85                      90                      95

Asp  Val  Val  Pro  Lys  Ala  Cys  Cys  Ala  Pro  Thr  Lys  Leu  Ser  Ala  Thr
               100                      105                      110

Ser  Val  Leu  Tyr  Tyr  Asp  Ser  Ser  Asn  Asn  Val  Ile  Leu  Arg  Lys  His
               115                      120                      125

Arg  Asn  Met  Val  Val  Lys  Ala  Cys  Gly  Cys  His
     130                      135
```

( 2 ) INFORMATION FOR SEQ ID NO:9:

( i ) SEQUENCE CHARACTERISTICS:
        ( A ) LENGTH: 101 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..101
        ( D ) OTHER INFORMATION: /note= "CBMP-2A(FX)"

( x i ) SEQUENCE DESCRIPTION: SEQ ID NO:9:

```
Cys  Lys  Arg  His  Pro  Leu  Tyr  Val  Asp  Phe  Ser  Asp  Val  Gly  Trp  Asn
1                    5                      10                      15

Asp  Trp  Ile  Val  Ala  Pro  Pro  Gly  Tyr  His  Ala  Phe  Tyr  Cys  His  Gly
```

20                          25                              30

Glu Cys Pro Phe Pro Leu Ala Asp His Leu Asn Ser Thr Asn His Ala
                35                      40                      45

Ile Val Gln Thr Leu Val Asn Ser Val Asn Ser Lys Ile Pro Lys Ala
                50                      55                      60

Cys Cys Val Pro Thr Glu Leu Ser Ala Ile Ser Met Leu Tyr Leu Asp
        65                      70                      75                      80

Glu Asn Glu Lys Val Val Leu Lys Asn Tyr Gln Asp Met Val Val Glu
                        85                      90                      95

Gly Cys Gly Cys Arg
                    100

( 2 ) INFORMATION FOR SEQ ID NO:10:

( i ) SEQUENCE CHARACTERISTICS:
        ( A ) LENGTH: 101 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..101
        ( D ) OTHER INFORMATION: /note= "CBMP-2B(FX)"

( x i ) SEQUENCE DESCRIPTION: SEQ ID NO:10:

```
Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                      45

Ile Val Gln Thr Leu Val Asn Ser Val Asn Ser Ser Ile Pro Lys Ala
    50                      55                  60

Cys Cys Val Pro Thr Glu Leu Ser Ala Ile Ser Met Leu Tyr Leu Asp
65                  70                      75                  80

Glu Tyr Asp Lys Val Val Leu Lys Asn Tyr Gln Glu Met Val Val Glu
                85                      90                  95

Gly Cys Gly Cys Arg
            100
```

( 2 ) INFORMATION FOR SEQ ID NO:11:

( i ) SEQUENCE CHARACTERISTICS:
( A ) LENGTH: 102 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..102
( D ) OTHER INFORMATION: /note= "DPP(FX)"

( x i ) SEQUENCE DESCRIPTION: SEQ ID NO:11:

```
Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
            20                  25                  30
```

```
        Lys  Cys  Pro  Phe  Pro  Leu  Ala  Asp  His  Phe  Asn  Ser  Thr  Asn  His  Ala
                  35                       40                  45

Val  Val  Gln  Thr  Leu  Val  Asn  Asn  Asn  Pro  Gly  Lys  Val  Pro  Lys
        50                            55                  60

Ala  Cys  Cys  Val  Pro  Thr  Gln  Leu  Asp  Ser  Val  Ala  Met  Leu  Tyr  Leu
        65                       70                       75                       80

Asn  Asp  Gln  Ser  Thr  Val  Val  Leu  Lys  Asn  Tyr  Gln  Glu  Met  Thr  Val
                            85                  90                            95

Val  Gly  Cys  Gly  Cys  Arg
                            100
```

( 2 ) INFORMATION FOR SEQ ID NO:12:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..102
      ( D ) OTHER INFORMATION: /note= "VGL(FX)"

( x i ) SEQUENCE DESCRIPTION: SEQ ID NO:12:

```
        Cys  Lys  Lys  Arg  His  Leu  Tyr  Val  Glu  Phe  Lys  Asp  Val  Gly  Trp  Gln
        1                       5                       10                      15

Asn  Trp  Val  Ile  Ala  Pro  Gln  Gly  Tyr  Met  Ala  Asn  Tyr  Cys  Tyr  Gly
                            20                  25                       30

Glu  Cys  Pro  Tyr  Pro  Leu  Thr  Glu  Ile  Leu  Asn  Gly  Ser  Asn  His  Ala
                  35                       40                       45

Ile  Leu  Gln  Thr  Leu  Val  His  Ser  Ile  Glu  Pro  Glu  Asp  Ile  Pro  Leu
        50                            55                  60

Pro  Cys  Cys  Val  Pro  Thr  Lys  Met  Ser  Pro  Ile  Ser  Met  Leu  Phe  Tyr
        65                       70                       75                       80

Asp  Asn  Asn  Asp  Asn  Val  Val  Leu  Arg  His  Tyr  Glu  Asn  Met  Ala  Val
                            85                  90                            95

Asp  Glu  Cys  Gly  Cys  Arg
                            100
```

( 2 ) INFORMATION FOR SEQ ID NO:13:

( i ) SEQUENCE CHARACTERISTICS:
      ( A ) LENGTH: 102 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Protein
      ( B ) LOCATION: 1..102
      ( D ) OTHER INFORMATION: /note= "VGR-1(FX)"

( x i ) SEQUENCE DESCRIPTION: SEQ ID NO:13:

```
        Cys  Lys  Lys  His  Glu  Leu  Tyr  Val  Ser  Phe  Gln  Asp  Val  Gly  Trp  Gln
        1                       5                       10                      15

Asp  Trp  Ile  Ile  Ala  Pro  Lys  Gly  Tyr  Ala  Ala  Asn  Tyr  Cys  Asp  Gly
                            20                  25                       30

Glu  Cys  Ser  Phe  Pro  Leu  Asn  Ala  His  Met  Asn  Ala  Thr  Asn  His  Ala
                  35                       40                       45
```

```
         Ile  Val  Gln  Thr  Leu  Val  His  Val  Met  Asn  Pro  Glu  Tyr  Val  Pro  Lys
               50                       55                  60

Pro  Cys  Cys  Ala  Pro  Thr  Lys  Val  Asn  Ala  Ile  Ser  Val  Leu  Tyr  Phe
          65                  70                       75                            80

Asp  Asp  Asn  Ser  Asn  Val  Ile  Leu  Lys  Lys  Tyr  Arg  Asn  Met  Val  Val
                             85                       90                       95

Arg  Ala  Cys  Gly  Cys  His
                         100
```

( 2 ) INFORMATION FOR SEQ ID NO:14:

( i ) SEQUENCE CHARACTERISTICS:
        ( A ) LENGTH: 106 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..106
        ( D ) OTHER INFORMATION: /note= "GDF-1 (FX)"

( x i ) SEQUENCE DESCRIPTION: SEQ ID NO:14:

```
         Cys  Arg  Ala  Arg  Arg  Leu  Tyr  Val  Ser  Phe  Arg  Glu  Val  Gly  Trp  His
          1              5                        10                            15

Arg  Trp  Val  Ile  Ala  Pro  Arg  Gly  Phe  Leu  Ala  Asn  Tyr  Cys  Gln  Gly
                         20                       25                       30

Gln  Cys  Ala  Leu  Pro  Val  Ala  Leu  Ser  Gly  Ser  Gly  Gly  Pro  Pro  Ala
                    35                       40                       45

Leu  Asn  His  Ala  Val  Leu  Arg  Ala  Leu  Met  His  Ala  Ala  Pro  Gly
               50                       55                       60

Ala  Ala  Asp  Leu  Pro  Cys  Cys  Val  Pro  Ala  Arg  Leu  Ser  Pro  Ile  Ser
          65                  70                       75                            80

Val  Leu  Phe  Phe  Asp  Asn  Ser  Asp  Asn  Val  Val  Leu  Arg  Gln  Tyr  Glu
                             85                       90                       95

Asp  Met  Val  Val  Asp  Glu  Cys  Gly  Cys  Arg
                         100                     105
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
         Cys  Xaa  Xaa  Xaa  Xaa
          1                   5
```

( 2 ) INFORMATION FOR SEQ ID NO:16:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 49..1341
(D) OTHER INFORMATION: /product="HOP-1"

(xi) SEQUENCE DESCRIPTION: SEQ ID NO:16:

| | | | | | | | |
|---|---|---|---|---|---|---|---|
| GGTGCGGGCC CGGAGCCCGG AGCCCGGGTA GCGCGTAGAG CCGGCGCG ATG CAC GTG | | | | | | | 57 |
| | | | | | Met His Val | | |
| | | | | | 1 | | |

| CGC | TCA | CTG | CGA | GCT | GCG | GCG | CCG | CAC | AGC | TTC | GTG | GCG | CTC | TGG | GCA | 105 |
|---|---|---|---|---|---|---|---|---|---|---|---|---|---|---|---|---|
| Arg | Ser | Leu | Arg | Ala | Ala | Ala | Pro | His | Ser | Phe | Val | Ala | Leu | Trp | Ala | |
| | 5 | | | | 10 | | | | | 15 | | | | | | |

| CCC | CTG | TTC | CTG | CTG | CGC | TCC | GCC | CTG | GCC | GAC | TTC | AGC | CTG | GAC | AAC | 153 |
|---|---|---|---|---|---|---|---|---|---|---|---|---|---|---|---|---|
| Pro | Leu | Phe | Leu | Leu | Arg | Ser | Ala | Leu | Ala | Asp | Phe | Ser | Leu | Asp | Asn | |
| 20 | | | | | 25 | | | | | 30 | | | | | 35 | |

| GAG | GTG | CAC | TCG | AGC | TTC | ATC | CAC | CGG | CGC | CTC | CGC | AGC | CAG | GAG | CGG | 201 |
|---|---|---|---|---|---|---|---|---|---|---|---|---|---|---|---|---|
| Glu | Val | His | Ser | Ser | Phe | Ile | His | Arg | Arg | Leu | Arg | Ser | Gln | Glu | Arg | |
| | | | 40 | | | | | 45 | | | | | 50 | | | |

| CGG | GAG | ATG | CAG | CGC | GAG | ATC | CTC | TCC | ATT | TTG | GGC | TTG | CCC | CAC | CGC | 249 |
|---|---|---|---|---|---|---|---|---|---|---|---|---|---|---|---|---|
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |

| CCG | CGC | CCG | CAC | CTC | CAG | GGC | AAG | CAC | AAC | TCG | GCA | CCC | ATG | TTC | ATG | 297 |
|---|---|---|---|---|---|---|---|---|---|---|---|---|---|---|---|---|
| Pro | Arg | Pro | His | Leu | Gln | Gly | Lys | His | Asn | Ser | Ala | Pro | Met | Phe | Met | |
| | 70 | | | | | 75 | | | | | 80 | | | | | |

| CTG | GAC | CTG | TAC | AAC | GCC | ATG | GCG | GTG | GAG | GAG | GGC | GGC | GGG | CCC | GGC | 345 |
|---|---|---|---|---|---|---|---|---|---|---|---|---|---|---|---|---|
| Leu | Asp | Leu | Tyr | Asn | Ala | Met | Ala | Val | Glu | Glu | Gly | Gly | Gly | Pro | Gly | |
| | 85 | | | | | 90 | | | | | 95 | | | | | |

| GGC | CAG | GGC | TTC | TCC | TAC | CCC | TAC | AAG | GCC | GTC | TTC | AGT | ACC | CAG | GGC | 393 |
|---|---|---|---|---|---|---|---|---|---|---|---|---|---|---|---|---|
| Gly | Gln | Gly | Phe | Ser | Tyr | Pro | Tyr | Lys | Ala | Val | Phe | Ser | Thr | Gln | Gly | |
| 100 | | | | | 105 | | | | | 110 | | | | | 115 | |

| CCC | CCT | CTG | GCC | AGC | CTG | CAA | GAT | AGC | CAT | TTC | CTC | ACC | GAC | GCC | GAC | 441 |
|---|---|---|---|---|---|---|---|---|---|---|---|---|---|---|---|---|
| Pro | Pro | Leu | Ala | Ser | Leu | Gln | Asp | Ser | His | Phe | Leu | Thr | Asp | Ala | Asp | |
| | | | | 120 | | | | | 125 | | | | | 130 | | |

| ATG | GTC | ATG | AGC | TTC | GTC | AAC | CTC | GTG | GAA | CAT | GAC | AAG | GAA | TTC | TTC | 489 |
|---|---|---|---|---|---|---|---|---|---|---|---|---|---|---|---|---|
| Met | Val | Met | Ser | Phe | Val | Asn | Leu | Val | Glu | His | Asp | Lys | Glu | Phe | Phe | |
| | | | 135 | | | | | 140 | | | | | 145 | | | |

| CAC | CCA | CGC | TAC | CAC | CAT | CGA | GAG | TTC | CGG | TTT | GAT | CTT | TCC | AAG | ATC | 537 |
|---|---|---|---|---|---|---|---|---|---|---|---|---|---|---|---|---|
| His | Pro | Arg | Tyr | His | His | Arg | Glu | Phe | Arg | Phe | Asp | Leu | Ser | Lys | Ile | |
| | | 150 | | | | | 155 | | | | | 160 | | | | |

| CCA | GAA | GGG | GAA | GCT | GTC | ACG | GCA | GCC | GAA | TTC | CGG | ATC | TAC | AAG | GAC | 585 |
|---|---|---|---|---|---|---|---|---|---|---|---|---|---|---|---|---|
| Pro | Glu | Gly | Glu | Ala | Val | Thr | Ala | Ala | Glu | Phe | Arg | Ile | Tyr | Lys | Asp | |
| | 165 | | | | | 170 | | | | | 175 | | | | | |

| TAC | ATC | CGG | GAA | CGC | TTC | GAC | AAT | GAG | ACG | TTC | CGG | ATC | AGC | GTT | TAT | 633 |
|---|---|---|---|---|---|---|---|---|---|---|---|---|---|---|---|---|
| Tyr | Ile | Arg | Glu | Arg | Phe | Asp | Asn | Glu | Thr | Phe | Arg | Ile | Ser | Val | Tyr | |
| 180 | | | | | 185 | | | | | 190 | | | | | 195 | |

| CAG | GTG | CTC | CAG | GAG | CAC | TTG | GGC | AGG | GAA | TCG | GAT | CTC | TTC | CTG | CTC | 681 |
|---|---|---|---|---|---|---|---|---|---|---|---|---|---|---|---|---|
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |

| GAC | AGC | CGT | ACC | CTC | TGG | GCC | TCG | GAG | GAG | GGC | TGG | CTG | GTG | TTT | GAC | 729 |
|---|---|---|---|---|---|---|---|---|---|---|---|---|---|---|---|---|
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |

| ATC | ACA | GCC | ACC | AGC | AAC | CAC | TGG | GTG | GTC | AAT | CCG | CGG | CAC | AAC | CTG | 777 |
|---|---|---|---|---|---|---|---|---|---|---|---|---|---|---|---|---|
| Ile | Thr | Ala | Thr | Ser | Asn | His | Trp | Val | Val | Asn | Pro | Arg | His | Asn | Leu | |
| | | 230 | | | | | 235 | | | | | 240 | | | | |

| GGC | CTG | CAG | CTC | TCG | GTG | GAG | ACG | CTG | GAT | GGG | CAG | AGC | ATC | AAC | CCC | 825 |
|---|---|---|---|---|---|---|---|---|---|---|---|---|---|---|---|---|
| Gly | Leu | Gln | Leu | Ser | Val | Glu | Thr | Leu | Asp | Gly | Gln | Ser | Ile | Asn | Pro | |
| | 245 | | | | | 250 | | | | | 255 | | | | | |

| AAG | TTG | GCG | GGC | CTG | ATT | GGG | CGG | CAC | GGG | CCC | CAG | AAC | AAG | CAG | CCC | 873 |
|---|---|---|---|---|---|---|---|---|---|---|---|---|---|---|---|---|
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |

| TTC | ATG | GTG | GCT | TTC | TTC | AAG | GCC | ACG | GAG | GTC | CAC | TTC | CGC | AGC | ATC | 921 |
|---|---|---|---|---|---|---|---|---|---|---|---|---|---|---|---|---|
| Phe | Met | Val | Ala | Phe | Phe | Lys | Ala | Thr | Glu | Val | His | Phe | Arg | Ser | Ile | |

-continued

|  |  |  |  |  |  | 280 |  |  |  |  | 285 |  |  |  |  | 290 |  |  |  |
|---|---|---|---|---|---|---|---|---|---|---|---|---|---|---|---|---|---|---|---|

| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro |  |
|     |     |     | 295 |     |     |     |     | 300 |     |     |     |     | 305 |     |     |  |

| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser |  |
|     |     |     | 310 |     |     |     |     | 315 |     |     |     |     | 320 |     |     |  |

| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe |  |
|     | 325 |     |     |     |     | 330 |     |     |     |     | 335 |     |     |     |     |  |

| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala |  |
| 340 |     |     |     |     | 345 |     |     |     |     | 350 |     |     |     |     | 355 |  |

| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met |  |
|     |     |     | 360 |     |     |     |     | 365 |     |     |     |     | 370 |     |     |  |

| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn |  |
|     |     | 375 |     |     |     |     | 380 |     |     |     |     | 385 |     |     |     |  |

| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala |  |
|     |     | 390 |     |     |     |     | 395 |     |     |     |     | 400 |     |     |     |  |

| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys |  |
| 405 |     |     |     |     | 410 |     |     |     |     | 415 |     |     |     |     |     |  |

| TAC | AGA | AAC | ATG | GTG | GTC | CGG | GCC | TGT | GGC | TGC | CAC | TAGCTCCTCC | 1351 |
| Tyr | Arg | Asn | Met | Val | Val | Arg | Ala | Cys | Gly | Cys | His |  |
| 420 |     |     |     | 425 |     |     |     |     | 430 |     |     |  |

| GAGAATTCAG | ACCCTTTGGG | GCCAAGTTTT | TCTGGATCCT | CCATTGCTCG | CCTTGGCCAG | 1411 |
| GAACCAGCAG | ACCAACTGCC | TTTTGTGAGA | CCTTCCCCTC | CCTATCCCCA | ACTTTAAAGG | 1471 |
| TGTGAGAGTA | TTAGGAAACA | TGAGCAGCAT | ATGGCTTTTG | ATCAGTTTTT | CAGTGGCAGC | 1531 |
| ATCCAATGAA | CAAGATCCTA | CAAGCTGTGC | AGGCAAAACC | TAGCAGGAAA | AAAAAACAAC | 1591 |
| GCATAAAGAA | AAATGGCCGG | GCCAGGTCAT | GGCTGGGAA | GTCTCAGCCA | TGCACGGACT | 1651 |
| CGTTTCCAGA | GGTAATTATG | AGCGCCTACC | AGCCAGGCCA | CCCAGCCGTG | GGAGGAAGGG | 1711 |
| GGCGTGGCAA | GGGGTGGGCA | CATTGGTGTC | TGTGCGAAAG | GAAAATTGAC | CCGGAAGTTC | 1771 |
| CTGTAATAAA | TGTCACAATA | AAACGAATGA | ATGAAAAAAA | AAAAAAAAA | A | 1822 |

( 2 ) INFORMATION FOR SEQ ID NO:17:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| Met | His | Val | Arg | Ser | Leu | Arg | Ala | Ala | Ala | Pro | His | Ser | Phe | Val | Ala |
| 1 |  |  |  | 5 |  |  |  |  | 10 |  |  |  |  | 15 |  |

| Leu | Trp | Ala | Pro | Leu | Phe | Leu | Leu | Arg | Ser | Ala | Leu | Ala | Asp | Phe | Ser |
|  |  |  | 20 |  |  |  |  | 25 |  |  |  |  | 30 |  |  |

| Leu | Asp | Asn | Glu | Val | His | Ser | Ser | Phe | Ile | His | Arg | Arg | Leu | Arg | Ser |
|  |  |  | 35 |  |  |  |  | 40 |  |  |  |  | 45 |  |  |

| Gln | Glu | Arg | Arg | Glu | Met | Gln | Arg | Glu | Ile | Leu | Ser | Ile | Leu | Gly | Leu |
|  |  | 50 |  |  |  |  | 55 |  |  |  |  | 60 |  |  |  |

| Pro | His | Arg | Pro | Arg | Pro | His | Leu | Gln | Gly | Lys | His | Asn | Ser | Ala | Pro |
| 65 |  |  |  |  | 70 |  |  |  |  | 75 |  |  |  |  | 80 |

```
Met Phe Met Leu Asp Leu Tyr Asn Ala Met Ala Val Glu Glu Gly Gly
                85                  90                  95
Gly Pro Gly Gly Gln Gly Phe Ser Tyr Pro Tyr Lys Ala Val Phe Ser
            100                 105                 110
Thr Gln Gly Pro Pro Leu Ala Ser Leu Gln Asp Ser His Phe Leu Thr
        115                 120                 125
Asp Ala Asp Met Val Met Ser Phe Val Asn Leu Val Glu His Asp Lys
    130                 135                 140
Glu Phe Phe His Pro Arg Tyr His Arg Glu Phe Arg Phe Asp Leu
145                 150                 155                 160
Ser Lys Ile Pro Glu Gly Glu Ala Val Thr Ala Ala Glu Phe Arg Ile
                165                 170                 175
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
    210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Arg Ser Gln Asn Arg Ser
290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430
```

(2) INFORMATION FOR SEQ ID NO:18:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 104..1393
(D) OTHER INFORMATION: /product="MOP1 (CDNA)"

(xi) SEQUENCE DESCRIPTION: SEQ ID NO:18:

```
CTGCAGCAAG TGACCTCGGG TCGTGGACCG CTGCCCTGCC CCCTCCGCTG CCACCTGGGG      60

CGGCGCGGGC CCGGTGCCCC GGATCGCGCG TAGAGCCGGC GCG ATG CAC GTG CGC       115
                                              Met His Val Arg
                                               1

TCG CTG CGC GCT GCG GCG CCA CAC AGC TTC GTG GCG CTC TGG GCG CCT       163
Ser Leu Arg Ala Ala Ala Pro His Ser Phe Val Ala Leu Trp Ala Pro
 5           10                  15                  20

CTG TTC TTG CTG CGC TCC GCC CTG GCC GAT TTC AGC CTG GAC AAC GAG       211
Leu Phe Leu Leu Arg Ser Ala Leu Ala Asp Phe Ser Leu Asp Asn Glu
            25                  30                  35

GTG CAC TCC AGC TTC ATC CAC CGG CGC CTC CGC AGC CAG GAG CGG CGG       259
Val His Ser Ser Phe Ile His Arg Arg Leu Arg Ser Gln Glu Arg Arg
                40                  45                  50

GAG ATG CAG CGG GAG ATC CTG TCC ATC TTA GGG TTG CCC CAT CGC CCG       307
Glu Met Gln Arg Glu Ile Leu Ser Ile Leu Gly Leu Pro His Arg Pro
         55                  60                  65

CGC CCG CAC CTC CAG GGA AAG CAT AAT TCG GCG CCC ATG TTC ATG TTG       355
Arg Pro His Leu Gln Gly Lys His Asn Ser Ala Pro Met Phe Met Leu
     70                  75                  80

GAC CTG TAC AAC GCC ATG GCG GTG GAG GAG AGC GGG CCG GAC GGA CAG       403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT       451
Gly Phe Ser Tyr Pro Tyr Lys Ala Val Phe Ser Thr Gln Gly Pro Pro
            105                 110                 115

TTA GCC AGC CTG CAG GAC AGC CAT TTC CTC ACT GAC GCC GAC ATG GTC       499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT       547
Met Ser Phe Val Asn Leu Val Glu His Asp Lys Glu Phe Phe His Pro
             135                 140                 145

CGA TAC CAC CAT CGG GAG TTC CGG TTT GAT CTT TCC AAG ATC CCC GAG       595
Arg Tyr His His Arg Glu Phe Arg Phe Asp Leu Ser Lys Ile Pro Glu
 150                 155                 160

GGC GAA CGG GTG ACC GCA GCC GAA TTC AGG ATC TAT AAG GAC TAC ATC       643
Gly Glu Arg Val Thr Ala Ala Glu Phe Arg Ile Tyr Lys Asp Tyr Ile
 165                 170                 175                 180

CGG GAG CGA TTT GAC AAC GAG ACC TTC CAG ATC ACA GTC TAT CAG GTG       691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC       739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA       787
Arg Thr Ile Trp Ala Ser Glu Glu Gly Trp Leu Val Phe Asp Ile Thr
            215                 220                 225

GCC ACC AGC AAC CAC TGG GTG GTC AAC CCT CGG CAC AAC CTG GGC TTA       835
Ala Thr Ser Asn His Trp Val Val Asn Pro Arg His Asn Leu Gly Leu
        230                 235                 240

CAG CTC TCT GTG GAG ACC CTG GAT GGG CAG AGC ATC AAC CCC AAG TTG       883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG       931
Ala Gly Leu Ile Gly Arg His Gly Pro Gln Asn Lys Gln Pro Phe Met
            265                 270                 275

GTG GCC TTC TTC AAG GCC ACG GAA GTC CAT CTC CGT AGT ATC CGG TCC       979
```

|  |  |  |  |  |  |  |  |  |  |  |  |  |  |  |  |
|---|---|---|---|---|---|---|---|---|---|---|---|---|---|---|---|
| Val | Ala | Phe | Phe 280 | Lys | Ala | Thr | Glu 285 | Val | His | Leu | Arg | Ser | Ile 290 | Arg | Ser |

| ACG | GGG | GGC | AAG | CAG | CGC | AGC | CAG | AAT | CGC | TCC | AAG | ACG | CCA | AAG | AAC | 1027 |
|---|---|---|---|---|---|---|---|---|---|---|---|---|---|---|---|---|
| Thr | Gly | Gly 295 | Lys | Gln | Arg | Ser | Gln 300 | Asn | Arg | Ser | Lys | Thr 305 | Pro | Lys | Asn | |

| CAA | GAG | GCC | CTG | AGG | ATG | GCC | AGT | GTG | GCA | GAA | AAC | AGC | AGC | AGT | GAC | 1075 |
|---|---|---|---|---|---|---|---|---|---|---|---|---|---|---|---|---|
| Gln | Glu 310 | Ala | Leu | Arg | Met | Ala 315 | Ser | Val | Ala | Glu | Asn 320 | Ser | Ser | Ser | Asp | |

| CAG | AGG | CAG | GCC | TGC | AAG | AAA | CAT | GAG | CTG | TAC | GTC | AGC | TTC | CGA | GAC | 1123 |
|---|---|---|---|---|---|---|---|---|---|---|---|---|---|---|---|---|
| Gln | Arg 325 | Gln | Ala | Cys | Lys 330 | Lys | His | Glu | Leu | Tyr 335 | Val | Ser | Phe | Arg | Asp 340 | |

| CTT | GGC | TGG | CAG | GAC | TGG | ATC | ATT | GCA | CCT | GAA | GGC | TAT | GCT | GCC | TAC | 1171 |
|---|---|---|---|---|---|---|---|---|---|---|---|---|---|---|---|---|
| Leu | Gly | Trp | Gln | Asp 345 | Trp | Ile | Ile | Ala | Pro 350 | Glu | Gly | Tyr | Ala | Ala 355 | Tyr | |

| TAC | TGT | GAG | GGA | GAG | TGC | GCC | TTC | CCT | CTG | AAC | TCC | TAC | ATG | AAC | GCC | 1219 |
|---|---|---|---|---|---|---|---|---|---|---|---|---|---|---|---|---|
| Tyr | Cys | Glu | Gly 360 | Glu | Cys | Ala | Phe | Pro 365 | Leu | Asn | Ser | Tyr | Met 370 | Asn | Ala | |

| ACC | AAC | CAC | GCC | ATC | GTC | CAG | ACA | CTG | GTT | CAC | TTC | ATC | AAC | CCA | GAC | 1267 |
|---|---|---|---|---|---|---|---|---|---|---|---|---|---|---|---|---|
| Thr | Asn | His | Ala 375 | Ile | Val | Gln | Thr | Leu 380 | Val | His | Phe | Ile | Asn 385 | Pro | Asp | |

| ACA | GTA | CCC | AAG | CCC | TGC | TGT | GCG | CCC | ACC | CAG | CTC | AAC | GCC | ATC | TCT | 1315 |
|---|---|---|---|---|---|---|---|---|---|---|---|---|---|---|---|---|
| Thr | Val 390 | Pro | Lys | Pro | Cys | Cys 395 | Ala | Pro | Thr | Gln | Leu 400 | Asn | Ala | Ile | Ser | |

| GTC | CTC | TAC | TTC | GAC | GAC | AGC | TCT | AAT | GTC | ATC | CTG | AAG | AAG | TAC | AGA | 1363 |
|---|---|---|---|---|---|---|---|---|---|---|---|---|---|---|---|---|
| Val 405 | Leu | Tyr | Phe | Asp | Asp 410 | Ser | Ser | Asn | Val | Ile 415 | Leu | Lys | Lys | Tyr | Arg 420 | |

| AAC | ATG | GTG | GTC | CGG | GCC | TGT | GGC | TGC | CAC | TAGCTCTTCC | TGAGACCCTG | 1413 |
|---|---|---|---|---|---|---|---|---|---|---|---|---|
| Asn | Met | Val | Val | Arg 425 | Ala | Cys | Gly | Cys | His 430 | | | |

| ACCTTTGCGG | GGCCACACCT | TTCCAAATCT | TCGATGTCTC | ACCATCTAAG | TCTCTCACTG | 1473 |
|---|---|---|---|---|---|---|
| CCCACCTTGG | CGAGGAGAAC | AGACCAACCT | CTCCTGAGCC | TTCCCTCACC | TCCCAACCGG | 1533 |
| AAGCATGTAA | GGGTTCCAGA | AACCTGAGCG | TGCAGCAGCT | GATGAGCGCC | CTTTCCTTCT | 1593 |
| GGCACGTGAC | GGACAAGATC | CTACCAGCTA | CCACAGCAAA | CGCCTAAGAG | CAGGAAAAAT | 1653 |
| GTCTGCCAGG | AAAGTGTCCA | GTGTCCACAT | GGCCCCTGGC | GCTCTGAGTC | TTTGAGGAGT | 1713 |
| AATCGCAAGC | CTCGTTCAGC | TGCAGCAGAA | GGAAGGGCTT | AGCCAGGGTG | GGCGCTGGCG | 1773 |
| TCTGTGTTGA | AGGGAAACCA | AGCAGAAGCC | ACTGTAATGA | TATGTCACAA | TAAAACCCAT | 1833 |
| GAATGAAAAA | AAAAAAAAAA | AAAAAAAAAA | AAAAGAATTC | | | 1873 |

( 2 ) INFORMATION FOR SEQ ID NO:19:

( i ) SEQUENCE CHARACTERISTICS:
  ( A ) LENGTH: 430 amino acids
  ( B ) TYPE: amino acid
  ( D ) TOPOLOGY: linear ( i i ) MOLECULE TYPE: protein ( x i ) SEQUENCE DESCRIPTION: SEQ ID NO:19:

|  |  |  |  |  |  |  |  |  |  |  |  |  |  |  |
|---|---|---|---|---|---|---|---|---|---|---|---|---|---|---|
| Met 1 | His | Val | Arg | Ser 5 | Leu | Arg | Ala | Ala | Ala 10 | Pro | His | Ser | Phe | Val 15 | Ala |
| Leu | Trp | Ala | Pro 20 | Leu | Phe | Leu | Leu | Arg 25 | Ser | Ala | Leu | Ala | Asp 30 | Phe | Ser |
| Leu | Asp | Asn 35 | Glu | Val | His | Ser | Ser 40 | Phe | Ile | His | Arg | Arg 45 | Leu | Arg | Ser |
| Gln | Glu 50 | Arg | Arg | Glu | Met | Gln 55 | Arg | Glu | Ile | Leu | Ser 60 | Ile | Leu | Gly | Leu |
| Pro | His | Arg | Pro | Arg | Pro | His | Leu | Gln | Gly | Lys | His | Asn | Ser | Ala | Pro |

|  |  |  |  | 65 |  |  |  | 70 |  |  |  | 75 |  |  | 80 |
|---|---|---|---|---|---|---|---|---|---|---|---|---|---|---|---|
| Met | Phe | Met | Leu | Asp | Leu | Tyr | Asn | Ala | Met | Ala | Val | Glu | Glu | Ser | Gly |
|  |  |  |  | 85 |  |  |  | 90 |  |  |  | 95 |  |  |  |
| Pro | Asp | Gly | Gln | Gly | Phe | Ser | Tyr | Pro | Tyr | Lys | Ala | Val | Phe | Ser | Thr |
|  |  |  | 100 |  |  |  |  | 105 |  |  |  | 110 |  |  |  |
| Gln | Gly | Pro | Pro | Leu | Ala | Ser | Leu | Gln | Asp | Ser | His | Phe | Leu | Thr | Asp |
|  |  | 115 |  |  |  |  | 120 |  |  |  |  | 125 |  |  |  |
| Ala | Asp | Met | Val | Met | Ser | Phe | Val | Asn | Leu | Val | Glu | His | Asp | Lys | Glu |
|  | 130 |  |  |  |  | 135 |  |  |  |  | 140 |  |  |  |  |
| Phe | Phe | His | Pro | Arg | Tyr | His | His | Arg | Glu | Phe | Arg | Phe | Asp | Leu | Ser |
| 145 |  |  |  |  | 150 |  |  |  | 155 |  |  |  |  |  | 160 |
| Lys | Ile | Pro | Glu | Gly | Glu | Arg | Val | Thr | Ala | Ala | Glu | Phe | Arg | Ile | Tyr |
|  |  |  |  | 165 |  |  |  | 170 |  |  |  |  |  | 175 |  |
| Lys | Asp | Tyr | Ile | Arg | Glu | Arg | Phe | Asp | Asn | Glu | Thr | Phe | Gln | Ile | Thr |
|  |  |  | 180 |  |  |  |  | 185 |  |  |  |  | 190 |  |  |
| Val | Tyr | Gln | Val | Leu | Gln | Glu | His | Ser | Gly | Arg | Glu | Ser | Asp | Leu | Phe |
|  |  | 195 |  |  |  |  | 200 |  |  |  |  | 205 |  |  |  |
| Leu | Leu | Asp | Ser | Arg | Thr | Ile | Trp | Ala | Ser | Glu | Glu | Gly | Trp | Leu | Val |
|  | 210 |  |  |  |  | 215 |  |  |  |  | 220 |  |  |  |  |
| Phe | Asp | Ile | Thr | Ala | Thr | Ser | Asn | His | Trp | Val | Val | Asn | Pro | Arg | His |
| 225 |  |  |  |  | 230 |  |  |  |  | 235 |  |  |  |  | 240 |
| Asn | Leu | Gly | Leu | Gln | Leu | Ser | Val | Glu | Thr | Leu | Asp | Gly | Gln | Ser | Ile |
|  |  |  |  | 245 |  |  |  | 250 |  |  |  |  |  | 255 |  |
| Asn | Pro | Lys | Leu | Ala | Gly | Leu | Ile | Gly | Arg | His | Gly | Pro | Gln | Asn | Lys |
|  |  |  | 260 |  |  |  |  | 265 |  |  |  |  | 270 |  |  |
| Gln | Pro | Phe | Met | Val | Ala | Phe | Phe | Lys | Ala | Thr | Glu | Val | His | Leu | Arg |
|  |  | 275 |  |  |  |  | 280 |  |  |  |  | 285 |  |  |  |
| Ser | Ile | Arg | Ser | Thr | Gly | Gly | Lys | Gln | Arg | Ser | Gln | Asn | Arg | Ser | Lys |
|  | 290 |  |  |  |  | 295 |  |  |  |  | 300 |  |  |  |  |
| Thr | Pro | Lys | Asn | Gln | Glu | Ala | Leu | Arg | Met | Ala | Ser | Val | Ala | Glu | Asn |
| 305 |  |  |  |  | 310 |  |  |  |  | 315 |  |  |  |  | 320 |
| Ser | Ser | Ser | Asp | Gln | Arg | Gln | Ala | Cys | Lys | Lys | His | Glu | Leu | Tyr | Val |
|  |  |  |  | 325 |  |  |  | 330 |  |  |  |  |  | 335 |  |
| Ser | Phe | Arg | Asp | Leu | Gly | Trp | Gln | Asp | Trp | Ile | Ile | Ala | Pro | Glu | Gly |
|  |  |  | 340 |  |  |  |  | 345 |  |  |  |  | 350 |  |  |
| Tyr | Ala | Ala | Tyr | Tyr | Cys | Glu | Gly | Glu | Cys | Ala | Phe | Pro | Leu | Asn | Ser |
|  |  | 355 |  |  |  |  | 360 |  |  |  |  | 365 |  |  |  |
| Tyr | Met | Asn | Ala | Thr | Asn | His | Ala | Ile | Val | Gln | Thr | Leu | Val | His | Phe |
|  | 370 |  |  |  |  | 375 |  |  |  |  | 380 |  |  |  |  |
| Ile | Asn | Pro | Asp | Thr | Val | Pro | Lys | Pro | Cys | Cys | Ala | Pro | Thr | Gln | Leu |
| 385 |  |  |  |  | 390 |  |  |  |  | 395 |  |  |  |  | 400 |
| Asn | Ala | Ile | Ser | Val | Leu | Tyr | Phe | Asp | Asp | Ser | Ser | Asn | Val | Ile | Leu |
|  |  |  |  | 405 |  |  |  | 410 |  |  |  |  |  | 415 |  |
| Lys | Lys | Tyr | Arg | Asn | Met | Val | Val | Arg | Ala | Cys | Gly | Cys | His |  |  |
|  |  |  | 420 |  |  |  |  | 425 |  |  |  |  | 430 |  |  |

( 2 ) INFORMATION FOR SEQ ID NO:20:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

( A ) NAME/KEY: CDS
( B ) LOCATION: 490..1695

( x i ) SEQUENCE DESCRIPTION: SEQ ID NO:20:

| | | |
|---|---|---|
| GGCGCCGGCA GAGCAGGAGT GGCTGGAGGA GCTGTGGTTG GAGCAGGAGG TGGCACGGCA | 60 |
| GGGCTGGAGG GCTCCCTATG AGTGGCGGAG ACGGCCCAGG AGGCGCTGGA GCAACAGCTC | 120 |
| CCACACCGCA CCAAGCGGTG GCTGCAGGAG CTCGCCCATC GCCCCTGCGC TGCTCGGACC | 180 |
| GCGGCCACAG CCGGACTGGC GGGTACGGCG GCGACAGAGG CATTGGCCGA GAGTCCCAGT | 240 |
| CCGCAGAGTA GCCCCGGCCT CGAGGCGGTG GCGTCCCGGT CCTCTCCGTC CAGGAGCCAG | 300 |
| GACAGGTGTC GCGCGGCGGG GCTCCAGGGA CCGCGCCTGA GGCCGGCTGC CCGCCCGTCC | 360 |
| CGCCCCGCCC CGCCGCCCGC CGCCCGCCGA GCCCAGCCTC CTTGCCGTCG GGGCGTCCCC | 420 |
| AGGCCCTGGG TCGGCCGCGG AGCCGATGCG CGCCCGCTGA GCGCCCAGC TGAGCGCCCC | 480 |

```
CGGCCTGCC ATG ACC GCG CTC CCC GGC CCG CTC TGG CTC CTG GGC CTG            528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC          576
Ala Leu Cys Ala Leu Gly Gly Gly Gly Pro Gly Leu Arg Pro Pro Pro
         15              20                  25

GGC TGT CCC CAG CGA CGT CTG GGC GCG CGC GAG CGC CGG GAC GTG CAG          624
Gly Cys Pro Gln Arg Arg Leu Gly Ala Arg Glu Arg Arg Asp Val Gln
 30              35                  40                      45

CGC GAG ATC CTG GCG GTG CTC GGG CTG CCT GGG CGG CCC CGG CCC CGC          672
Arg Glu Ile Leu Ala Val Leu Gly Leu Pro Gly Arg Pro Arg Pro Arg
             50                  55                  60

GCG CCA CCC GCC GCC TCC CGG CTG CCC GCG TCC GCG CCG CTC TTC ATG          720
Ala Pro Pro Ala Ala Ser Arg Leu Pro Ala Ser Ala Pro Leu Phe Met
             65                  70                  75

CTG GAC CTG TAC CAC GCC ATG GCC GGC GAC GAC GAC GAG GAC GGC GCG          768
Leu Asp Leu Tyr His Ala Met Ala Gly Asp Asp Asp Glu Asp Gly Ala
             80                  85                  90

CCC GCG GAG CGG CGC CTG GGC CGC GCC GAC CTG GTC ATG AGC TTC GTT          816
Pro Ala Glu Arg Arg Leu Gly Arg Ala Asp Leu Val Met Ser Phe Val
         95                  100                 105

AAC ATG GTG GAG CGA GAC CGT GCC CTG GGC CAC CAG GAG CCC CAT TGG          864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC          912
Lys Glu Phe Arg Phe Asp Leu Thr Gln Ile Pro Ala Gly Glu Ala Val
             130                 135                 140

ACA GCT GCG GAG TTC CGG ATT TAC AAG GTG CCC AGC ATC CAC CTG CTC          960
Thr Ala Ala Glu Phe Arg Ile Tyr Lys Val Pro Ser Ile His Leu Leu
             145                 150                 155

AAC AGG ACC CTC CAC GTC AGC ATG TTC CAG GTG GTC CAG GAG CAG TCC         1008
Asn Arg Thr Leu His Val Ser Met Phe Gln Val Val Gln Glu Gln Ser
160                 165                 170

AAC AGG GAG TCT GAC TTG TTC TTT TTG GAT CTT CAG ACG CTC CGA GCT         1056
Asn Arg Glu Ser Asp Leu Phe Phe Leu Asp Leu Gln Thr Leu Arg Ala
             175                 180                 185

GGA GAC GAG GGC TGG CTG GTG CTG GAT GTC ACA GCA GCC AGT GAC TGC         1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG         1152
Trp Leu Leu Lys Arg His Lys Asp Leu Gly Leu Arg Leu Tyr Val Glu
             210                 215                 220

ACT GAG GAC GGG CAC AGC GTG GAT CCT GGC CTG GCC GGC CTG CTG GGT         1200
Thr Glu Asp Gly His Ser Val Asp Pro Gly Leu Ala Gly Leu Leu Gly
             225                 230                 235
```

| | | | | | | | | | | | | | | | | |
|---|---|---|---|---|---|---|---|---|---|---|---|---|---|---|---|---|
| CAA | CGG | GCC | CCA | CGC | TCC | CAA | CAG | CCT | TTC | GTG | GTC | ACT | TTC | TTC | AGG | 1248 |
| Gln | Arg | Ala | Pro | Arg | Ser | Gln | Gln | Pro | Phe | Val | Val | Thr | Phe | Phe | Arg | |
| | | 240 | | | | 245 | | | | | 250 | | | | | |
| GCC | AGT | CCG | AGT | CCC | ATC | CGC | ACC | CCT | CGG | GCA | GTG | AGG | CCA | CTG | AGG | 1296 |
| Ala | Ser | Pro | Ser | Pro | Ile | Arg | Thr | Pro | Arg | Ala | Val | Arg | Pro | Leu | Arg | |
| | 255 | | | | 260 | | | | | 265 | | | | | | |
| AGG | AGG | CAG | CCG | AAG | AAA | AGC | AAC | GAG | CTG | CCG | CAG | GCC | AAC | CGA | CTC | 1344 |
| Arg | Arg | Gln | Pro | Lys | Lys | Ser | Asn | Glu | Leu | Pro | Gln | Ala | Asn | Arg | Leu | |
| 270 | | | | | 275 | | | | | 280 | | | | | 285 | |
| CCA | GGG | ATC | TTT | GAT | GAC | GTC | CAC | GGC | TCC | CAC | GGC | CGG | CAG | GTC | TGC | 1392 |
| Pro | Gly | Ile | Phe | Asp | Asp | Val | His | Gly | Ser | His | Gly | Arg | Gln | Val | Cys | |
| | | | | 290 | | | | | 295 | | | | | 300 | | |
| CGT | CGG | CAC | GAG | CTC | TAC | GTC | AGC | TTC | CAG | GAC | CTC | GGC | TGG | CTG | GAC | 1440 |
| Arg | Arg | His | Glu | Leu | Tyr | Val | Ser | Phe | Gln | Asp | Leu | Gly | Trp | Leu | Asp | |
| | | | 305 | | | | | 310 | | | | | 315 | | | |
| TGG | GTC | ATC | GCT | CCC | CAA | GGC | TAC | TCG | GCC | TAT | TAC | TGT | GAG | GGG | GAG | 1488 |
| Trp | Val | Ile | Ala | Pro | Gln | Gly | Tyr | Ser | Ala | Tyr | Tyr | Cys | Glu | Gly | Glu | |
| | | | 320 | | | | | 325 | | | | | 330 | | | |
| TGC | TCC | TTC | CCA | CTG | GAC | TCC | TGC | ATG | AAT | GCC | ACC | AAC | CAC | GCC | ATC | 1536 |
| Cys | Ser | Phe | Pro | Leu | Asp | Ser | Cys | Met | Asn | Ala | Thr | Asn | His | Ala | Ile | |
| | 335 | | | | | 340 | | | | | 345 | | | | | |
| CTG | CAG | TCC | CTG | GTG | CAC | CTG | ATG | AAG | CCA | AAC | GCA | GTC | CCC | AAG | GCG | 1584 |
| Leu | Gln | Ser | Leu | Val | His | Leu | Met | Lys | Pro | Asn | Ala | Val | Pro | Lys | Ala | |
| 350 | | | | | 355 | | | | | 360 | | | | | 365 | |
| TGC | TGT | GCA | CCC | ACC | AAG | CTG | AGC | GCC | ACC | TCT | GTG | CTC | TAC | TAT | GAC | 1632 |
| Cys | Cys | Ala | Pro | Thr | Lys | Leu | Ser | Ala | Thr | Ser | Val | Leu | Tyr | Tyr | Asp | |
| | | | | 370 | | | | | 375 | | | | | 380 | | |
| AGC | AGC | AAC | AAC | GTC | ATC | CTG | CGC | AAA | CAC | CGC | AAC | ATG | GTG | GTC | AAG | 1680 |
| Ser | Ser | Asn | Asn | Val | Ile | Leu | Arg | Lys | His | Arg | Asn | Met | Val | Val | Lys | |
| | | | 385 | | | | | 390 | | | | | 395 | | | |
| GCC | TGC | GGC | TGC | CAC | TGAGTCAGCC | CGCCCAGCCC | TACTGCAG | | | | | | | | | 1723 |
| Ala | Cys | Gly | Cys | His | | | | | | | | | | | | |
| | | | 400 | | | | | | | | | | | | | |

( 2 ) INFORMATION FOR SEQ ID NO:21:

( i ) SEQUENCE CHARACTERISTICS:
  ( A ) LENGTH: 402 amino acids
  ( B ) TYPE: amino acid
  ( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
| Met | Thr | Ala | Leu | Pro | Gly | Pro | Leu | Trp | Leu | Gly | Leu | Ala | Leu | Cys |
| 1 | | | | 5 | | | | 10 | | | | | 15 | |
| Ala | Leu | Gly | Gly | Gly | Gly | Pro | Gly | Leu | Arg | Pro | Pro | Pro | Gly | Cys | Pro |
| | | | 20 | | | | | 25 | | | | | 30 | | |
| Gln | Arg | Arg | Leu | Gly | Ala | Arg | Glu | Arg | Arg | Asp | Val | Gln | Arg | Glu | Ile |
| | | 35 | | | | | 40 | | | | | 45 | | | |
| Leu | Ala | Val | Leu | Gly | Leu | Pro | Gly | Arg | Pro | Arg | Pro | Arg | Ala | Pro | Pro |
| | 50 | | | | | 55 | | | | | 60 | | | | |
| Ala | Ala | Ser | Arg | Leu | Pro | Ala | Ser | Ala | Pro | Leu | Phe | Met | Leu | Asp | Leu |
| 65 | | | | | 70 | | | | | 75 | | | | | 80 |
| Tyr | His | Ala | Met | Ala | Gly | Asp | Asp | Asp | Glu | Asp | Gly | Ala | Pro | Ala | Glu |
| | | | | 85 | | | | | 90 | | | | | 95 | |
| Arg | Arg | Leu | Gly | Arg | Ala | Asp | Leu | Val | Met | Ser | Phe | Val | Asn | Met | Val |
| | | | 100 | | | | | 105 | | | | | 110 | | |
| Glu | Arg | Asp | Arg | Ala | Leu | Gly | His | Gln | Glu | Pro | His | Trp | Lys | Glu | Phe |
| | | 115 | | | | | 120 | | | | | 125 | | | |

| | | | | | | | | | | | | | | |
|---|---|---|---|---|---|---|---|---|---|---|---|---|---|---|
| Arg | Phe | Asp | Leu | Thr | Gln | Ile | Pro | Ala | Gly | Glu | Ala | Val | Thr | Ala | Ala |
| | 130 | | | | 135 | | | | 140 | | | | | | |
| Glu | Phe | Arg | Ile | Tyr | Lys | Val | Pro | Ser | Ile | His | Leu | Leu | Asn | Arg | Thr |
| 145 | | | | | 150 | | | | 155 | | | | | | 160 |
| Leu | His | Val | Ser | Met | Phe | Gln | Val | Val | Gln | Glu | Gln | Ser | Asn | Arg | Glu |
| | | | | 165 | | | | | 170 | | | | | 175 | |
| Ser | Asp | Leu | Phe | Phe | Leu | Asp | Leu | Gln | Thr | Leu | Arg | Ala | Gly | Asp | Glu |
| | | | 180 | | | | | 185 | | | | | 190 | | |
| Gly | Trp | Leu | Val | Leu | Asp | Val | Thr | Ala | Ala | Ser | Asp | Cys | Trp | Leu | Leu |
| | | 195 | | | | | 200 | | | | | 205 | | | |
| Lys | Arg | His | Lys | Asp | Leu | Gly | Leu | Arg | Leu | Tyr | Val | Glu | Thr | Glu | Asp |
| | 210 | | | | | 215 | | | | | 220 | | | | |
| Gly | His | Ser | Val | Asp | Pro | Gly | Leu | Ala | Gly | Leu | Leu | Gly | Gln | Arg | Ala |
| 225 | | | | | 230 | | | | | 235 | | | | | 240 |
| Pro | Arg | Ser | Gln | Gln | Pro | Phe | Val | Val | Thr | Phe | Phe | Arg | Ala | Ser | Pro |
| | | | | 245 | | | | | 250 | | | | | 255 | |
| Ser | Pro | Ile | Arg | Thr | Pro | Arg | Ala | Val | Arg | Pro | Leu | Arg | Arg | Arg | Gln |
| | | | 260 | | | | | 265 | | | | | 270 | | |
| Pro | Lys | Lys | Ser | Asn | Glu | Leu | Pro | Gln | Ala | Asn | Arg | Leu | Pro | Gly | Ile |
| | | 275 | | | | | 280 | | | | | 285 | | | |
| Phe | Asp | Asp | Val | His | Gly | Ser | His | Gly | Arg | Gln | Val | Cys | Arg | Arg | His |
| | 290 | | | | | 295 | | | | | 300 | | | | |
| Glu | Leu | Tyr | Val | Ser | Phe | Gln | Asp | Leu | Gly | Trp | Leu | Asp | Trp | Val | Ile |
| 305 | | | | | 310 | | | | | 315 | | | | | 320 |
| Ala | Pro | Gln | Gly | Tyr | Ser | Ala | Tyr | Tyr | Cys | Glu | Gly | Glu | Cys | Ser | Phe |
| | | | | 325 | | | | | 330 | | | | | 335 | |
| Pro | Leu | Asp | Ser | Cys | Met | Asn | Ala | Thr | Asn | His | Ala | Ile | Leu | Gln | Ser |
| | | | 340 | | | | | 345 | | | | | 350 | | |
| Leu | Val | His | Leu | Met | Lys | Pro | Asn | Ala | Val | Pro | Lys | Ala | Cys | Cys | Ala |
| | | 355 | | | | | 360 | | | | | 365 | | | |
| Pro | Thr | Lys | Leu | Ser | Ala | Thr | Ser | Val | Leu | Tyr | Tyr | Asp | Ser | Ser | Asn |
| | 370 | | | | | 375 | | | | | 380 | | | | |
| Asn | Val | Ile | Leu | Arg | Lys | His | Arg | Asn | Met | Val | Val | Lys | Ala | Cys | Gly |
| 385 | | | | | 390 | | | | | 395 | | | | | 400 |
| Cys | His | | | | | | | | | | | | | | |

( 2 ) INFORMATION FOR SEQ ID NO:22:

( i ) SEQUENCE CHARACTERISTICS:
        ( A ) LENGTH: 1926 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 93..1289
        ( D ) OTHER INFORMATION: /product="MOP2 CDNA"

( x i ) SEQUENCE DESCRIPTION: SEQ ID NO:22:

```
GCCAGGCACA GGTGCGCCGT CTGGTCCTCC CCGTCTGGCG TCAGCCGAGC CCGACCAGCT        60

ACCAGTGGAT GCGCGCCGGC TGAAAGTCCG AG ATG GCT ATG CGT CCC GGG CCA        113
                                   Met Ala Met Arg Pro Gly Pro
                                    1               5

CTC TGG CTA TTG GGC CTT GCT CTG TGC GCG CTG GGA GGC GGC CAC GGT        161
Leu Trp Leu Leu Gly Leu Ala Leu Cys Ala Leu Gly Gly Gly His Gly
```

|  |  |  |  |  |  |  |  |  |  |  |  |  |  |  |  |
|---|---|---|---|---|---|---|---|---|---|---|---|---|---|---|---|
|  |  | 10 |  |  |  |  | 15 |  |  |  |  | 20 |  |  |  |
| CCG | CGT | CCC | CCG | CAC | ACC | TGT | CCC | CAG | CGT | CGC | CTG | GGA | GCG | CGC | GAG | 209 |
| Pro | Arg | Pro | Pro | His | Thr | Cys | Pro | Gln | Arg | Arg | Leu | Gly | Ala | Arg | Glu |
| 25 |  |  |  |  | 30 |  |  |  |  | 35 |  |  |  |  |  |
| CGC | CGC | GAC | ATG | CAG | CGT | GAA | ATC | CTG | GCG | GTG | CTC | GGG | CTA | CCG | GGA | 257 |
| Arg | Arg | Asp | Met | Gln | Arg | Glu | Ile | Leu | Ala | Val | Leu | Gly | Leu | Pro | Gly |
| 40 |  |  |  |  | 45 |  |  |  |  | 50 |  |  |  |  | 55 |
| CGG | CCC | CGA | CCC | CGT | GCA | CAA | CCC | GCG | GCT | GCC | CGG | CAG | CCA | GCG | TCC | 305 |
| Arg | Pro | Arg | Pro | Arg | Ala | Gln | Pro | Ala | Ala | Ala | Arg | Gln | Pro | Ala | Ser |
|  |  |  |  | 60 |  |  |  |  | 65 |  |  |  |  | 70 |  |
| GCG | CCC | CTC | TTC | ATG | TTG | GAC | CTA | TAC | CAC | GCC | ATG | ACC | GAT | GAC | GAC | 353 |
| Ala | Pro | Leu | Phe | Met | Leu | Asp | Leu | Tyr | His | Ala | Met | Thr | Asp | Asp | Asp |
|  |  |  | 75 |  |  |  |  | 80 |  |  |  |  | 85 |  |  |
| GAC | GGC | GGG | CCA | CCA | CAG | GCT | CAC | TTA | GGC | CGT | GCC | GAC | CTG | GTC | ATG | 401 |
| Asp | Gly | Gly | Pro | Pro | Gln | Ala | His | Leu | Gly | Arg | Ala | Asp | Leu | Val | Met |
|  |  | 90 |  |  |  |  | 95 |  |  |  |  | 100 |  |  |  |
| AGC | TTC | GTC | AAC | ATG | GTG | GAA | CGC | GAC | CGT | ACC | CTG | GGC | TAC | CAG | GAG | 449 |
| Ser | Phe | Val | Asn | Met | Val | Glu | Arg | Asp | Arg | Thr | Leu | Gly | Tyr | Gln | Glu |
|  | 105 |  |  |  |  | 110 |  |  |  |  | 115 |  |  |  |  |
| CCA | CAC | TGG | AAG | GAA | TTC | CAC | TTT | GAC | CTA | ACC | CAG | ATC | CCT | GCT | GGG | 497 |
| Pro | His | Trp | Lys | Glu | Phe | His | Phe | Asp | Leu | Thr | Gln | Ile | Pro | Ala | Gly |
| 120 |  |  |  |  | 125 |  |  |  |  | 130 |  |  |  |  | 135 |
| GAG | GCT | GTC | ACA | GCT | GCT | GAG | TTC | CGG | ATC | TAC | AAA | GAA | CCC | AGC | ACC | 545 |
| Glu | Ala | Val | Thr | Ala | Ala | Glu | Phe | Arg | Ile | Tyr | Lys | Glu | Pro | Ser | Thr |
|  |  |  | 140 |  |  |  |  | 145 |  |  |  |  | 150 |  |  |
| CAC | CCG | CTC | AAC | ACA | ACC | CTC | CAC | ATC | AGC | ATG | TTC | GAA | GTG | GTC | CAA | 593 |
| His | Pro | Leu | Asn | Thr | Thr | Leu | His | Ile | Ser | Met | Phe | Glu | Val | Val | Gln |
|  |  |  | 155 |  |  |  |  | 160 |  |  |  |  | 165 |  |  |
| GAG | CAC | TCC | AAC | AGG | GAG | TCT | GAC | TTG | TTC | TTT | TTG | GAT | CTT | CAG | ACG | 641 |
| Glu | His | Ser | Asn | Arg | Glu | Ser | Asp | Leu | Phe | Phe | Leu | Asp | Leu | Gln | Thr |
|  |  | 170 |  |  |  |  | 175 |  |  |  |  | 180 |  |  |  |
| CTC | CGA | TCT | GGG | GAC | GAG | GGC | TGG | CTG | GTG | CTG | GAC | ATC | ACA | GCA | GCC | 689 |
| Leu | Arg | Ser | Gly | Asp | Glu | Gly | Trp | Leu | Val | Leu | Asp | Ile | Thr | Ala | Ala |
|  | 185 |  |  |  |  | 190 |  |  |  |  | 195 |  |  |  |  |
| AGT | GAC | CGA | TGG | CTG | CTG | AAC | CAT | CAC | AAG | GAC | CTG | GGA | CTC | CGC | CTC | 737 |
| Ser | Asp | Arg | Trp | Leu | Leu | Asn | His | His | Lys | Asp | Leu | Gly | Leu | Arg | Leu |
| 200 |  |  |  |  | 205 |  |  |  |  | 210 |  |  |  |  | 215 |
| TAT | GTG | GAA | ACC | GCG | GAT | GGG | CAC | AGC | ATG | GAT | CCT | GGC | CTG | GCT | GGT | 785 |
| Tyr | Val | Glu | Thr | Ala | Asp | Gly | His | Ser | Met | Asp | Pro | Gly | Leu | Ala | Gly |
|  |  |  | 220 |  |  |  |  | 225 |  |  |  |  | 230 |  |  |
| CTG | CTT | GGA | CGA | CAA | GCA | CCA | CGC | TCC | AGA | CAG | CCT | TTC | ATG | GTA | ACC | 833 |
| Leu | Leu | Gly | Arg | Gln | Ala | Pro | Arg | Ser | Arg | Gln | Pro | Phe | Met | Val | Thr |
|  |  | 235 |  |  |  |  | 240 |  |  |  |  | 245 |  |  |  |
| TTC | TTC | AGG | GCC | AGC | CAG | AGT | CCT | GTG | CGG | GCC | CCT | CGG | GCA | GCG | AGA | 881 |
| Phe | Phe | Arg | Ala | Ser | Gln | Ser | Pro | Val | Arg | Ala | Pro | Arg | Ala | Ala | Arg |
|  | 250 |  |  |  |  | 255 |  |  |  |  | 260 |  |  |  |  |
| CCA | CTG | AAG | AGG | AGG | CAG | CCA | AAG | AAA | ACG | AAC | GAG | CTT | CCG | CAC | CCC | 929 |
| Pro | Leu | Lys | Arg | Arg | Gln | Pro | Lys | Lys | Thr | Asn | Glu | Leu | Pro | His | Pro |
| 265 |  |  |  |  | 270 |  |  |  |  | 275 |  |  |  |  |  |
| AAC | AAA | CTC | CCA | GGG | ATC | TTT | GAT | GAT | GGC | CAC | GGT | TCC | CGC | GGC | AGA | 977 |
| Asn | Lys | Leu | Pro | Gly | Ile | Phe | Asp | Asp | Gly | His | Gly | Ser | Arg | Gly | Arg |
| 280 |  |  |  |  | 285 |  |  |  |  | 290 |  |  |  |  | 295 |
| GAG | GTT | TGC | CGC | AGG | CAT | GAG | CTC | TAC | GTC | AGC | TTC | CGT | GAC | CTT | GGC | 1025 |
| Glu | Val | Cys | Arg | Arg | His | Glu | Leu | Tyr | Val | Ser | Phe | Arg | Asp | Leu | Gly |
|  |  |  | 300 |  |  |  |  | 305 |  |  |  |  | 310 |  |  |
| TGG | CTG | GAC | TGG | GTC | ATC | GCC | CCC | CAG | GGC | TAC | TCT | GCC | TAT | TAC | TGT | 1073 |
| Trp | Leu | Asp | Trp | Val | Ile | Ala | Pro | Gln | Gly | Tyr | Ser | Ala | Tyr | Tyr | Cys |
|  |  | 315 |  |  |  |  | 320 |  |  |  |  | 325 |  |  |  |
| GAG | GGG | GAG | TGT | GCT | TTC | CCA | CTG | GAC | TCC | TGT | ATG | AAC | GCC | ACC | AAC | 1121 |
| Glu | Gly | Glu | Cys | Ala | Phe | Pro | Leu | Asp | Ser | Cys | Met | Asn | Ala | Thr | Asn |

|  |  |  |  |  |  |  |  |  |  |  |  |  |  |  |  |
|--|--|--|--|--|--|--|--|--|--|--|--|--|--|--|--|
| | 330 | | | | | 335 | | | | | 340 | | | | |

```
CAT  GCC  ATC  TTG  CAG  TCT  CTG  GTG  CAC  CTG  ATG  AAG  CCA  GAT  GTT  GTC      1169
His  Ala  Ile  Leu  Gln  Ser  Leu  Val  His  Leu  Met  Lys  Pro  Asp  Val  Val
     345                      350                     355

CCC  AAG  GCA  TGC  TGT  GCA  CCC  ACC  AAA  CTG  AGT  GCC  ACC  TCT  GTG  CTG      1217
Pro  Lys  Ala  Cys  Cys  Ala  Pro  Thr  Lys  Leu  Ser  Ala  Thr  Ser  Val  Leu
360                      365                     370                      375

TAC  TAT  GAC  AGC  AGC  AAC  AAT  GTC  ATC  CTG  CGT  AAA  CAC  CGT  AAC  ATG      1265
Tyr  Tyr  Asp  Ser  Ser  Asn  Asn  Val  Ile  Leu  Arg  Lys  His  Arg  Asn  Met
                    380                     385                      390

GTG  GTC  AAG  GCC  TGT  GGC  TGC  CAC  TGAGGCCCCG  CCCAGCATCC  TGCTTCTACT          1319
Val  Val  Lys  Ala  Cys  Gly  Cys  His
               395
```

| | |
|--|--|
| ACCTTACCAT CTGGCCGGGC CCCTCTCCAG AGGCAGAAAC CCTTCTATGT TATCATAGCT | 1379 |
| CAGACAGGGG CAATGGGAGG CCCTTCACTT CCCCTGGCCA CTTCCTGCTA AAATTCTGGT | 1439 |
| CTTTCCCAGT TCCTCTGTCC TTCATGGGGT TTCGGGGCTA TCACCCCGCC CTCTCCATCC | 1499 |
| TCCTACCCCA AGCATAGACT GAATGCACAC AGCATCCCAG AGCTATGCTA ACTGAGAGGT | 1559 |
| CTGGGGTCAG CACTGAAGGC CCACATGAGG AAGACTGATC CTTGGCCATC CTCAGCCCAC | 1619 |
| AATGGCAAAT TCTGGATGGT CTAAGAAGGC CGTGGAATTC TAAACTAGAT GATCTGGGCT | 1679 |
| CTCTGCACCA TTCATTGTGG CAGTTGGGAC ATTTTTAGGT ATAACAGACA CATACACTTA | 1739 |
| GATCAATGCA TCGCTGTACT CCTTGAAATC AGAGCTAGCT TGTTAGAAAA AGAATCAGAG | 1799 |
| CCAGGTATAG CGGTGCATGT CATTAATCCC AGCGCTAAAG AGACAGAGAC AGGAGAATCT | 1859 |
| CTGTGAGTTC AAGGCCACAT AGAAAGAGCC TGTCTCGGGA GCAGGAAAAA AAAAAAAAAC | 1919 |
| GGAATTC | 1926 |

( 2 ) INFORMATION FOR SEQ ID NO:23:

( i ) SEQUENCE CHARACTERISTICS:
        ( A ) LENGTH: 399 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Met  Ala  Met  Arg  Pro  Gly  Pro  Leu  Trp  Leu  Gly  Leu  Ala  Leu  Cys
 1                 5                     10                      15

Ala  Leu  Gly  Gly  Gly  His  Gly  Pro  Arg  Pro  Pro  His  Thr  Cys  Pro  Gln
               20                     25                      30

Arg  Arg  Leu  Gly  Ala  Arg  Glu  Arg  Arg  Asp  Met  Gln  Arg  Glu  Ile  Leu
          35                      40                      45

Ala  Val  Leu  Gly  Leu  Pro  Gly  Arg  Pro  Arg  Pro  Arg  Ala  Gln  Pro  Ala
     50                      55                      60

Ala  Ala  Arg  Gln  Pro  Ala  Ser  Ala  Pro  Leu  Phe  Met  Leu  Asp  Leu  Tyr
65                      70                      75                      80

His  Ala  Met  Thr  Asp  Asp  Asp  Gly  Gly  Pro  Pro  Gln  Ala  His  Leu
                    85                      90                      95

Gly  Arg  Ala  Asp  Leu  Val  Met  Ser  Phe  Val  Asn  Met  Val  Glu  Arg  Asp
               100                     105                     110

Arg  Thr  Leu  Gly  Tyr  Gln  Glu  Pro  His  Trp  Lys  Glu  Phe  His  Phe  Asp
          115                     120                     125

Leu  Thr  Gln  Ile  Pro  Ala  Gly  Glu  Ala  Val  Thr  Ala  Ala  Glu  Phe  Arg
     130                     135                     140

Ile  Tyr  Lys  Glu  Pro  Ser  Thr  His  Pro  Leu  Asn  Thr  Thr  Leu  His  Ile
```

| | 145 | | | | 150 | | | | 155 | | | | 160 | |
|---|---|---|---|---|---|---|---|---|---|---|---|---|---|---|
| Ser | Met | Phe | Glu | Val | Val | Gln | Glu | His | Ser | Asn | Arg | Glu | Ser | Asp | Leu |
| | | | | | 165 | | | | 170 | | | | 175 | | |
| Phe | Phe | Leu | Asp | Leu | Gln | Thr | Leu | Arg | Ser | Gly | Asp | Glu | Gly | Trp | Leu |
| | | | 180 | | | | | 185 | | | | 190 | | | |
| Val | Leu | Asp | Ile | Thr | Ala | Ala | Ser | Asp | Arg | Trp | Leu | Leu | Asn | His | His |
| | | 195 | | | | 200 | | | | | 205 | | | | |
| Lys | Asp | Leu | Gly | Leu | Arg | Leu | Tyr | Val | Glu | Thr | Ala | Asp | Gly | His | Ser |
| | 210 | | | | | 215 | | | | 220 | | | | | |
| Met | Asp | Pro | Gly | Leu | Ala | Gly | Leu | Leu | Gly | Arg | Gln | Ala | Pro | Arg | Ser |
| 225 | | | | | 230 | | | | 235 | | | | | | 240 |
| Arg | Gln | Pro | Phe | Met | Val | Thr | Phe | Phe | Arg | Ala | Ser | Gln | Ser | Pro | Val |
| | | | | 245 | | | | | 250 | | | | | 255 | |
| Arg | Ala | Pro | Arg | Ala | Ala | Arg | Pro | Leu | Lys | Arg | Arg | Gln | Pro | Lys | Lys |
| | | | 260 | | | | | | 265 | | | | 270 | | |
| Thr | Asn | Glu | Leu | Pro | His | Pro | Asn | Lys | Leu | Pro | Gly | Ile | Phe | Asp | Asp |
| | | 275 | | | | | 280 | | | | | 285 | | | |
| Gly | His | Gly | Ser | Arg | Gly | Arg | Glu | Val | Cys | Arg | Arg | His | Glu | Leu | Tyr |
| | 290 | | | | | 295 | | | | 300 | | | | | |
| Val | Ser | Phe | Arg | Asp | Leu | Gly | Trp | Leu | Asp | Trp | Val | Ile | Ala | Pro | Gln |
| 305 | | | | | 310 | | | | 315 | | | | | | 320 |
| Gly | Tyr | Ser | Ala | Tyr | Tyr | Cys | Glu | Gly | Glu | Cys | Ala | Phe | Pro | Leu | Asp |
| | | | | 325 | | | | | 330 | | | | | 335 | |
| Ser | Cys | Met | Asn | Ala | Thr | Asn | His | Ala | Ile | Leu | Gln | Ser | Leu | Val | His |
| | | | 340 | | | | | 345 | | | | | 350 | | |
| Leu | Met | Lys | Pro | Asp | Val | Val | Pro | Lys | Ala | Cys | Cys | Ala | Pro | Thr | Lys |
| | | 355 | | | | | 360 | | | | | 365 | | | |
| Leu | Ser | Ala | Thr | Ser | Val | Leu | Tyr | Tyr | Asp | Ser | Ser | Asn | Asn | Val | Ile |
| | 370 | | | | | 375 | | | | | 380 | | | | |
| Leu | Arg | Lys | His | Arg | Asn | Met | Val | Val | Lys | Ala | Cys | Gly | Cys | His | |
| 385 | | | | | 390 | | | | 395 | | | | | | |

( 2 ) INFORMATION FOR SEQ ID NO:24:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1365

( x i ) SEQUENCE DESCRIPTION: SEQ ID NO:24:

| ATG | TCG | GGA | CTG | CGA | AAC | ACC | TCG | GAG | GCC | GTT | GCA | GTG | CTC | GCC | TCC | 48 |
|---|---|---|---|---|---|---|---|---|---|---|---|---|---|---|---|---|
| Met | Ser | Gly | Leu | Arg | Asn | Thr | Ser | Glu | Ala | Val | Ala | Val | Leu | Ala | Ser | |
| 1 | | | | 5 | | | | | 10 | | | | | 15 | | |
| CTG | GGA | CTC | GGA | ATG | GTT | CTG | CTC | ATG | TTC | GTG | GCG | ACC | ACG | CCG | CCG | 96 |
| Leu | Gly | Leu | Gly | Met | Val | Leu | Leu | Met | Phe | Val | Ala | Thr | Thr | Pro | Pro | |
| | | | 20 | | | | | 25 | | | | | 30 | | | |
| GCC | GTT | GAG | GCC | ACC | CAG | TCG | GGG | ATT | TAC | ATA | GAC | AAC | GGC | AAG | GAC | 144 |
| Ala | Val | Glu | Ala | Thr | Gln | Ser | Gly | Ile | Tyr | Ile | Asp | Asn | Gly | Lys | Asp | |
| | | 35 | | | | | 40 | | | | | 45 | | | | |
| CAG | ACG | ATC | ATG | CAC | AGA | GTG | CTG | AGC | GAG | GAC | GAC | AAG | CTG | GAC | GTC | 192 |
| Gln | Thr | Ile | Met | His | Arg | Val | Leu | Ser | Glu | Asp | Asp | Lys | Leu | Asp | Val | |
| | 50 | | | | | 55 | | | | | 60 | | | | | |

-continued

| | | | | | | | | | | | | | | | | |
|---|---|---|---|---|---|---|---|---|---|---|---|---|---|---|---|---|
| TCG | TAC | GAG | ATC | CTC | GAG | TTC | CTG | GGC | ATC | GCC | GAA | CGG | CCG | ACG | CAC | 240 |
| Ser | Tyr | Glu | Ile | Leu | Glu | Phe | Leu | Gly | Ile | Ala | Glu | Arg | Pro | Thr | His | |
| 65 | | | | | 70 | | | | 75 | | | | | | 80 | |
| CTG | AGC | AGC | CAC | CAG | TTG | TCG | CTG | AGG | AAG | TCG | GCT | CCC | AAG | TTC | CTG | 288 |
| Leu | Ser | Ser | His | Gln | Leu | Ser | Leu | Arg | Lys | Ser | Ala | Pro | Lys | Phe | Leu | |
| | | | | 85 | | | | | 90 | | | | | 95 | | |
| CTG | GAC | GTC | TAC | CAC | CGC | ATC | ACG | GCG | GAG | GAG | GGT | CTC | AGC | GAT | CAG | 336 |
| Leu | Asp | Val | Tyr | His | Arg | Ile | Thr | Ala | Glu | Glu | Gly | Leu | Ser | Asp | Gln | |
| | | | | 100 | | | | | 105 | | | | | 110 | | |
| GAT | GAG | GAC | GAC | GAC | TAC | GAA | CGC | GGC | CAT | CGG | TCC | AGG | AGG | AGC | GCC | 384 |
| Asp | Glu | Asp | Asp | Asp | Tyr | Glu | Arg | Gly | His | Arg | Ser | Arg | Arg | Ser | Ala | |
| | | | | 115 | | | | | 120 | | | | | 125 | | |
| GAC | CTC | GAG | GAG | GAT | GAG | GGC | GAG | CAG | CAG | AAG | AAC | TTC | ATC | ACC | GAC | 432 |
| Asp | Leu | Glu | Glu | Asp | Glu | Gly | Glu | Gln | Gln | Lys | Asn | Phe | Ile | Thr | Asp | |
| | 130 | | | | | 135 | | | | | 140 | | | | | |
| CTG | GAC | AAG | CGG | GCC | ATC | GAC | GAG | AGC | GAC | ATC | ATC | ATG | ACC | TTC | CTG | 480 |
| Leu | Asp | Lys | Arg | Ala | Ile | Asp | Glu | Ser | Asp | Ile | Ile | Met | Thr | Phe | Leu | |
| 145 | | | | | 150 | | | | | 155 | | | | | 160 | |
| AAC | AAG | CGC | CAC | CAC | AAT | GTG | GAC | GAA | CTG | CGT | CAC | GAG | CAC | GGC | CGT | 528 |
| Asn | Lys | Arg | His | His | Asn | Val | Asp | Glu | Leu | Arg | His | Glu | His | Gly | Arg | |
| | | | | 165 | | | | | 170 | | | | | 175 | | |
| CGC | CTG | TGG | TTC | GAC | GTC | TCC | AAC | GTG | CCC | AAC | GAC | AAC | TAC | CTG | GTG | 576 |
| Arg | Leu | Trp | Phe | Asp | Val | Ser | Asn | Val | Pro | Asn | Asp | Asn | Tyr | Leu | Val | |
| | | | 180 | | | | | 185 | | | | | 190 | | | |
| ATG | GCC | GAG | CTG | CGC | ATC | TAT | CAG | AAC | GCC | AAC | GAG | GGC | AAG | TGG | CTG | 624 |
| Met | Ala | Glu | Leu | Arg | Ile | Tyr | Gln | Asn | Ala | Asn | Glu | Gly | Lys | Trp | Leu | |
| | | | 195 | | | | | 200 | | | | | 205 | | | |
| ACC | GCC | AAC | AGG | GAG | TTC | ACC | ATC | ACG | GTA | TAC | GCC | ATT | GGC | ACC | GGC | 672 |
| Thr | Ala | Asn | Arg | Glu | Phe | Thr | Ile | Thr | Val | Tyr | Ala | Ile | Gly | Thr | Gly | |
| | | 210 | | | | | 215 | | | | | 220 | | | | |
| ACG | CTG | GGC | CAG | CAC | ACC | ATG | GAG | CCG | CTG | TCC | TCG | GTG | AAC | ACC | ACC | 720 |
| Thr | Leu | Gly | Gln | His | Thr | Met | Glu | Pro | Leu | Ser | Ser | Val | Asn | Thr | Thr | |
| 225 | | | | | 230 | | | | | 235 | | | | | 240 | |
| GGG | GAC | TAC | GTG | GGC | TGG | TTG | GAG | CTC | AAC | GTG | ACC | GAG | GGC | CTG | CAC | 768 |
| Gly | Asp | Tyr | Val | Gly | Trp | Leu | Glu | Leu | Asn | Val | Thr | Glu | Gly | Leu | His | |
| | | | 245 | | | | | 250 | | | | | 255 | | | |
| GAG | TGG | CTG | GTC | AAG | TCG | AAG | GAC | AAT | CAT | GGC | ATC | TAC | ATT | GGA | GCA | 816 |
| Glu | Trp | Leu | Val | Lys | Ser | Lys | Asp | Asn | His | Gly | Ile | Tyr | Ile | Gly | Ala | |
| | | | 260 | | | | | 265 | | | | | 270 | | | |
| CAC | GCT | GTC | AAC | CGA | CCC | GAC | CGC | GAG | GTG | AAG | CTG | GAC | GAC | ATT | GGA | 864 |
| His | Ala | Val | Asn | Arg | Pro | Asp | Arg | Glu | Val | Lys | Leu | Asp | Asp | Ile | Gly | |
| | | | 275 | | | | | 280 | | | | | 285 | | | |
| CTG | ATC | CAC | CGC | AAG | GTG | GAC | GAC | GAG | TTC | CAG | CCC | TTC | ATG | ATC | GGC | 912 |
| Leu | Ile | His | Arg | Lys | Val | Asp | Asp | Glu | Phe | Gln | Pro | Phe | Met | Ile | Gly | |
| | | 290 | | | | | 295 | | | | | 300 | | | | |
| TTC | TTC | CGC | GGA | CCG | GAG | CTG | ATC | AAG | GCG | ACG | GCC | CAC | AGC | AGC | CAC | 960 |
| Phe | Phe | Arg | Gly | Pro | Glu | Leu | Ile | Lys | Ala | Thr | Ala | His | Ser | Ser | His | |
| 305 | | | | | 310 | | | | | 315 | | | | | 320 | |
| CAC | AGG | AGC | AAG | CGA | AGC | GCC | AGC | CAT | CCA | CGC | AAG | CGC | AAG | AAG | TCG | 1008 |
| His | Arg | Ser | Lys | Arg | Ser | Ala | Ser | His | Pro | Arg | Lys | Arg | Lys | Lys | Ser | |
| | | | | 325 | | | | | 330 | | | | | 335 | | |
| GTG | TCG | CCC | AAC | AAC | GTG | CCG | CTG | CTG | GAA | CCG | ATG | GAG | AGC | ACG | CGC | 1056 |
| Val | Ser | Pro | Asn | Asn | Val | Pro | Leu | Leu | Glu | Pro | Met | Glu | Ser | Thr | Arg | |
| | | | 340 | | | | | 345 | | | | | 350 | | | |
| AGC | TGC | CAG | ATG | CAG | ACC | CTG | TAC | ATA | GAC | TTC | AAG | GAT | CTG | GGC | TGG | 1104 |
| Ser | Cys | Gln | Met | Gln | Thr | Leu | Tyr | Ile | Asp | Phe | Lys | Asp | Leu | Gly | Trp | |
| | | 355 | | | | | 360 | | | | | 365 | | | | |
| CAT | GAC | TGG | ATC | ATC | GCA | CCA | GAG | GGC | TAT | GGC | GCC | TTC | TAC | TGC | AGC | 1152 |
| His | Asp | Trp | Ile | Ile | Ala | Pro | Glu | Gly | Tyr | Gly | Ala | Phe | Tyr | Cys | Ser | |
| | 370 | | | | | 375 | | | | | 380 | | | | | |

| | | | | | | | | | | | | | | | | |
|---|---|---|---|---|---|---|---|---|---|---|---|---|---|---|---|---|
| GGC | GAG | TGC | AAT | TTC | CCG | CTC | AAT | GCG | CAC | ATG | AAC | GCC | ACG | AAC | CAT | 1200 |
| Gly | Glu | Cys | Asn | Phe | Pro | Leu | Asn | Ala | His | Met | Asn | Ala | Thr | Asn | His | |
| 385 | | | | 390 | | | | | 395 | | | | | | 400 | |
| GCG | ATC | GTC | CAG | ACC | CTG | GTC | CAC | CTG | CTG | GAG | CCC | AAG | AAG | GTG | CCC | 1248 |
| Ala | Ile | Val | Gln | Thr | Leu | Val | His | Leu | Leu | Glu | Pro | Lys | Lys | Val | Pro | |
| | | | | 405 | | | | | 410 | | | | | 415 | | |
| AAG | CCC | TGC | TGC | GCT | CCG | ACC | AGG | CTG | GGA | GCA | CTA | CCC | GTT | CTG | TAC | 1296 |
| Lys | Pro | Cys | Cys | Ala | Pro | Thr | Arg | Leu | Gly | Ala | Leu | Pro | Val | Leu | Tyr | |
| | | | 420 | | | | | 425 | | | | | 430 | | | |
| CAC | CTG | AAC | GAC | GAG | AAT | GTG | AAC | CTG | AAA | AAG | TAT | AGA | AAC | ATG | ATT | 1344 |
| His | Leu | Asn | Asp | Glu | Asn | Val | Asn | Leu | Lys | Lys | Tyr | Arg | Asn | Met | Ile | |
| | | 435 | | | | | 440 | | | | | 445 | | | | |
| GTG | AAA | TCC | TGC | GGG | TGC | CAT | TGA | | | | | | | | | 1368 |
| Val | Lys | Ser | Cys | Gly | Cys | His | | | | | | | | | | |
| | | 450 | | | | 455 | | | | | | | | | | |

( 2 ) INFORMATION FOR SEQ ID NO:25:

( i ) SEQUENCE CHARACTERISTICS:
        ( A ) LENGTH: 455 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | | |
|---|---|---|---|---|---|---|---|---|---|---|---|---|---|---|---|
| Met | Ser | Gly | Leu | Arg | Asn | Thr | Ser | Glu | Ala | Val | Ala | Val | Leu | Ala | Ser |
| 1 | | | | 5 | | | | | 10 | | | | | 15 | |
| Leu | Gly | Leu | Gly | Met | Val | Leu | Leu | Met | Phe | Val | Ala | Thr | Thr | Pro | Pro |
| | | | 20 | | | | | 25 | | | | | 30 | | |
| Ala | Val | Glu | Ala | Thr | Gln | Ser | Gly | Ile | Tyr | Ile | Asp | Asn | Gly | Lys | Asp |
| | | 35 | | | | | 40 | | | | | 45 | | | |
| Gln | Thr | Ile | Met | His | Arg | Val | Leu | Ser | Glu | Asp | Asp | Lys | Leu | Asp | Val |
| | 50 | | | | | 55 | | | | | 60 | | | | |
| Ser | Tyr | Glu | Ile | Leu | Glu | Phe | Leu | Gly | Ile | Ala | Glu | Arg | Pro | Thr | His |
| 65 | | | | | 70 | | | | | 75 | | | | | 80 |
| Leu | Ser | Ser | His | Gln | Leu | Ser | Leu | Arg | Lys | Ser | Ala | Pro | Lys | Phe | Leu |
| | | | | 85 | | | | | 90 | | | | | 95 | |
| Leu | Asp | Val | Tyr | His | Arg | Ile | Thr | Ala | Glu | Glu | Gly | Leu | Ser | Asp | Gln |
| | | | 100 | | | | | 105 | | | | | 110 | | |
| Asp | Glu | Asp | Asp | Asp | Tyr | Glu | Arg | Gly | His | Arg | Ser | Arg | Arg | Ser | Ala |
| | | 115 | | | | | 120 | | | | | 125 | | | |
| Asp | Leu | Glu | Glu | Asp | Glu | Gly | Glu | Gln | Gln | Lys | Asn | Phe | Ile | Thr | Asp |
| | 130 | | | | | 135 | | | | | 140 | | | | |
| Leu | Asp | Lys | Arg | Ala | Ile | Asp | Glu | Ser | Asp | Ile | Ile | Met | Thr | Phe | Leu |
| 145 | | | | | 150 | | | | | 155 | | | | | 160 |
| Asn | Lys | Arg | His | His | Asn | Val | Asp | Glu | Leu | Arg | His | Glu | His | Gly | Arg |
| | | | | 165 | | | | | 170 | | | | | 175 | |
| Arg | Leu | Trp | Phe | Asp | Val | Ser | Asn | Val | Pro | Asn | Asp | Asn | Tyr | Leu | Val |
| | | | 180 | | | | | 185 | | | | | 190 | | |
| Met | Ala | Glu | Leu | Arg | Ile | Tyr | Gln | Asn | Ala | Asn | Glu | Gly | Lys | Trp | Leu |
| | | 195 | | | | | 200 | | | | | 205 | | | |
| Thr | Ala | Asn | Arg | Glu | Phe | Thr | Ile | Thr | Val | Tyr | Ala | Ile | Gly | Thr | Gly |
| | 210 | | | | | 215 | | | | | 220 | | | | |
| Thr | Leu | Gly | Gln | His | Thr | Met | Glu | Pro | Leu | Ser | Ser | Val | Asn | Thr | Thr |
| 225 | | | | | 230 | | | | | 235 | | | | | 240 |
| Gly | Asp | Tyr | Val | Gly | Trp | Leu | Glu | Leu | Asn | Val | Thr | Glu | Gly | Leu | His |
| | | | | 245 | | | | | 250 | | | | | 255 | |

-continued

```
Glu  Trp  Leu  Val  Lys  Ser  Lys  Asp  Asn  His  Gly  Ile  Tyr  Ile  Gly  Ala
               260                 265                     270

His  Ala  Val  Asn  Arg  Pro  Asp  Arg  Glu  Val  Lys  Leu  Asp  Asp  Ile  Gly
          275                 280                          285

Leu  Ile  His  Arg  Lys  Val  Asp  Asp  Glu  Phe  Gln  Pro  Phe  Met  Ile  Gly
          290                 295                     300

Phe  Phe  Arg  Gly  Pro  Glu  Leu  Ile  Lys  Ala  Thr  Ala  His  Ser  Ser  His
305                 310                 315                               320

His  Arg  Ser  Lys  Arg  Ser  Ala  Ser  His  Pro  Arg  Lys  Arg  Lys  Lys  Ser
                    325                 330                          335

Val  Ser  Pro  Asn  Asn  Val  Pro  Leu  Leu  Glu  Pro  Met  Glu  Ser  Thr  Arg
               340                      345                     350

Ser  Cys  Gln  Met  Gln  Thr  Leu  Tyr  Ile  Asp  Phe  Lys  Asp  Leu  Gly  Trp
               355                 360                     365

His  Asp  Trp  Ile  Ile  Ala  Pro  Glu  Gly  Tyr  Gly  Ala  Phe  Tyr  Cys  Ser
     370                      375                     380

Gly  Glu  Cys  Asn  Phe  Pro  Leu  Asn  Ala  His  Met  Asn  Ala  Thr  Asn  His
385                      390                 395                          400

Ala  Ile  Val  Gln  Thr  Leu  Val  His  Leu  Leu  Glu  Pro  Lys  Lys  Val  Pro
                    405                      410                     415

Lys  Pro  Cys  Cys  Ala  Pro  Thr  Arg  Leu  Gly  Ala  Leu  Pro  Val  Leu  Tyr
               420                      425                     430

His  Leu  Asn  Asp  Glu  Asn  Val  Asn  Leu  Lys  Lys  Tyr  Arg  Asn  Met  Ile
          435                      440                     445

Val  Lys  Ser  Cys  Gly  Cys  His
450                      455
```

( 2 ) INFORMATION FOR SEQ ID NO:26:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..104
        ( D ) OTHER INFORMATION: /label=BMP3

( x i ) SEQUENCE DESCRIPTION: SEQ ID NO:26:

```
Cys  Ala  Arg  Arg  Tyr  Leu  Lys  Val  Asp  Phe  Ala  Asp  Ile  Gly  Trp  Ser
1              5                    10                      15

Glu  Trp  Ile  Ile  Ser  Pro  Lys  Ser  Phe  Asp  Ala  Tyr  Tyr  Cys  Ser  Gly
               20                 25                      30

Ala  Cys  Gln  Phe  Pro  Met  Pro  Lys  Ser  Leu  Lys  Pro  Ser  Asn  His  Ala
          35                 40                      45

Thr  Ile  Gln  Ser  Ile  Val  Ala  Arg  Ala  Val  Gly  Val  Val  Pro  Gly  Ile
     50                      55                 60

Pro  Glu  Pro  Cys  Cys  Val  Pro  Glu  Lys  Met  Ser  Ser  Leu  Ser  Ile  Leu
65                      70                 75                           80

Phe  Phe  Asp  Glu  Asn  Lys  Asn  Val  Val  Leu  Lys  Val  Tyr  Pro  Asn  Met
               85                      90                      95

Thr  Val  Glu  Ser  Cys  Ala  Cys  Arg
               100
```

( 2 ) INFORMATION FOR SEQ ID NO:27:

( i ) SEQUENCE CHARACTERISTICS:
   ( A ) LENGTH: 102 amino acids
   ( B ) TYPE: amino acid
   ( C ) STRANDEDNESS: single
   ( D ) TOPOLOGY: linear ( i i ) MOLECULE TYPE: protein ( i x ) FEATURE:
   ( A ) NAME/KEY: Protein
   ( B ) LOCATION: 1..102
   ( D ) OTHER INFORMATION: /label=BMP5

( x i ) SEQUENCE DESCRIPTION: SEQ ID NO:27:

```
Cys Lys Lys His Glu Leu Tyr Val Ser Phe Arg Asp Leu Gly Trp Gln
  1               5                  10                  15
Asp Trp Ile Ile Ala Pro Glu Gly Tyr Ala Ala Phe Tyr Cys Asp Gly
               20                  25                  30
Glu Cys Ser Phe Pro Leu Asn Ala His Met Asn Ala Thr Asn His Ala
           35                  40                  45
Ile Val Gln Thr Leu Val His Leu Met Phe Pro Asp His Val Pro Lys
       50                  55                  60
Pro Cys Cys Ala Pro Thr Lys Leu Asn Ala Ile Ser Val Leu Tyr Phe
 65                  70                  75                  80
Asp Asp Ser Ser Asn Val Ile Leu Lys Lys Tyr Arg Asn Met Val Val
                 85                  90                  95
Arg Ser Cys Gly Cys His
               100
```

( 2 ) INFORMATION FOR SEQ ID NO:28:

( i ) SEQUENCE CHARACTERISTICS:
   ( A ) LENGTH: 102 amino acids
   ( B ) TYPE: amino acid
   ( C ) STRANDEDNESS: single
   ( D ) TOPOLOGY: linear ( i i ) MOLECULE TYPE: protein ( i x ) FEATURE:
   ( A ) NAME/KEY: Protein
   ( B ) LOCATION: 1..102
   ( D ) OTHER INFORMATION: /label=BMP6

( x i ) SEQUENCE DESCRIPTION: SEQ ID NO:28:

```
Cys Arg Lys His Glu Leu Tyr Val Ser Phe Gln Asp Leu Gly Trp Gln
  1               5                  10                  15
Asp Trp Ile Ile Ala Pro Lys Gly Tyr Ala Ala Asn Tyr Cys Asp Gly
               20                  25                  30
Glu Cys Ser Phe Pro Leu Asn Ala His Met Asn Ala Thr Asn His Ala
           35                  40                  45
Ile Val Gln Thr Leu Val His Leu Met Asn Pro Glu Tyr Val Pro Lys
       50                  55                  60
Pro Cys Cys Ala Pro Thr Lys Leu Asn Ala Ile Ser Val Leu Tyr Phe
 65                  70                  75                  80
Asp Asp Asn Ser Asn Val Ile Leu Lys Lys Tyr Arg Trp Met Val Val
                 85                  90                  95
Arg Ala Cys Gly Cys His
               100
```

( 2 ) INFORMATION FOR SEQ ID NO:29:

( i ) SEQUENCE CHARACTERISTICS:

( A ) LENGTH: 102 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..102
( D ) OTHER INFORMATION: /label=OPX
/ note= "WHEREIN XAA AT EACH POS'N IS INDEPENDENTLY
SELECTED FROM THE RESIDUES OCCURING AT THE
CORRESPONDING POS'N IN THE C-TERMINAL SEQUENCE OF MOUSE
OR HUMAN OP1 OR OP2 (SEQ. ID NOS. 5,6,7&8 OR 16,18,
20&22"

( x i ) SEQUENCE DESCRIPTION: SEQ ID NO:29:

| Cys | Xaa | Xaa | His | Glu | Leu | Tyr | Val | Xaa | Phe | Xaa | Asp | Leu | Gly | Trp | Xaa |
|---|---|---|---|---|---|---|---|---|---|---|---|---|---|---|---|
| 1 | | | | 5 | | | | | 10 | | | | | 15 | |
| Asp | Trp | Xaa | Ile | Ala | Pro | Xaa | Gly | Tyr | Xaa | Ala | Tyr | Tyr | Cys | Glu | Gly |
| | | | 20 | | | | 25 | | | | | 30 | | | |
| Glu | Cys | Xaa | Phe | Pro | Leu | Xaa | Ser | Xaa | Met | Asn | Ala | Thr | Asn | His | Ala |
| | | 35 | | | | 40 | | | | | 45 | | | | |
| Ile | Xaa | Gln | Xaa | Leu | Val | His | Xaa | Xaa | Xaa | Pro | Xaa | Xaa | Val | Pro | Lys |
| | 50 | | | | | 55 | | | | | 60 | | | | |
| Xaa | Cys | Cys | Ala | Pro | Thr | Xaa | Leu | Xaa | Ala | Xaa | Ser | Val | Leu | Tyr | Xaa |
| 65 | | | | | 70 | | | | | 75 | | | | | 80 |
| Asp | Xaa | Ser | Xaa | Asn | Val | Xaa | Leu | Xaa | Lys | Xaa | Arg | Asn | Met | Val | Val |
| | | | | 85 | | | | | 90 | | | | | 95 | |
| Xaa | Ala | Cys | Gly | Cys | His | | | | | | | | | | |
| | | | 100 | | | | | | | | | | | | |

( 2 ) INFORMATION FOR SEQ ID NO:30:

( i ) SEQUENCE CHARACTERISTICS:
( A ) LENGTH: 97 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..97
( D ) OTHER INFORMATION: /label=GENERIC-SEQ-5
/ note= "WHEREIN EACH XAA IS INDEPENDENTLY SELECTED FROM
A GROUP OF ONE OR MORE SPECIFIED AMINO ACIDS AS DEFINED
IN THE SPECIFICATION"

( x i ) SEQUENCE DESCRIPTION: SEQ ID NO:30:

| Leu | Xaa | Xaa | Xaa | Phe | Xaa | Xaa | Xaa | Gly | Trp | Xaa | Xaa | Trp | Xaa | Xaa | Xaa |
|---|---|---|---|---|---|---|---|---|---|---|---|---|---|---|---|
| 1 | | | | 5 | | | | | 10 | | | | | 15 | |
| Pro | Xaa | Xaa | Xaa | Xaa | Ala | Xaa | Tyr | Cys | Xaa | Gly | Xaa | Cys | Xaa | Xaa | Pro |
| | | | 20 | | | | 25 | | | | | 30 | | | |
| Xaa | Xaa | Xaa | Xaa | Xaa | Xaa | Xaa | Xaa | Asn | His | Ala | Xaa | Xaa | Xaa | Xaa | Xaa |
| | | 35 | | | | 40 | | | | | 45 | | | | |
| Xaa | Xaa | Xaa | Xaa | Xaa | Xaa | Xaa | Xaa | Xaa | Xaa | Xaa | Xaa | Cys | Cys | Xaa | Pro |
| | 50 | | | | | 55 | | | | | 60 | | | | |
| Xaa | Xaa | Xaa | Xaa | Xaa | Xaa | Xaa | Leu | Xaa | Xaa | Xaa | Xaa | Xaa | Xaa | Xaa | Xaa |
| 65 | | | | | 70 | | | | | 75 | | | | | 80 |
| Val | Xaa | Leu | Xaa | Xaa | Xaa | Xaa | Xaa | Met | Xaa | Val | Xaa | Xaa | Cys | Xaa | Cys |
| | | | | 85 | | | | | 90 | | | | | 95 | |
| Xaa | | | | | | | | | | | | | | | |

( 2 ) INFORMATION FOR SEQ ID NO:31:

( i ) SEQUENCE CHARACTERISTICS:
        ( A ) LENGTH: 102 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..102
        ( D ) OTHER INFORMATION: /label=GENERIC-SEQ-6
            / note= "WHEREIN EACH XAA IS INDEPENDENTLY SELECTED FROM A
            GROUP OF ONE OR MORE SPECIFIED AMINO ACIDS AS DEFINED IN
            THE SPECIFICATION"

( x i ) SEQUENCE DESCRIPTION: SEQ ID NO:31:

```
Cys Xaa Xaa Xaa Xaa Leu Xaa Xaa Xaa Phe Xaa Xaa Xaa Gly Trp Xaa
 1           5                    10                     15

Xaa Trp Xaa Xaa Xaa Pro Xaa Xaa Xaa Xaa Ala Xaa Tyr Cys Xaa Gly
            20                   25                  30

Xaa Cys Xaa Xaa Pro Xaa Xaa Xaa Xaa Xaa Xaa Xaa Xaa Asn His Ala
        35                   40                  45

Xaa Xaa Xaa Xaa Xaa Xaa Xaa Xaa Xaa Xaa Xaa Xaa Xaa Xaa Xaa Xaa
 50                       55                  60

Xaa Cys Cys Xaa Pro Xaa Xaa Xaa Xaa Xaa Xaa Xaa Xaa Leu Xaa Xaa
 65              70                  75                      80

Xaa Xaa Xaa Xaa Xaa Val Xaa Leu Xaa Xaa Xaa Xaa Xaa Met Xaa Val
            85                   90                  95

Xaa Xaa Cys Xaa Cys Xaa
           100
```

( 2 ) INFORMATION FOR SEQ ID NO:32:

( i ) SEQUENCE CHARACTERISTICS:
        ( A ) LENGTH: 1247 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 84..1199
        ( D ) OTHER INFORMATION: /product="GDF-1"

( x i ) SEQUENCE DESCRIPTION: SEQ ID NO:32:

```
GGGGACACCG GCCCCGCCCT CAGCCCACTG GTCCCGGGCC GCCGCGGACC CTGCGCACTC          60

TCTGGTCATC GCCTGGGAGG AAG ATG CCA CCG CCG CAG CAA GGT CCC TGC            110
                         Met Pro Pro Pro Gln Gln Gly Pro Cys
                          1               5

GGC CAC CAC CTC CTC CTC CTC CTG GCC CTG CTG CTG CCC TCG CTG CCC          158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG          206
Leu Thr Arg Ala Pro Val Pro Pro Gly Pro Ala Ala Ala Leu Leu Gln
            30                  35                  40

GCT CTA GGA CTG CGC GAT GAG CCC CAG GGT GCC CCC AGG CTC CGG CCG          254
Ala Leu Gly Leu Arg Asp Glu Pro Gln Gly Ala Pro Arg Leu Arg Pro
        45                  50                  55

GTT CCC CCG GTC ATG TGG CGC CTG TTT CGA CGC CGG GAC CCC CAG GAG          302
```

```
            Val Pro Pro Val Met Trp Arg Leu Phe Arg Arg Arg Asp Pro Gln Glu
                    60              65                  70

ACC AGG TCT GGC TCG CGG CGG ACG TCC CCA GGG GTC ACC CTG CAA CCG        350
Thr Arg Ser Gly Ser Arg Arg Thr Ser Pro Gly Val Thr Leu Gln Pro
    75              80                  85

TGC CAC GTG GAG GAG CTG GGG GTC GCC GGA AAC ATC GTG CGC CAC ATC        398
Cys His Val Glu Glu Leu Gly Val Ala Gly Asn Ile Val Arg His Ile
90              95                  100                 105

CCG GAC CGC GGT GCG CCC ACC CGG GCC TCG GAG CCT GTC TCG GCC GCG        446
Pro Asp Arg Gly Ala Pro Thr Arg Ala Ser Glu Pro Val Ser Ala Ala
                110                 115                 120

GGG CAT TGC CCT GAG TGG ACA GTC GTC TTC GAC CTG TCG GCT GTG GAA        494
Gly His Cys Pro Glu Trp Thr Val Val Phe Asp Leu Ser Ala Val Glu
            125                 130                 135

CCC GCT GAG CGC CCG AGC CGG GCC CGC CTG GAG CTG CGT TTC GCG GCG        542
Pro Ala Glu Arg Pro Ser Arg Ala Arg Leu Glu Leu Arg Phe Ala Ala
        140                 145                 150

GCG GCG GCG GCA GCC CCG GAG GGC GGC TGG GAG CTG AGC GTG GCG CAA        590
Ala Ala Ala Ala Ala Pro Glu Gly Gly Trp Glu Leu Ser Val Ala Gln
    155                 160                 165

GCG GGC CAG GGC GCG GGC GCG GAC CCC GGG CCG GTG CTG CTC CGC CAG        638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC        686
Leu Val Pro Ala Leu Gly Pro Pro Val Arg Ala Glu Leu Leu Gly Ala
                190                 195                 200

GCT TGG GCT CGC AAC GCC TCA TGG CCG CGC AGC CTC CGC CTG GCG CTG        734
Ala Trp Ala Arg Asn Ala Ser Trp Pro Arg Ser Leu Arg Leu Ala Leu
            205                 210                 215

GCG CTA CGC CCC CGG GCC CCT GCC GCC TGC GCG CGC CTG GCC GAG GCC        782
Ala Leu Arg Pro Arg Ala Pro Ala Ala Cys Ala Arg Leu Ala Glu Ala
        220                 225                 230

TCG CTG CTG CTG GTG ACC CTC GAC CCG CGC CTG TGC CAC CCC CTG GCC        830
Ser Leu Leu Leu Val Thr Leu Asp Pro Arg Leu Cys His Pro Leu Ala
    235                 240                 245

CGG CCG CGG CGC GAC GCC GAA CCC GTG TTG GGC GGC GGC CCC GGG GGC        878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG        926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG        974
His Arg Trp Val Ile Ala Pro Arg Gly Phe Leu Ala Asn Tyr Cys Gln
            285                 290                 295

GGT CAG TGC GCG CTG CCC GTC GCG CTG TCG GGG TCC GGG GGG CCG CCG       1022
Gly Gln Cys Ala Leu Pro Val Ala Leu Ser Gly Ser Gly Gly Pro Pro
        300                 305                 310

GCG CTC AAC CAC GCT GTG CTG CGC GCG CTC ATG CAC GCG GCC GCC CCG       1070
Ala Leu Asn His Ala Val Leu Arg Ala Leu Met His Ala Ala Ala Pro
    315                 320                 325

GGA GCC GCC GAC CTG CCC TGC TGC GTG CCC GCG CGC CTG TCG CCC ATC       1118
Gly Ala Ala Asp Leu Pro Cys Cys Val Pro Ala Arg Leu Ser Pro Ile
330                 335                 340                 345

TCC GTG CTC TTC TTT GAC AAC AGC GAC AAC GTG GTG CTG CGG CAG TAT       1166
Ser Val Leu Phe Phe Asp Asn Ser Asp Asn Val Val Leu Arg Gln Tyr
                350                 355                 360

GAG GAC ATG GTG GTG GAC GAG TGC GGC TGC CGC TAACCCGGGG CGGGCAGGGA    1219
Glu Asp Met Val Val Asp Glu Cys Gly Cys Arg
            365                 370

CCCGGGCCCA ACAATAAATG CCGCGTGG                                        1247
```

(2) INFORMATION FOR SEQ ID NO:33:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:33:

```
Met Pro Pro Pro Gln Gln Gly Pro Cys Gly His His Leu Leu Leu Leu
 1               5                  10                  15
Leu Ala Leu Leu Leu Pro Ser Leu Pro Leu Thr Arg Ala Pro Val Pro
             20                  25                  30
Pro Gly Pro Ala Ala Ala Leu Leu Gln Ala Leu Gly Leu Arg Asp Glu
         35                  40                  45
Pro Gln Gly Ala Pro Arg Leu Arg Pro Val Pro Val Met Trp Arg
     50                  55                  60
Leu Phe Arg Arg Arg Asp Pro Gln Glu Thr Arg Ser Gly Ser Arg Arg
 65                  70                  75                  80
Thr Ser Pro Gly Val Thr Leu Gln Pro Cys His Val Glu Glu Leu Gly
                 85                  90                  95
Val Ala Gly Asn Ile Val Arg His Ile Pro Asp Arg Gly Ala Pro Thr
             100                 105                 110
Arg Ala Ser Glu Pro Val Ser Ala Ala Gly His Cys Pro Glu Trp Thr
             115                 120                 125
Val Val Phe Asp Leu Ser Ala Val Glu Pro Ala Glu Arg Pro Ser Arg
 130                 135                 140
Ala Arg Leu Glu Leu Arg Phe Ala Ala Ala Ala Ala Ala Ala Pro Glu
145                 150                 155                 160
Gly Gly Trp Glu Leu Ser Val Ala Gln Ala Gly Gln Gly Ala Gly Ala
                 165                 170                 175
Asp Pro Gly Pro Val Leu Leu Arg Gln Leu Val Pro Ala Leu Gly Pro
             180                 185                 190
Pro Val Arg Ala Glu Leu Leu Gly Ala Ala Trp Ala Arg Asn Ala Ser
         195                 200                 205
Trp Pro Arg Ser Leu Arg Leu Ala Leu Ala Leu Arg Pro Arg Ala Pro
 210                 215                 220
Ala Ala Cys Ala Arg Leu Ala Glu Ala Ser Leu Leu Leu Val Thr Leu
225                 230                 235                 240
Asp Pro Arg Leu Cys His Pro Leu Ala Arg Pro Arg Arg Asp Ala Glu
             245                 250                 255
Pro Val Leu Gly Gly Gly Pro Gly Gly Ala Cys Arg Ala Arg Arg Leu
         260                 265                 270
Tyr Val Ser Phe Arg Glu Val Gly Trp His Arg Trp Val Ile Ala Pro
             275                 280                 285
Arg Gly Phe Leu Ala Asn Tyr Cys Gln Gly Gln Cys Ala Leu Pro Val
     290                 295                 300
Ala Leu Ser Gly Ser Gly Gly Pro Pro Ala Leu Asn His Ala Val Leu
305                 310                 315                 320
Arg Ala Leu Met His Ala Ala Ala Pro Gly Ala Ala Asp Leu Pro Cys
                 325                 330                 335
Cys Val Pro Ala Arg Leu Ser Pro Ile Ser Val Leu Phe Phe Asp Asn
             340                 345                 350
Ser Asp Asn Val Val Leu Arg Gln Tyr Glu Asp Met Val Val Asp Glu
```

```
355           360           365
Cys Gly Cys Arg
    370
```

METHOD OF DIAGNOSING RENAL TISSUE DAMAGE OR DISEASE

This patent application is a continuation of U.S. Ser. No. 08/278,729, filed Jul. 20, 1994, now U.S. Pat. No. 5,650,276 which is a continuation of U.S. Ser. No. 07/938,021, filed Aug. 28, 1992, abandoned, which is a continuation-in-part of U.S. Ser. No. 07/752,861, filed Aug. 30, 1991, abandoned which is a continuation-in-part of U.S. Ser. No. 07/667,274, filed Mar. 11, 1991, abandoned.

The invention relates to a method of screening drugs for the ability to modulate the level in mammals of proteins which can induce tissue morphogenesis and to methods of determining which animal tissue(s) and/or cell types within a tissue express a particular morphogenic protein.

BACKGROUND OF THE INVENTION

Cell differentiation is the central characteristic of morphogenesis which initiates in the embryo, and continues to various degrees throughout the life of an organism in adult tissue repair and regeneration mechanisms. Members of the TGF-β superfamily include subfamilies of highly-related genes that now are suspected to play important roles in cell differentiation and morphogenesis during development and/ or during adult life. For example, the Drosophila decapentaplegic gene product (DPP) has been implicated in formation of the dorsal-ventral axis in fruit flies; activins induce mesoderm and anterior structure formation in mammals; M üllerian inhibiting substance (MIS) may be required for male sex development in mammals; growth/differentiation factor-1 (GDF-1) has been implicated in nerve development and maintenance; other morphogenic proteins (BMP-2, -3, -4 and OP-1) induce bone formation.

The development and study of a bone induction model system has identified the developmental cascade of bone differentiation as consisting of chemotaxis of mesenchymal cells, proliferation of these progenitor cells, differentiation of cartilage, ossification and hypertrophy of this cartilaginous tissue, vascular invasion, bone formation, remodeling, and finally, marrow differentiation (Reddi (1981) Collagen Rel. Res. 1:209–206). This bone model system, which is studied in adult mammals, recapitulates the cascade of bone differentiation events that occur in formation of bone in the developing fetus. In other studies, the epithelium of the urinary bladder has been shown to induce new bone formation. Huggins (1931, Arch. Surg. 22:377–408) showed that new bone formation could be induced by surgical transplantation of urinary bladder epithelium onto the parietal fascia. Urist (1965, Science 150:893–899) demonstrated that implantation of demineralized bone segments resulted in endochondral bone formation. The latter study and observation suggested the existence of an osteogenic protein and that bovine diaphyseal bone was a source of enriched preparations of osteogenic protein (Sampath et al., J. Biol. Chem. 265:13198–13205, 1990; Urist, ibid; Reddi et al., Proc. Nat. Aca. Sci. 69:1601–1605, 1972; Sampath et al., Proc. Natl. Acad. Sci. 80:6591–6595, 1983). Proteins capable of inducing endochondral bone formation in mammals when implanted in association with a matrix now have been identified in a number of different mammalian species, as have the genes encoding these proteins, (see, for example, U.S. Pat. No. 4,968,590; U.S. Ser. No. 315,342 filed Feb. 23, 1989; and U.S. Ser. No. 599,543, filed Oct. 18, 1990). Human OP-1 DNA has been cloned from various cDNA and genomic libraries using a consensus probe (Ozkaynak et al., EMBO J. 9:2085–2093, 1990). Purified human recombinant OP-1, expressed in mammalian cells, has been shown to induce new bone formation in vivo. Like other members of the TGF-β superfamily, OP-1 is produced as a precursor, glycosylated, processed and secreted as a mature dimer. Mature OP-1 is cleaved at a maturation site following a sequence with the pattern of RXXR (Panganiban et al., Mol. Cell. Biol. 10:2669–2677, 1990).

The degree of morphogenesis in adult tissue varies among different tissues and depends on, among other factors, the degree of cell turnover in a given tissue. On this basis, tissues can be divided into three broad categories: 1) tissues with static cell populations such as nerve and skeletal muscle where there is little or no cell division and most of the cells formed during development persist throughout adult life and, therefore, possess little or no ability for normal regeneration after injury; 2) tissues containing conditionally renewing populations such as liver where there is generally little cell division but, in response to an appropriate stimulus or injury, cells can divide to produce daughters of the same differentiated cell type; and 3) tissues with permanently renewing populations including blood, bone, testes, and stratified squamous epithelia which are characterized by rapid and continuous cell turnover in the adult. Here, the terminally differentiated cells have a short life span and are replaced through proliferation of a distinct subpopulation of cells, known as stem or progenitor cells.

It is an object of this invention to provide a method of screening compounds which, when administered to a given tissue from a given organism, cause an alteration in the level of morphogenic protein ("morphogen") produced by the tissue. Such compounds, when administered systemically, will result in altered systemic or local levels of morphogenic activity. This morphogenic activity includes the ability to induce proliferation and sequential differentiation of progenitor cells, and the ability to support and maintain the differentiated phenotype or sequence of phenotypes through the progression of events that results in the formation of normal adult tissue (including organ regeneration). Thus, broadly, the invention provides a key to development of additional modalities of therapies involving modulation of morphogenic protein production in animals or adult mammals, e.g., humans, and consequent correction of conditions involving pathologic alteration of the balance of tissue cell turnover. Another object of the invention is to provide methodologies for identifying or selecting a combination of compound(s) which may increase a progenitor cell population in a mammal, stimulate progenitor cells to differentiate in vivo or in vitro, maintain the differentiated phenotype or sequence of phenotypes of a tissue, induce tissue-specific growth in vivo, or replace diseased or damaged tissues or organs in vivo. Another object of the invention is to determine the tissue(s) or organ(s) of origin of a given morphogen. Another object of the invention is to determine the specific cell type(s) within the tissue(s) or organ(s) of origin, or cell line(s) derived from the tissue(s), or organ(s) of origin, that is responsible for the synthesis and production of a given morphogen. These and other objects and features of the invention will be apparent from the description, drawing, and claims which follow.

SUMMARY OF THE INVENTION

In one aspect, the present invention provides a method of diagnosing renal tissue damage or disease by measuring endogenous expression of OP-1 by renal tissue of a mammal (e.g., a human). A depression of endogenous expression relative to undamaged or undiseased mammalian renal tissue indicates a diagnosis that the mammal is afflicted with renal tissue damage or disease (e.g., renal tissue degeneration or kidney disease). Endogenous OP-1 expression may be measured by detecting OP-1 mRNA or protein in the renal tissue of the mammal, or OP-1 protein circulating in the mammal. For example, OP-1 mRNA may be detected using a nucleic acid probe that hybridizes specifically with RNA transcribed from an OP-1 gene, and OP-1 protein may be detected using an antibody specific for OP-1 protein.

The invention also features a method of screening candidate compounds for the ability to modulate the effective local or systemic concentration or level of morphogenic protein in an organism. The method is practiced by incubating one or more candidate compound(s) with cells from a test tissue type of an organism known to produce a given morphogen for a time sufficient to allow the compound(s) to affect the production, i.e., expression and/or secretion, of morphogen by the cells; and then assaying cells and the medium conditioned by the cells for a change in a parameter indicative of the level of production of the morphogenic protein. The procedure may be used to identify compounds showing promise as drugs for human use capable of increasing or decreasing morphogen production in vivo, thereby to correct or alleviate a diseased condition.

In a related aspect, the invention features a method of screening tissue(s) of an organism to assess whether or at what level cells of the tissue(s) produce a particular morphogen, thereby to determine a tissue(s) of origin of the morphogen. This permits selection of the tissue cell type to be used in the screening. As used herein, "tissue" refers to a group of cells which are naturally found associated, including an organ.

As an example of tissue(s) or organ(s) which produce high levels of morphogen relative to the level produced by other types of tissues, it has been discovered that OP-1, first found in bone tissue is produced at relatively high levels in cells derived from renal, e.g., kidney or bladder, or adrenal tissue; that GDF-1 is produced at relatively high levels in cells derived from nerve, e.g., brain tissue; that DPP is produced at relatively high levels in cells derived from one of the following drosophila tissues: dorsal ectoderm, epithelial imaginal disc, visceral mesoderm, or gut endoderm; that Vgr-1 is produced at relatively high levels in cells derived from mouse lung tissue; and that Vgl is produced at relatively high levels in cells derived from xenopus fetal endoderm tissue. In addition, BMP3 and CBMP2B transcripts have been identified in abundance in lung tissue. As used herein, "derived" means the cells are the cultured tissue itself, or are a cell line whose parent cells are the tissue itself.

Preferred methods for determining the level of or a change in the level of a morphogen in a cultured cell include using an antibody specific for the morphogen, e.g., in an immunoassay such as an ELISA or radioimmunoassay; and determining the level of nucleic acid, most particularly mRNA, encoding the morphogen using a nucleic acid probe that hybridizes under stringent conditions with the morphogen RNA, such as in an RNA dot blot analysis. Where a change in the presence and/or concentration of morphogen is being determined, it will be necessary to measure and compare the levels of morphogen in the presence and absence of the candidate compound. The nucleic acid probe may be a nucleotide sequence encoding the morphogen or a fragment large enough to hybridize specifically only to RNA encoding a specific morphogen under stringent conditions. As used herein, "stringent conditions" are defined as conditions in which non-specific hybrids will be eluted but at which specific hybrids will be maintained, i.e., incubation at 0.1×SSC (15 mM NaCl, 5 mM Na citrate) at 50° C. for 15 minutes.

Examples of morphogens whose levels may be determined according to the invention include OP-1, OP-2, GDF-1, Vgr-1, DPP, 60A, CBMP2A, CBMP2B, BMP 2, 3, 4, 5, 6, or Vgl. Thus, if an immunoassay is used to indicate the presence and/or concentration of a morphogen, an antibody specific for one of these morphogens only, and which will not detect the presence of other morphogens, will be used. Similarly, if nucleic acid hybridization is used to indicate the level of RNA encoding the morphogen, a nucleotide probe specific for one of these morphogens only will be used under hybridization conditions such that the probe should not be capable of hybridizing with RNA encoding a different morphogen. A morphogen includes an active C-terminal core region, which includes at least six cysteine residues, and a region N-terminal to the C-terminal region that is relatively non-homologous to the equivalent N-terminal regions of other morphogens. In addition, the 3' noncoding region of the mRNA is unique to each morphogen. Thus, a nucleic acid probe encoding all or a portion of the sequences N-terminal to the C-terminal core region of a morphogen, or encoding all or a portion of the sequences C-terminal to or 3' to the core region of a morphogen may be used as a probe which detects mRNA encoding that morphogen only.

"Morphogenic proteins" or "morphogens", as used herein, include naturally-occurring osteogenic proteins capable of inducing the full developmental cascade of bone formation, as well as polypeptide chains not normally associated with bone or bone formation, but sharing substantial sequence homology with osteogenic proteins. Such proteins, as well as DNA sequences encoding them, have been isolated and characterized for a number of different species. See, for example, U.S. Pat. No. 4,968,590 and U.S. Pat. No. 5,011,691, U.S. application Ser. Nos. 1989; 422,699, filed Oct. 17, 1989, and 600,024 and 599,543, both filed Oct. 18, 1990; Sampath et al., (1990) J. Biol. Chem. 265:13198–13205; Ozkaynak et al. (1990) EMBO J. 9:2085–2093; and Lee, Proc. Nat. Aca. Sci. 88:4250–4254 (1991), all of which are hereby incorporated by reference. Many of these proteins subsequently were discovered to have utility beyond bone morphogenesis. See, e.g., U.S. Ser. No. 667,274 filed Mar. 11, 1991. The mature forms of morphogens share substantial amino acid sequence homology, especially in the C-terminal core regions of the proteins. In particular, most of the proteins share a seven-cysteine skeleton in this region, in addition to other apparently required amino acids. Table II, infra, shows the amino acid sequence homologies for nine morphogens over the carboxy terminal 102 amino acids.

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) PNAS 88:4250–4254), all of which are presented in Table II and Seq. ID Nos. 5–14), and the recently identified 60A protein (from Drosophila, Seq. ID No. 24, see Wharton et al. (1991) PNAS 88:9214–9218.) The members of this family, which include members of the TGF-β superfamily of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) Nucleic Acids Research 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | refers generically to the group of morphogenically active proteins expressed from part or all of a DNA sequence encoding OP-1 protein, including allelic and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293-431 (hOP1) and 292-430 (mOP1). The "pro" regions of the proteins, cleaved to yield the mature, morphogenically active proteins are defined essentially by residues 30-292 (hOP1) and residues 30-291 (mOP1). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264-402 (hOP2) and 261-399 (mOP2). The "pro" regions of the proteins, cleaved to yield the mature, morphogenically active proteins likely are defined essentially by residues 18-263 (hOP2) and residues 18-260 (mOP2). (Another cleavage site also occurs 21 residues upstream for both OP-2 proteins.) |
| "CBMP2" | refers generically to the morphogenically active proteins expressed from a part or all of a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) Science 242:1528-1534. The pro domain for BMP2 (BMP2A) likely includes residues 25-248 or 25-282; the mature protein, residues 249-396 or 283-396. The pro domain for BMP4 (BMP2B) likely includes residues 25-256 or 25-292; the mature protein, residues 257-408 or 293-408. |
| "DPP(fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81-84. The pro domain likely extends from the signal peptide cleavage site to residue 456; the mature protein likely is defined by residues 457-588. |

TABLE I-continued

| | |
|---|---|
| "Vgl(fx)" | refers to protein sequences encoded by the Xenopus Vgl gene and defining the conserved seven cysteine skeleton (Seq. ID No. 12). The amino acid sequence for the full length protein appears in Weeks (1987) Cell 51: 861-867. The pro domain likely extends from the signal peptide cleavage site to residue 246; the mature protein likely is defined by residues 247-360. |
| "Vgr-1(fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554-4558. The pro domain likely extends from the signal peptide cleavage site to residue 299; the mature protein likely is defined by residues 300-438. |
| "GDF-1(fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The pro domain likely extends from the signal peptide cleavage site to residue 214; the mature protein likely is defined by residues 215-372. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The pro domain likely extends from the signal peptide cleavage site to residue 324; the mature protein likely is defined by residues 325-455. |
| "BMP3(fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528-1534. The pro domain likely extends from the signal peptide cleavage site to residue 290; the mature protein likely is defined by residues 291-472. |
| "BMP5(fx)" | refers to protein sequences encoded by the human BMP5 gene and defining the conserved seven cysteine skeleton (Seq. ID No. 27). The amino acid sequence for the full length protein appears in Celeste, et al. (1991) PNAS 87: 9843-9847. The pro domain likely extends from the signal peptide cleavage site to residue 316; the mature protein likely is defined by residues 317-454. |
| "BMP6(fx)" | refers to protein sequences encoded by the human BMP6 gene and defining the conserved seven cysteine skeleton (Seq. ID No. 28). The amino acid sequence for the full length protein appear sin Celeste, et al. (1990) PNAS 87: 9843-5847. The pro domain likely includes extends from the signal peptide cleavage site to residue 374; the mature sequence likely includes residues 375-513. |

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention. Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- and inter-chain disulfide bonds such that the protein is capable of acting as a morphogen as defined herein. Specifically, the morphogens generally are capable of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

Morphogens useful in this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

Cys Xaa Xaa Xaa Xaa    (Seq. ID No. 15)
 1           5

Preferred amino acid sequences within the foregoing generic sequences include: Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 and 4 are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 or 4, respectively, providing an appropriate cysteine skeleton where inter- or intramolecular disulfide bonds can form, and contain certain critical amino acids which influence the tertiary structure of the proteins.

<u>Generic Sequence 3</u>

Leu Tyr Val Xaa Phe
 1           5

Xaa Xaa Xaa Gly Trp Xaa Xaa Trp Xaa
             10

Xaa Ala Pro Xaa Gly Xaa Xaa Ala
 15              20

Xaa Tyr Cys Xaa Gly Xaa Cys Xaa
         25              30

Xaa Pro Xaa Xaa Xaa Xaa
             35

Xaa Xaa Xaa Asn His Ala Xaa Xaa
         40                  45

Xaa Xaa Leu Xaa Xaa Xaa Xaa
             50

Xaa Xaa Xaa Xaa Xaa Xaa Cys
         55              60

Cys Xaa Pro Xaa Xaa Xaa Xaa
             65

Xaa Xaa Xaa Leu Xaa Xaa Xaa
 70                  75

Xaa Xaa Xaa Xaa Val Xaa Leu Xaa
             80

Xaa Xaa Xaa Xaa Met Xaa Val Xaa
 85                       90

Xaa Cys Gly Cys Xaa
         95 wherein each Xaa is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

<u>Generic Sequence 4</u>

```
Cys Xaa Xaa Xaa Xaa Leu Tyr Val Xaa Phe
 1               5                  10

Xaa Xaa Xaa Gly Trp Xaa Xaa Trp Xaa
                 15

Xaa Ala Pro Xaa Gly Xaa Xaa Ala
 20              25

Xaa Tyr Cys Xaa Gly Xaa Cys Xaa
         30              35

Xaa Pro Xaa Xaa Xaa Xaa
             40

Xaa Xaa Xaa Asn His Ala Xaa Xaa
         45              50

Xaa Xaa Leu Xaa Xaa Xaa Xaa
             55

Xaa Xaa Xaa Xaa Xaa Xaa Cys
 60                  65

Cys Xaa Pro Xaa Xaa Xaa Xaa
             70

Xaa Xaa Xaa Leu Xaa Xaa Xaa
 75                  80

Xaa Xaa Xaa Xaa Val Xaa Leu Xaa
                 85

Xaa Xaa Xaa Xaa Met Xaa Val Xaa
 90                  95

Xaa Cys Gly Cys Xaa
            100
``` wherein each Xaa is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser, His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75=(Ile, Thr or Val); Xaa at res.76=(Ser or Ala); Xaa at res.77=(Val or Met); Xaa at res.79=(Tyr or Phe);. Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16-17), mouse OP-1 (mOP-1, Seq. ID Nos. 6 and 18-19), human and mouse OP-2 (Seq. ID Nos. 7, 8, and 20-22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24-25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4, Generic Sequences 5 and 6 allow for an additional cysteine at position 41 (Generic Sequence 5) or position 46 (Generic Sequence 6), providing an appropriate cysteine skeleton where inter- or intramolecular disulfide bonds can form, and containing certain critical amino acids which influence the tertiary structure of the proteins.

<u>Generic Sequence 5</u>

```
Leu Xaa Xaa Xaa Phe
 1               5

Xaa Xaa Xaa Gly Trp Xaa Xaa Trp Xaa
                 10

Xaa Xaa Pro Xaa Xaa Xaa Ala
 15              20

Xaa Tyr Cys Xaa Gly Xaa Cys Xaa
         25              30

Xaa Pro Xaa Xaa Xaa Xaa
             35

Xaa Xaa Xaa Asn His Ala Xaa Xaa
         40              45

Xaa Xaa Xaa Xaa Xaa Xaa
             50

Xaa Xaa Xaa Xaa Xaa Xaa Cys
 55              60
```

-continued
Generic Sequence 5

```
Cys Xaa Pro Xaa Xaa Xaa Xaa
             65
Xaa Xaa Xaa Leu Xaa Xaa Xaa
 70               75
Xaa Xaa Xaa Xaa Val Xaa Leu Xaa
             80
Xaa Xaa Xaa Xaa Met Xaa Val Xaa
 85                  90
Xaa Cys Xaa Cys Xaa
     95
``` wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35= (Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53= (Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

Generic Sequence 6

```
Cys Xaa Xaa Xaa Xaa Leu Xaa Xaa Xaa Phe
 1               5                10
Xaa Xaa Xaa Gly Trp Xaa Xaa Trp Xaa
                 15
Xaa Xaa Pro Xaa Xaa Xaa Xaa Ala
 20               25
Xaa Tyr Cys Xaa Gly Xaa Cys Xaa
         30                 35
Xaa Pro Xaa Xaa Xaa Xaa Xaa
             40
Xaa Xaa Xaa Asn His Ala Xaa Xaa
         45              50
Xaa Xaa Xaa Xaa Xaa Xaa Xaa
             55
Xaa Xaa Xaa Xaa Xaa Xaa Cys
 60                      65
Cys Xaa Pro Xaa Xaa Xaa Xaa Xaa
             70
Xaa Xaa Xaa Leu Xaa Xaa Xaa
 75               80
Xaa Xaa Xaa Xaa Val Xaa Leu Xaa
             85
Xaa Xaa Xaa Xaa Met Xaa Val Xaa
 90                   95
Xaa Cys Xaa Cys Xaa
     100
``` wherein each Xaa is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16=(Gln, Leu, Asp, His, Asn or Ser); Xaa at res.17=(Asp, Arg, Asn or Glu); Xaa at res.19=(Ile or Val); Xaa at res.20=(Ile or Val); Xaa at res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40= (Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58= (Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr, or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayoff et al., *Atlas of Protein Sequence and Structure*; vol. 5, Suppl. 3, pp. 345–362, (M. O. Dayoff, ed., Nat'l BioMed. Research Fdn., Washington, D.C. 1979). As used herein, potentially useful sequences are aligned with a known morphogen sequence using the method of Needleman et al. ((1970) *J.Mol.Biol.* 48:443–453) and identities calculated by the Align program (DNAstar, Inc.). "Homology" or "similarity" as used herein includes allowed conservative changes as defined by Dayoff et al.

Morphogen sequences which are detectable according to the methods of the invention include but are not limited to those having greater than 60% identity, preferably greater than 65% identity, with the amino acid sequence defining the conserved six cysteine skeleton of hOP1 (e.g., residues 43–139 of Seq. ID No. 5) These most preferred sequences include both allelic and species variants of the OP-1 and OP-2 proteins, including the Drosophila 60A protein. Accordingly, morphogens which are detectable according to the invention include active proteins comprising species of polypeptide chains having the generic amino acid sequence herein referred to as "OPX", which accommodates the homologies between the various identified species of OP1 and OP2 (Seq. ID No. 29).

The morphogens detectable in the methods of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, chimetic variants containing a domain(s) or region(s) of one family member functionally arranged with another domain(s) or regions(s) of a second family member, as well as various truncated and fusion constructs. Deletion or insertion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include *E. coli* or mammalian cells, such as CHO, COS or BSC cells. A detailed description of the morphogens detectable according to the methods of this invention is disclosed in copending U.S. patent application Ser. Nos. 752,764, filed Aug. 30, 1991, and 667,274, filed Mar. 11, 1991, the disclosure of which are incorporated herein by reference.

The screening method of the invention provides a simple method of determining a change in the level of morphogenic protein as a result of exposure of cultured cells to one or more compound(s). The level of a morphogenic protein in a given cell culture, or a change in that level resulting from exposure to one or more compound(s) indicates that direct application of the compound modulates the level of the morphogen expressed by the cultured cells. If, for example, a compound upregulated the production of OP-1 by a kidney cell line, it would then be desirable to test systemic administration of this compound in an animal model to determine if it upregulated the production of OP-1 in vivo. If this compound did upregulate the endogenous circulating levels of OP-1, it would be consistent with administration of the compound systemically for the purpose of correcting bone metabolism diseases such as osteoporosis. The level of morphogen in the body may be a result of a wide range of physical conditions, e.g., tissue degeneration such as occurs in diseases including arthritis, emphysema, osteoporosis, kidney diseases, lung diseases, cardiomyopathy, and cirrhosis of the liver. The level of morphogens in the body may also occur as a result of the normal process of aging. A compound selected by the screening method of the invention as, for example, one which increases the level of morphogen in a tissue, may be consistent with the administration of the compound systemically or locally to a tissue for the purpose of preventing some form of tissue degeneration or for restoring the degenerated tissue to its normal healthy level.

Other advantages of the invention include determining the tissue or tissues of origin of a given morphogen in order to administer a compound aimed at modulating the systemic level of morphogen for treatment of a disease or condition in which the level of morphogen production has become altered.

DETAILED DESCRIPTION

Figure 1:
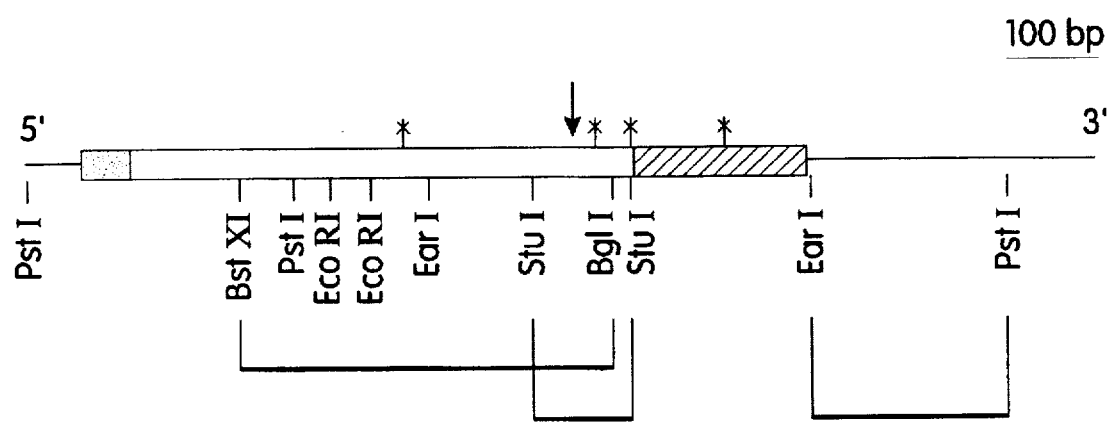
FIG. 1 shows the fragments of OP-1, used as probes in Northern hybridizations useful in the processes of the invention.

The invention is based on the discovery of a family of structurally related morphogenic proteins (BMPs), also called osteogenic proteins (OPs), and more particularly that various of these proteins play an important role, not only in embryogenesis, but also in tissue and organ maintenance and repair in juvenile and adult mammals. Morphogenic proteins which have been identified include BMP 2, 3, 4, 5, 6, OP-1 and OP-2 (murine and human), Vgr-1, Vgl, DPP, GDF-1, CMBP-2A, CMBP-2B, 60A, and the inhibin/activin class of proteins. Other recombinant proteins include COP1, COP3, COP4, COP5, COP7, and COP16. While, as explained herein, the morphogen have significant homologies and similarities in structure, it is hypothesized that variants within the morphogenic protein genes may have specific roles in specific tissue involving, for example, stimulation of progenitor cell multiplication, tissue specific or tissue preferred phenotype maintenance, and/or stimulation or modulation of the rate of differentiation, growth or replication of tissue cells characterized by high turnover. The effect on the long-term physiology, maintenance and repair of particular tissues by particular species of the morphogens is currently unknown in any significant detail. However, methods useful in determining which particular tissues express which particular morphogen(s), and for finding changes which stimulate or depress morphogen expression in vivo, would enable discovery and development of strategies for therapeutic treatment of a large number of diseased states, and provide drugs designed to implement the strategy.

This invention provides such methods and, more specifically, two generic processes for obtaining data which ultimately will permit determination of structure/activity relationships of specific naturally occurring mammalian morphogens and drugs capable of modulating their production. For example, using the assay of the invention, it has been determined that OP-1, first found in bone and demonstrated to be osteoinductive, is synthesized primarily in kidney, bladder, and adrenal tissue. This surprising discovery, coupled with the observation that patients with kidney disease often express loss of bone mass, suggests that the bone loss in these patients may be due to pathologic depression of OP-1 synthesis in kidney, and suggests that administration of OP-1 systemically or stimulation of OP-1 expression and secretion by the kidney may arrest bone loss, or effect remineralization through increased bone formation (i.e., osteogenesis).

There are two fundamental aspects of the invention. One aspect involves an assay to determine tissues and cell types capable of synthesis and secretion of the morphogens; the other involves the use of the identified cell types configured in a screening system to find substances useful therapeutically to modulate, i.e., stimulate or depress, morphogen expression and/or secretion.

The assay to determine the tissue of origin of a given morphogen involves screening a plurality (i.e., two or more) different tissues by determining a parameter indicative of production of a morphogen in the tissue, and comparing the parameters. The tissue(s) of origin will, of course, be the tissue that produces that morphogen.

The other assay of the invention involves screening candidate compounds for their ability to modulate the effective systemic or local concentration of a morphogen by incubating the compound with a cell culture that produces the morphogen, and assaying the culture for a parameter indicative of a change in the production level of the morphogen. Useful candidate compounds then may be tested for in vivo efficacy in a suitable animal model. These compounds then may be used in vivo to modulate effective morphogen concentrating in the disease treatment.

1. Morphogen Tissue Distribution

Morphogens are broadly distributed in developing and adult tissue. For example, DPP and 60A are expressed in both embryonic and developing Drosophila tissue. Vgl has been identified in Xenopus embryonic tissue. Vgr-1 transcripts have been identified in a variety of murine tissues, including embryonic and developing brain, lung, liver, kidney and calvaria (dermal bone) tissue. In addition, both CBMP2B and CBMP3 have been identified in lung tissue. Recently, Vgr-1 transcripts also have been identified in adult murine lung, kidney, heart, and brain tissue, with particularly high levels in the lung (see infra). GDF-1 has been identified in human adult cerebellum and in fetal brain tissue. In addition, recent Northern blot analyses indicate that OP-1 is encoded by multiple transcripts in different tissues. This potential alternative splicing is consistent with the hypothesis that the longer transcripts may encoded additional proteins (e.g., bicistronic mRNA) and each form may be tissue or developmentally related.

OP-1 and the CBMP2 proteins, both first identified as bone morphogens, have been identified in mouse and human placenta, hippocampus, calvaria and osteosarcoma tissue as determined by identification of OP-1 and CMBP2-specific sequences in cDNA libraries constructed from these tissues (see U.S. Ser. No. 422,699, incorporated herein by reference). Additionally, the OP-1 protein is present in a variety of embryonic and developing tissues including kidney, liver, heart and brain as determined by Western blot analysis and immunolocalization (see infra). OP-1-specific transcripts also have been identified in both embryonic and developing tissues, most abundantly in developing kidney, bladder, adrenal and (see infra). OP-1 also has been identified as a mesoderm inducing factor present during embryogenesis. Moreover, OP-1 has been shown to be associated with satellite cells in the muscle and associated with potential pluripotential stem cells in bone marrow following damage to adult murine endochondral bone, indicating its morphogenic role in tissue repair and regeneration. In addition, a novel protein GDF-1 comprising a 7 cysteine skeleton, has been identified in neural tissue (Lee, 1991, Proc. Nat. Aca. Sci. 88: 4250–4254).

Knowledge of the tissue distribution of a given morphogen may be useful in choosing a cell type for screening according to the invention, or for targeting that cell type or tissue type for treatment. The proteins (or their mRNA transcripts) are readily identified in different tissues using standard methodologies and minor modifications thereof in tissues where expression may be low. For example, protein distribution may be determined using standard Western blot analysis or immunocytochemical techniques, and antibodies specific to the morphogen or morphogens of interest. Similarly, the distribution of morphogen transcripts may be determined using standard Northern hybridization protocols and a transcript-specific probe and hybridization conditions.

2. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens detectable according to the methods of this invention first were identified, as well as a description on how to make, use and test them for morphogenic activity are disclosed in U.S. Ser. No. 667,274, filed Mar. 11, 1991 and U.S. Ser. No. 752,764, filed Aug. 30, 1991, the disclosures of which are hereby incorporated by reference. As disclosed therein, the morphogens may be purified from naturally-sourced material or recombinantly produced from procaryotic or eucaryotic host cells, using the genetic sequences disclosed therein. Alternatively, novel morphogenic sequences may be identified following the procedures disclosed therein.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens detectable according to the methods and compositions of this invention also may be described by morphogenically active proteins having amino acid sequences sharing 70% or, preferably, 80% homology (similarity) with any of the sequences described above, where "homology" is as defined herein above.

The morphogens detectable according to the method of this invention also can be described by any of the 6 generic sequences described herein (Generic Sequences 1, 2, 3, 4, 5 and 6). Generic sequences 1 and 2 also may include, at their N-terminus, the sequence Cys Xaa Xaa Xaa Xaa      (Seq. ID No. 15)
1             5

Table II, set forth below, compares the amino acid sequences of the active regions of native proteins that have been identified as morphogens, including human OP-1 (hOP-1, Seq. ID Nos. 5 and 16–17), mouse OP-1 (mOP-Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), with CBMP-2A then comprising Lys and Ile, whereas CBMP-2B comprises Ser and Ile.

TABLE II

| | | | | | | | | |
|---|---|---|---|---|---|---|---|---|
| hOP-1 | Cys | Lys | Lys | His | Glu | Leu | Tyr | Val |
| mOP-1 | ... | ... | ... | ... | ... | ... | ... | ... |
| hOP-2 | ... | Arg | Arg | ... | ... | ... | ... | ... |
| mOP-2 | ... | Arg | Arg | ... | ... | ... | ... | ... |
| DPP | ... | Arg | Arg | ... | Ser | ... | ... | ... |
| Vgl | ... | ... | Lys | Arg | His | ... | ... | ... |
| Vgr-1 | ... | ... | ... | ... | Gly | ... | ... | ... |
| CBMP-2A | ... | ... | Arg | ... | Pro | ... | ... | ... |
| CBMP-2B | ... | Arg | Arg | ... | Ser | ... | ... | ... |
| BMP3 | ... | Ala | Arg | Arg | Tyr | ... | Lys | ... |
| GDF-1 | ... | Arg | Ala | Arg | Arg | ... | ... | ... |
| 60A | ... | Gln | Met | Glu | Thr | ... | ... | ... |
| BMP5 | ... | ... | ... | ... | ... | ... | ... | ... |
| BMP6 | ... | Arg | ... | ... | ... | ... | ... | ... |
| | 1 | | | | 5 | | | |
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | Ser | ... | ... | ... | ... | ... | ... | Leu | ... |
| DPP | Asp | ... | Ser | ... | Val | ... | ... | Asp | ... |
| Vgl | Glu | ... | Lys | ... | Val | ... | ... | ... | Asn |
| Vgr-1 | ... | ... | Gln | ... | Val | ... | ... | ... | ... |
| CBMP-2A | Asp | ... | Ser | ... | Val | ... | ... | Asn | ... |
| CBMP-2B | Asp | ... | Ser | ... | Val | ... | ... | Asn | ... |
| BMP3 | Asp | ... | Ala | ... | Ile | ... | ... | Ser | Glu |
| GDF-1 | ... | ... | ... | Glu | Val | ... | ... | His | Arg |
| 60A | Asp | ... | Lys | ... | ... | ... | ... | His | ... |
| BMP5 | ... | ... | ... | ... | ... | ... | ... | ... | ... |
| BMP6 | ... | ... | Gln | ... | ... | ... | ... | ... | ... |
| | | | 10 | | | | 15 | | |
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | Gln | ... | ... | Ser |
| mOP-2 | ... | Val | ... | ... | ... | Gln | ... | ... | Ser |
| DPP | ... | ... | Val | ... | ... | Leu | ... | ... | Asp |
| Vgl | ... | Val | ... | ... | ... | Gln | ... | ... | Met |
| Vgr-1 | ... | ... | ... | ... | ... | Lys | ... | ... | ... |
| CBMP-2A | ... | ... | Val | ... | ... | Pro | ... | ... | His |
| CBMP-2B | ... | ... | Val | ... | ... | Pro | ... | ... | Gln |
| BMP3 | ... | ... | ... | Ser | ... | Lys | Ser | Phe | Asp |
| GDF-1 | ... | Val | ... | ... | ... | Arg | ... | Phe | Leu |
| 60A | ... | ... | ... | ... | ... | ... | ... | ... | Gly |

TABLE II-continued

| | | | 20 | | | 25 | | |
|---|---|---|---|---|---|---|---|---|
| BMP5 | ... | ... | ... | ... | ... | ... | ... | ... |
| BMP6 | ... | ... | ... | ... | ... | Lys | ... | ... |
| hOP-1 | Ala | Tyr | Tyr | Cys | Glu | Gly | Glu | Cys | Ala |
| mOP-1 | ... | ... | ... | ... | ... | ... | ... | ... | ... |
| hOP-2 | ... | ... | ... | ... | ... | ... | ... | ... | Ser |
| mOP-2 | ... | ... | ... | ... | ... | ... | ... | ... | ... |
| DPP | ... | ... | ... | ... | His | ... | Lys | ... | Pro |
| Vgl | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| BMP3 | ... | ... | ... | ... | Ser | ... | Ala | ... | Gln |
| GDF-1 | ... | Asn | ... | ... | Gln | ... | Gln | ... | ... |
| 60A | ... | Phe | ... | ... | Ser | ... | ... | ... | Asn |
| BMP5 | ... | Phe | ... | ... | Asp | ... | ... | ... | Ser |
| BMP6 | ... | Asn | ... | ... | Asp | ... | ... | ... | Ser |

| | | | | 30 | | | | 35 |
|---|---|---|---|---|---|---|---|---|
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vgl | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |
| BMP3 | ... | ... | Met | Pro | Lys | Ser | Leu | Lys | Pro |
| 60A | ... | ... | ... | ... | Ala | His | ... | ... | ... |
| BMP5 | ... | ... | ... | ... | Ala | His | Met | ... | ... |
| BMP6 | ... | ... | ... | ... | Ala | His | Met | ... | ... |

| | | | | | 40 | | | |
|---|---|---|---|---|---|---|---|---|
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |
| DPP | ... | ... | ... | ... | Val | ... | ... | ... | ... |
| Vgl | Ser | ... | ... | ... | ... | Leu | ... | ... | ... |
| Vgr-1 | ... | ... | ... | ... | ... | ... | ... | ... | ... |
| CBMP-2A | ... | ... | ... | ... | ... | ... | ... | ... | ... |
| CBMP-2B | ... | ... | ... | ... | ... | ... | ... | ... | ... |
| BMP3 | Ser | ... | ... | ... | Thr | Ile | ... | Ser | Ile |
| GDF-1 | Leu | ... | ... | ... | Val | Leu | Arg | Ala | ... |
| 60A | ... | ... | ... | ... | ... | ... | ... | ... | ... |
| BMP5 | ... | ... | ... | ... | ... | ... | ... | ... | ... |
| BMP6 | ... | ... | ... | ... | ... | ... | ... | ... | ... |

| | 45 | | | | | 50 | | | |
|---|---|---|---|---|---|---|---|---|---|
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |
| mOP-2 | ... | His | Leu | Met | Lys | ... | Asp | Val | ... |
| DPP | ... | Asn | Asn | Asn | ... | ... | Gly | Lys | ... |
| Vgl | ... | ... | Ser | ... | Glu | ... | ... | Asp | Ile |
| Vgr-1 | ... | ... | Val | Met | ... | ... | ... | Tyr | ... |
| CBMP-2A | ... | Asn | Ser | Val | ... | Ser | --- | Lys | Ile |
| CBMP-2B | ... | Asn | Ser | Val | ... | Ser | --- | Ser | Ile |
| BMP3 | ... | Arg | Ala** | Gly | Val | Val | Pro | Gly | Ile |
| GDF-1 | Met | ... | Ala | Ala | Ala | ... | Gly | Ala | Ala |
| 60A | ... | ... | Leu | Leu | Glu | ... | Lys | Lys | ... |
| BMP5 | ... | ... | Leu | Met | Phe | ... | Asp | His | ... |
| BMP6 | ... | ... | Leu | Met | ... | ... | ... | Tyr | ... |

| | | 55 | | | | 60 | | |
|---|---|---|---|---|---|---|---|---|
| hOP-1 | Pro | Lys | Pro | Cys | Cys | Ala | Pro | Thr | Gln |
| mOP-1 | ... | ... | ... | ... | ... | ... | ... | ... | ... |
| hOP-2 | ... | ... | Ala | ... | ... | ... | ... | ... | Lys |
| mOP-2 | ... | ... | Ala | ... | ... | ... | ... | ... | Lys |
| DPP | ... | ... | Ala | ... | ... | Val | ... | ... | ... |
| Vgl | ... | Leu | ... | ... | ... | Val | ... | ... | Lys |
| Vgr-1 | ... | ... | ... | ... | ... | ... | ... | ... | Lys |
| CBMP-2A | ... | ... | Ala | ... | ... | Val | ... | ... | Glu |
| CBMP-2B | ... | ... | Ala | ... | ... | Val | ... | ... | Glu |
| BMP3 | ... | Glu | ... | ... | ... | Val | ... | Glu | Lys |
| GDF-1 | Asp | Leu | ... | ... | ... | Val | ... | Ala | Arg |
| 60A | ... | ... | ... | ... | ... | ... | ... | ... | Arg |
| BMP5 | ... | ... | ... | ... | ... | ... | ... | ... | Lys |
| BMP6 | ... | ... | ... | ... | ... | ... | ... | ... | Lys |

TABLE II-continued

|  | | | 65 | | | | | 70 | |
|---|---|---|---|---|---|---|---|---|---|
| hOP-1 | Leu | Asn | Ala | Ile | Ser | Val | Leu | Tyr | Phe |
| mOP-1 | ... | ... | ... | ... | ... | ... | ... | ... | ... |
| hOP-2 | ... | Ser | ... | Thr | ... | ... | ... | ... | Tyr |
| mOP-2 | ... | Ser | ... | Thr | ... | ... | ... | ... | Tyr |
| Vgl | Met | Ser | Pro | ... | ... | Met | ... | Phe | Tyr |
| Vgr-1 | Val | ... | ... | ... | ... | ... | ... | ... | ... |
| DPP | ... | Asp | Ser | Val | Ala | Met | ... | ... | Leu |
| CBMP-2A | ... | Ser | ... | ... | ... | Met | ... | ... | Leu |
| CBMP-2B | ... | Ser | ... | ... | ... | Met | ... | ... | Leu |
| BMP3 | Met | Ser | Ser | Leu | ... | Ile | ... | Phe | Tyr |
| GDF-1 | ... | Ser | Pro | ... | ... | ... | ... | Phe | ... |
| 60A | ... | Gly | ... | Leu | Pro | ... | ... | ... | His |
| BMP5 | ... | ... | ... | ... | ... | ... | ... | ... | ... |
| BMP6 | ... | ... | ... | ... | ... | ... | ... | ... | ... |
|  | | | 75 | | | | | 80 | |
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Ser | ... | Asn | ... | ... | ... | ... | Arg |
| mOP-2 | ... | Ser | ... | Asn | ... | ... | ... | ... | Arg |
| DPP | Asn | ... | Gln | ... | Thr | ... | Val | ... | ... |
| Vgl | ... | Asn | Asn | Asp | ... | ... | Val | ... | Arg |
| Vgr-1 | ... | ... | Asn | ... | ... | ... | ... | ... | ... |
| CBMP-2A | ... | Glu | Asn | Glu | Lys | ... | ... | ... | ... |
| CBMP-2B | ... | Glu | Tyr | Asp | Lys | ... | Val | ... | ... |
| BMP3 | ... | Glu | Asn | Lys | ... | ... | Val | ... | ... |
| GDF-1 | ... | Asn | ... | Asp | ... | ... | Val | ... | Arg |
| 60A | Leu | Asn | Asp | Glu | ... | ... | Asn | ... | ... |
| BMP5 | ... | ... | ... | ... | ... | ... | ... | ... | ... |
| BMP6 | ... | ... | Asn | ... | ... | ... | ... | ... | ... |
|  | | | | | 85 | | | | |
| hOP-1 | Lys | Tyr | Arg | Asn | Met | Val | Val | Arg | |
| mOP-1 | ... | ... | ... | ... | ... | ... | ... | ... | |
| hOP-2 | ... | His | ... | ... | ... | ... | ... | Lys | |
| mOP-2 | ... | His | ... | ... | ... | ... | ... | Lys | |
| DPP | Asn | ... | Gln | Glu | ... | Thr | ... | Val | |
| Vgl | His | ... | Glu | ... | ... | Ala | ... | Asp | |
| Vgr-1 | ... | ... | ... | ... | ... | ... | ... | ... | |
| CBMP-2A | Asn | ... | Gln | Asp | ... | ... | ... | Glu | |
| CBMP-2B | Asn | ... | Gln | Glu | ... | ... | ... | Glu | |
| BMP3 | Val | ... | Pro | ... | ... | Thr | ... | Glu | |
| GDF-1 | Gln | ... | Glu | Asp | ... | ... | ... | Asp | |
| 60A | ... | ... | ... | ... | ... | Ile | ... | Lys | |
| BMP5 | ... | ... | ... | ... | ... | ... | ... | ... | |
| BMP6 | ... | ... | ... | Trp | ... | ... | ... | ... | |
|  | 90 | | | | 95 | | | | |
| hOP-1 | Ala | Cys | Gly | Cys | His | | | | |
| mOP-1 | ... | ... | ... | ... | ... | | | | |
| hOP-2 | ... | ... | ... | ... | ... | | | | |
| mOP-2 | ... | ... | ... | ... | ... | | | | |
| DPP | Gly | ... | ... | ... | Arg | | | | |
| Vgl | Glu | ... | ... | ... | Arg | | | | |
| Vgr-1 | ... | ... | ... | ... | ... | | | | |
| CBMP-2A | Gly | ... | ... | ... | Arg | | | | |
| CBMP-2B | Gly | ... | ... | ... | Arg | | | | |
| BMP3 | Ser | ... | Ala | ... | Arg | | | | |
| GDF-1 | Glu | ... | ... | ... | Arg | | | | |
| 60A | Ser | ... | ... | ... | ... | | | | |
| BMP5 | Ser | ... | ... | ... | ... | | | | |
| BMP6 | ... | ... | ... | ... | ... | | | | |
|  | | | 100 | | | | | | |

**Between residues 56 and 57 of BMP3 is a Val residue; between residues 43 and 44 of GDF-1 lies the amino acid sequence Gly—Gly—Pro—Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayoff, et al., *Atlas of Protein Sequence and Structure* vol. 5, supp. 3, pp.345–362, (M. O. Dayoff, ed., Nat'l BioMed. Res. Fd'n, Washington D.C. 1979.)

The currently most preferred protein sequences detectable as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes detection of morphogens comprising species of polypeptide chains having the generic amino acid sequence referred to herein as "OPX", which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

3. Tissue-Specific Expression of OP-1

Once a morphogen is identified in a tissue, its level may be determined either at the protein or nucleic acid level. By comparing the levels of production of a given morphogen among different tissues, it is possible to determine the tissue(s) of origin of that morphogen. The level of production of the morphogen OP-1 in different tissues is one example of a morphogen having a tissue of origin, i.e., the kidney, which contains a cell type that can also be used as the cell type which is used to screen, according to the invention, different compounds for their potential effects on morphogen (OP-1) production.

The level of OP-1 varies among different tissue types. In order to screen compounds for their effect on the production of OP-1 by a given cell type, it may be desirable to determine which tissues produce levels of OP-1 which are sufficiently high to show a potential decrease and sufficiently low to show a potential increase in production. Different tissues may be screened at the RNA level as follows.

Any probe capable of hybridizing specifically to a transcript, and distinguishing the transcript of interest from other, related transcripts may be used. Because the morphogens to be detected in the methods of this invention share such high sequence homology in their C-terminal domain, the tissue distribution of a specific morphogen transcript may best be determined using a probe specific for the "pro" region of the immature protein and/or the N-terminal heterogeneous region of the mature protein. Another useful probe sequence is the 3' non-coding region immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the pro region and the N-terminus of the mature sequence. Similarly, particularly useful mOP-1-specific probe sequences are the BstXI-BglI fragment, a 0.68 kb sequence that covers approximately two-thirds of the mOP1 pro region; a StuI-StuI fragment, a 0.2 kb sequence immediately upstream of the 7-cysteine domain, and an EarI-PstI fragment, a 0.3 kb fragment containing the 3' untranslated sequence. Similar approaches may be used, for example, with hOP-1 (SEQ. ID NO. 16) or human or mouse OP-2 (SEQ. ID NOS. 20 and 22).

Using morphogen-specific oligonucleotides probes, morphogen transcripts can be identified in mammalian tissues, using standard methodologies well known to those having ordinary skill in the art. Briefly, total RNA from mouse embryos and organs from post-natal animals is prepared using the acid guanidine thiocyanate-phenolchloroform method (Chomczynski et al., Anal. Biochem. 162:156–159, 1987). The RNA may be dissolved in TES buffer (10 mM Tris-HCl, 1 mM EDTA, 0.1% SDS, pH 7.5) and treated with Proteinase K (approx. 1.5 mg per g tissue sample) at 45° C. for 1 hr. Poly(A)$^+$ RNA selection on oligo(dT)-cellulose (Type 7, Pharmacia LKB Biotechnology Inc., Piscataway, N.J.) may be done in a batch procedure by mixing 0.1 g oligo(dT)-cellulose with 11 ml RNA solution (from 1 g tissue) in TES buffer and 0.5M NaCl). Thereafter the oligo (dT) cellulose is washed in binding buffer (0.5M NaCl, 10 mM Tris-HCl, 1 mM EDTA, pH 7.5) and poly(A)$^+$ RNA is eluted with water. Poly(A)$^+$ RNA (5 or 15 µg/lane) is fractionated on 1 or 1.2% agarose-formaldehyde gels (Selden, in Current Protocols in Molecular Biology, Ausubel et al. eds., pp. 1–4, 8, 9, Greene Publishing and Wiley-Interscience, New York, 1991). 1 µl of 400 µg/ml ethidium bromide is added to each sample prior to heat denaturation (Rosen et al., Focus 12:23–24, 1990). Following electrophoresis, the gels are photographed and the RNA is blotted overnight onto Nytran nitrocellulose membranes (Schleicher & Schuell Inc., Keene, N.H.) with 10×SSC. The membranes are baked at 80° C. for 30–60 min. and irradiated with UV light (1 mW/cm$^2$ for 25 sec.). The Northern hybridization conditions may be as previously described (Ozkaynak et al., EMBO J. 9:2085–2093, 1990). For re-use, the filters may be deprobed in 1 mM Tris-HCl, 1 mM EDTA, 0.1% SDS, pH 7.5, at 90°–95° C. and exposed to film to assure complete removal of previous hybridization signals.

One probe which may be used to screen for transcripts encoding a morphogen includes a portion of or the complete OP-1 cDNA, which may be used to detect the presence of OP-1 mRNA or mRNAs of related morphogens. The sequence of the murine cDNA gene is set forth in SEQ ID NO:14.

OP-1 mRNA expression was analyzed in 17 day mouse embryos and 3 day post-natal mice by sequentially hybridizing filters with various probes. Probes from regions other than the highly conserved 7-cysteine domain were selected because this region is highly variable among members of the TGF-β superfamily. FIG. 1 shows the fragments of OP-1, used as probes in the Northern hybridizations. The solid box indicates the putative signal peptide and the hatched box corresponds to the TGF-β-like domain that contains the seven cysteine residues. Asterisks indicate the potential N-glycosylation sites. The arrow marks the location of the cleavage site for OP-1 maturation. Three solid bars below the diagram indicate the OP-1 specific fragments used in making $^{32}$P-labeled probes (0.68 kb BstXI-BglI fragment, 0.20 kb StuI—StuI fragment and 0.34 kb EarI-PstI non-coding fragment).

Figure 2:
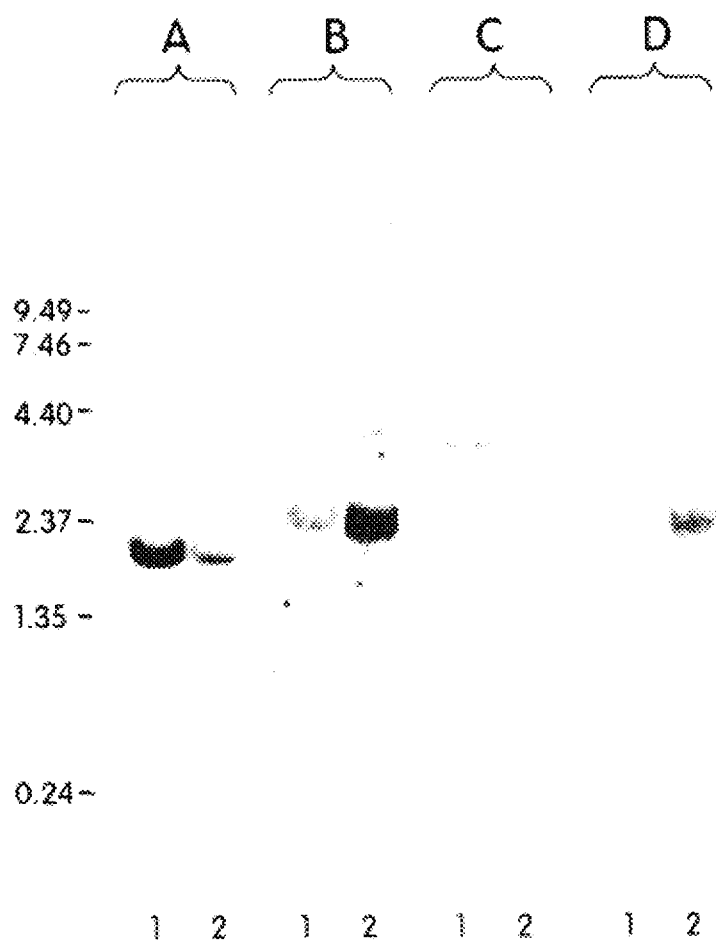
FIG. 2 shows results of Northern blot analysis of RNA using different OP-1-specific probes.
Figure 3:
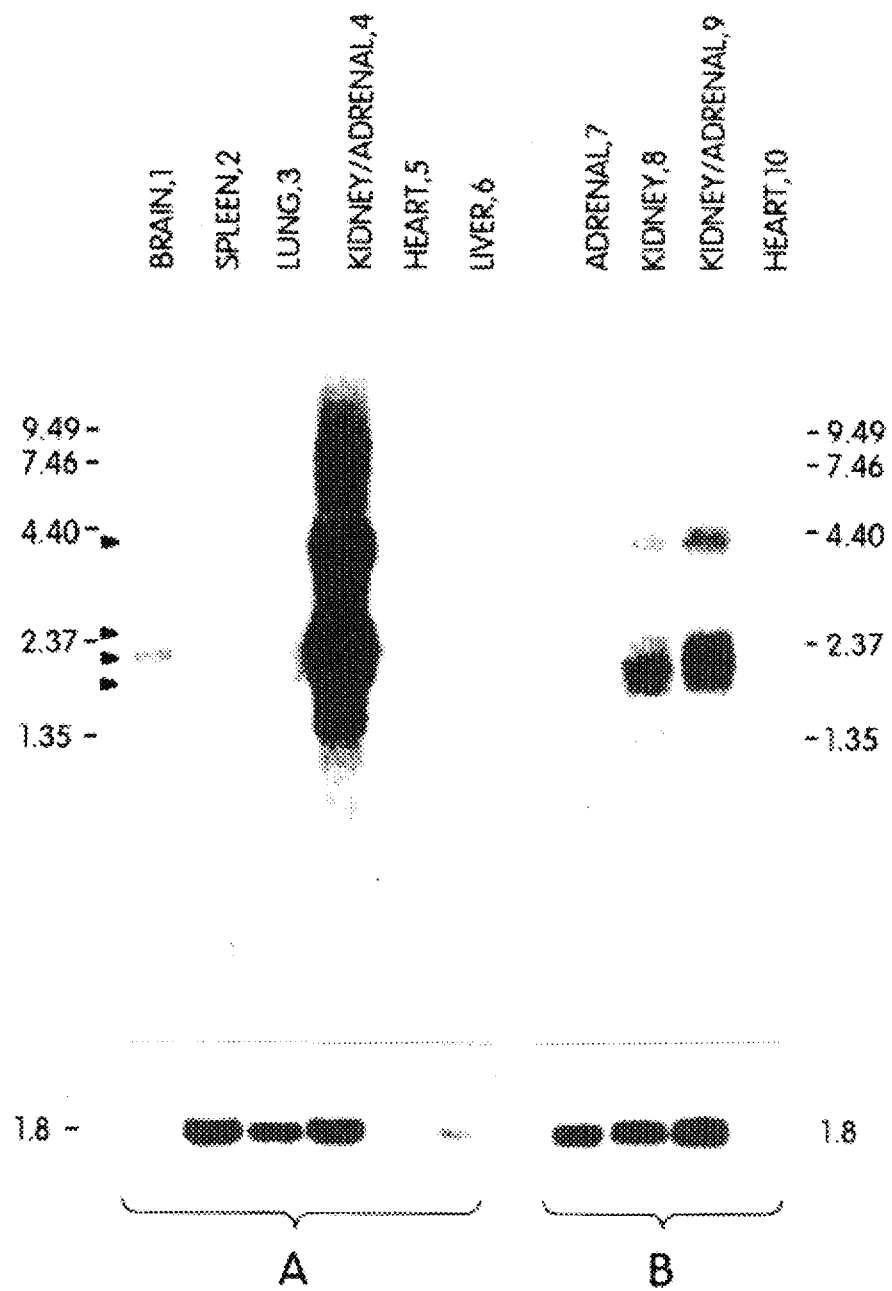
FIG. 3 shows results of Northern blot analysis of RNA from different cells types probed with an OP-1 probe.

Hybridization with a probe that covers approximately two thirds of the pro region (the 0.68 kb BstXI-BglI fragment), reveals a 4 kb message and 3 messages at 1.8 kb, 2.2 kb and 2.4 kb (FIGS. 2B and D, and FIG. 3). In the Northern hybridization of FIG. 2, equal amounts (15 µg) of poly(A)$^+$ RNA were loaded into each lane, electrophoresed on a 1% agarose-formaldehyde gel, blotted and hybridized. A 0.24–9.49 kb RNA ladder (Bethesda Research Labs, Inc.) was used as size standard. The same filter was used for sequential hybridizations with labeled probes specific for OP-1 (Panels B and D), Vgr-1 (Panel C), and EF-Tu (Panel A). Panel A: the EF-Tu specific probe (a control) was the 0.4 kb HindIII-SacI fragment (part of the coding region), the SacI site used belonged to the vector; Panel B: the OP-1 specific probe was the 0.68 kb BstXI-BglI fragment (two thirds of the pro region and upstream sequences of the mature domain, not including any sequences from the 7-cysteine domain); Panel C: the Vgr-1 specific probe was the 0.26 kb PvuII-SacI fragment (part of the pro region and the amino-terminal sequences of the mature domain, including the first cysteine) (Lyons et al., 1989, Proc. Nat. Aca. Sci. 86: 4554, hereby incorporated by reference). Panel D: the OP-1 (3' flanking) specific probe was the 0.34 kb EarI-PstI fragment (3' untranslated sequences immediately following the sequences encoding OP-1).

In FIG. 3, the tissues to be used for RNA preparation were obtained from two week old mice (Panel A) or 5 week old mice (Panel B), with the exception of poly A+ RNA which was obtained from kidney adrenal gland of two week old mice (Panel B). Equal amounts of poly A+ RNA (15 μg for Panel A and 5 μg for Panel B) were loaded into each well. After electrophoresis (1.2% agarose-formaldehyde gels) and blotting, RNA was hybridized to the OP-1 specific 3' flanking probe described in the legend of FIG. 2 (Panel D). The 0.24–9.5 kb RNA ladder was used as size standard. The arrowheads indicate the OP-1 specific messages. The lower section of Panels A and B show the hybridization pattern obtained with the EF-Tu specific probe (a control).

Although the size of the Vgr-1 specific message is close to the 4 kb OP-1 species (FIG. 2 Panel C), the OP-14 kb mRNA is somewhat larger. To further rule out cross-hybridization with a non-OP-1 message, the 0.2 kb StuI—StuI fragment which represents the gene specific sequences immediately upstream of those encoding the 7-cysteine domain was used. This probe gave a hybridization pattern similar to the one shown in FIG. 2 Panel B (data not shown). A third probe, the 0.34 kb EarI-PstI fragment containing 3' untranslated sequences, also confirmed the pattern (FIG. 2 Panel D). Thus, the same four OP-1 specific messages were observed with three distinct probes.

The appearance of a new 4 kb OP-1 mRNA species was initially interpreted as cross hybridization of the OP-1 probe with Vgr-1 mRNA, which is approximately this size (FIG. 2 Panel C). However, the 4 kb message was detected with three different OP-1 specific probes, including one specific to the 3' untranslated region, and moreover it was separated from Vgr-1 message on the basis of size. Most likely, therefore, the 4 kb mRNA (and the three species of 1.8 kb, 2.2 kb and 2.4 kb) results from alternative splicing of OP-1 transcripts. The 4 kb OP-1 mRNA could also represent a bicistronic mRNA. The 4 kb message is a minor species in kidney, while it is more prominent in adrenal tissue.

The level of OP-1 expression was compared in different tissues using poly(A)⁺ RNA prepared from brain, spleen, lung, kidney and adrenal gland, heart, and liver of 13 day post-natal mice. The RNA was analyzed on Northern blots by hybridization to various probes (FIG. 3. Equal amounts of mRNA, as judged by optical density, were fractionated on agarose formaldehyde gels. Ethidium bromide staining of the gels revealed some residual ribosomal RNA in addition to the mRNA and provided another assurance that the mRNA was not degraded and that there was not significant quantitative or qualitative variation in the preparation. As control for mRNA recovery, EF-Tu (translational elongation factor) mRNA was probed (assuming uniform expression of EF-Tu in most tissues). A great variation in the level of OP-1 expression was observed in spleen, lung, kidney and adrenal tissues whereas EF-Tu mRNA levels appeared relatively constant in these tissues (FIG. 3 Panel A). The highest level of OP-1 mRNA was found in the kidneys. Uniformly lower levels of EF-Tu mRNA were found in brain, heart and liver (FIG. 3 Panel A). Additional analysis of OP-1 mRNA showed the presence of significant amounts of OP-1 mRNA in the bladder (data not shown). In summary, next to kidney, bladder and adrenal tissue, brain tissue contained the highest levels of OP-1 RNA, whereas heart and liver did not give detectable signals.

OP-1 mRNA patterns display qualitative changes in the various tissues. Of the four messages found in brain, the 2.2 kb message is most abundant whereas in lung and spleen the 1.8 kb message predominates. Levels of the 1.8–2.4 kb in the kidney OP-1 mRNA are approximately two times higher in 3 day post-natal mice than in 17 day embryos, perhaps reflecting phases in bone and/or kidney development. mRNA was also prepared from carefully separated renal and adrenal tissues of 5 week old mice. Northern blot analysis (FIG. 4, Panel B) revealed that the high levels of 2.2 kb mRNA were derived from renal tissue whereas the 4 kb mRNA was more prominent in adrenal tissue.

The detection of of OP-1 message primarily in the kidney but also in bladder links OP-1 expression specifically with the urinary tract. Interestingly, the related Vgr-1 is also expressed at significant levels in kidney although its main site of expression in lung.

Once the tissue-specific expression of a given morphogen is known, cell types known to exist in that tissue or cell lines derived from that tissue can be screened, in a similar manner, to identify the cell type within that tissue that is actually responsible for the tissue specific synthesis and secretion of the morphogen. Once a cell type which produces the morphogen in an amount sufficient to detect increases or decreases in the production level of the morphogen upon exposure to a compound is identified, it may be used in tissue culture assay to rapidly screen for the ability of compound to upregulate or down regulate the synthesis and secretion of the morphogen. The level of morphogen production by the chosen cell type is determined with and without incubating the cell in culture with the compound, in order to assess the effects of the compound on the cell's ability to synthesize or secrete the morphogen. This can be accomplished by detection of the level of production of the morphogen either at the protein or mRNA level.

4. Growth of Cells in Culture

Cell cultures derived from kidney, adrenals, urinary bladder, brain, or other organs, may be prepared as described widely in the literature. For example, kidneys may be explanted from neonatal, new born, young or adult rodents (mouse or rat) and used in organ culture as whole or sliced (1–4 mm) tissues. Primary tissue cultures and established cell lines, also derived from kidney, adrenals, urinary, bladder, brain, or other tissues may be established in multiwell plates (6 well, 24 well, or 96 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transfertin, glucose, albumin, or other growth factors).

Samples for testing the level of morphogen production include culture supernatants or cell lysates, collected periodically and evaluated for OP-1 production by immunoblot analysis of a portion of the cell culture itself, collected periodically and used to prepare polyA+ RNA for RNA analysis (Sambrook et al., eds., Molecular Cloning, 1989, Cold Spring Harbor Press. Cold Spring Harbor, N.Y.). To monitor de novo OP-1 synthesis, some cultures are labeled with $^{35}$S-methionine/$^{35}$S-cysteine mixture for 6–24 hours and then evaluated for morphogen production by conventional immunoprecipitation methods (Sambrook et al., eds., Molecular Cloning, 1989, Cold Spring Harbor Press, Cold Spring Harbor, N.Y.). Alternatively, the production of morphogen or determination of the level of morphogen production may be ascertained using a simple assay for a parameter of cell growth, e.g., cellular proliferation or death. For example, where a morphogen is produced by a cultured cell line, the addition of antibody specific for the morphogen may result in relief from morphogen inhibition of cell growth. Thus, measurement of cellular proliferation can be used as an indication of morphogen production by a tissue.

5. Determination of Level of Morphogenic Protein

In order to quantitate the production of a morphogenic protein by a cell type, an immunoassay may be performed to detect the morphogen using a polyclonal or monoclonal antibody specific for that morphogen. For example, OP-1 may be detected using a polyclonal antibody specific for OP-1 in an ELISA, as follows.

1 µg/100 ul of affinity-purified polyclonal rabbit IgG specific for OP-1 is added to each well of a 96-well plate and incubated at 37° C. for an hour. The wells are washed four times with 0.16M sodium borate buffer with 0.15M NaCl (BSB), pH 8.2, containing 0.1% Tween 20. To minimize non-specific binding, the wells are blocked by filling completely with 1% bovine serum albumin (BSA) in BSB for 1 hour at 37° C. The wells are then washed four times with BSB containing 0.1% Tween 20. A 100 ul aliquot of an appropriate dilution of each of the test samples of cell culture supernatant is added to each well in triplicate and incubated at 37° C. for 30 min. After incubation, 100 ul biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 ul strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 ul substrate (ELISA Amplification System Kit, Life Technologies, Inc., Bethesda, Md.) are added to each well incubated at room temperature for 15 min. Then, 50 ul amplifier (from the same amplification system kit) is added and incubated for another 15 min at room temperature. The reaction is stopped by the addition of 50 ul 0.3M sulphuric acid. The OD at 490 nm of the solution in each well is recorded. To quantitate OP-1 in culture media, a OP-1 standard curve is performed in parallel with the test samples.

6. Preparation of Polyclonal Antibody

Polyclonal antibody is prepared as follows. Each rabbit is given a primary immunization of 100 ug/500 ul E. coli-produced OP-1 monomer (amino acids 328–431 of SEQ. ID NO: 11) in 0.1% SDS mixed with 500 ul Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 ug of antigen and bled (15 ml per bleed) at days seven and ten after boosting.

7. Preparation of Monoclonal Antibody and Neutralizing Monoclonal Antibody

Monoclonal antibody specific for a given morphogen may be prepared as follows. A mouse is given two injections of E. coli produced OP-1 monomer (amino acids 328–431 in SEQ ID NO:11). The first injection contains 100 ug of OP-1 in complete Freund's adjuvant and is given subcutaneously. The second injection contains 50 ug of OP-1 in incomplete adjuvant and is given intraperitoneally. The mouse then receives a total of 230 ug of OP-1 (amino acids 307–431 of SEQ ID NO:11) in four intraperitoneal injections at various times over an eight month period. One week prior to fusion, The mouse is boosted intraperitoneally with 100 ug of OP-1 (15–139) and 30 ug of the N-terminal peptide (Ser293-Asn309-Cys) conjugated through the added cys residue to bovine serum albumin with SMCC crosslinking agent. This boost is repeated five days (IP), four days (IP), three days (IP) and one day (IV) prior to fusion. The mouse spleen cells are then fused to myeloma (e.g., 653) cells at a ratio of 1:1 using PEG 1500 (Boehringer Mannheim), and the cell fusion is plated and screened for OP-1-specific antibodies using OP-1 (307–431) as antigen. The cell fusion and monoclonal screening are according to procedures widely available in the art. The neutralizing monoclonal is identified by its ability to block the biological activity of OP-1 when added to a cellular assay which responds biologically to added OP-1.

8. Identification of OP-1 Producing Cell Line Which Displays OP-1 Surface Receptors During the process of routinely testing the effects of increasing concentrations of OP-1 and TGF-$\beta$ on the proliferation of various cell lines, a cell line was identified which, surprisingly, appears not only to synthesize and secrete OP-1, but also to display cell surface receptors to which the secreted OP-1 binds and acts to inhibit proliferation of the cells. This cell line was identified after the following observations. Addition of increasing concentrations of OP-1 or TGF-$\beta$ failed to increase or decrease the relatively low basal rate of proliferation of the cells. However, addition of a monoclonal antibody, which neutralizes the activity of Op-1, resulted in a large increase in the proliferation of the cells. In addition, simultaneous addition of the same quantity of OP-1 neutralizing monoclonal to a fixed amount of OP-1 resulted in an increase in proliferation which was intermediate between the low basal level observed with OP-1 alone and the high level observed with the monoclonal alone. This cell line, which is an epithelial cell line that was derived from a bladder cell carcinoma, may be used in an assay of the invention. The parameter to be tested according to the invention is cellular proliferation. Thus, a compound(s) that increases or decreases the level of OP-1 production may be tested on this cell line as follows.

9. Assay for Identifying Drugs which Affect OP-1 Synthesis

A simple medium flux screening assay can be configured in a standard 24 or 96 well microtiter dishe, in which each well contains a constant number of a cell line having the characteristics described above. Increasing concentrations of an OP-1 neutralizing monoclonal antibody is added from left to right across the dish. A constant amount of different test substances is added from top to bottom on the dish. An increase in the synthesis and secretion of OP-1 (over its constitutive (non-induced) level) will be indicated by an increase in the amount of OP-1 neutralizing antibody required to release the cells from the antimitogenic activity of OP-1. A decrease in the synthesis and secretion of OP-1 (below its constitutive (repressed) level) will be indicated by the observation that decreased concentrations of the OP-1 neutralizing monoclonal antibody will be required to release the cells from the antimitogenic activity of OP-1. One of the major advantages of this assay is that the end point, i.e., the dilution of antibody which has an effect on cell proliferation, is a measure of mitosis, or an increase in the number of cells per well. Because several convenient and rapid assays exist for quantitating cell numbers, this assay is faster and requires significantly fewer steps to perform.

The assay may be performed as follows. After addition of appropriate concentrations of the OP-1 neutralizing monoclonal antibody and test substances to the wells containing the cells, the dishes are placed in an incubator at 37° C. for a period of 1–3 days. After completion of incubation/growth period, the dishes are removed and the cells in the individual wells are washed and stained with a vital stain, such as crystal violet. Washing and staining procedures are well-known in the art. The cells are then lysed and the stain dissolved in a constant amount of a solvent, such as ethanol. quantitations of the dissolved stain, which is readily performed on an automated plate vendor, allows for direct quantitation of the number of cells in each well.

The above-described assay has the advantages of being rapid and easy to perform because it requires few steps. Another advantage is intrinsic to the assay; drugs which are screened according to this procedure that result in cell death (i.e., cytotoxic substances) are immediately, identifiable without the need of operator observation. In addition, although drugs that stop the growth of the cells (i.e., cytostatic substances) are scored as positive due to failure to see increases in cell numbers, they are automatically scored as suspect due to the failure of the highest concentrations of OP-1 neutralizing monoclonal antibody to release the cells from the antimitogenic activity of OP-1.

10. Candidate Drugs to Screen

The screening methods of the invention is used to test compounds for their effect on the production of morphogenic protein by a given cell type. Examples of compounds which may be screened include but are not limited to chemicals, biological response modifiers (e.g., lymphokines, cytokines, hormones, or vitamins), plant extracts, microbial broths and extracts medium conditioned by eukaryotic cells, body fluids, or tissue extracts.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of diagnosing renal tissue damage or disease comprising the step of measuring endogenous expression of OP-1 by renal tissue of a mammal, wherein a depression of said endogenous expression relative to undamaged or undiseased mammalian renal tissue indicates a diagnosis that said mammal is afflicted with said damage or disease.

2. The method of claim 1 wherein said endogenous expression is measured by detecting OP-1 mRNA in renal tissue of said mammal.

3. The method of claim 1 wherein said endogenous expression is measured by detecting OP-1 protein produced by renal tissue of said mammal.

4. The method of claim 3 wherein said endogenous expression is measured by detecting OP-1 protein circulating in said mammal.

5. The method of claim 4 wherein said endogenous expression is measured using an antibody specific for said OP-1 protein.

6. The method of claim 1 wherein a depression of said endogenous expression relative to undamaged or undiseased mammalian renal tissue indicates that said mammal is afflicted with renal tissue degeneration.

7. The method of claim 6 wherein a depression of said endogenous expression relative to undamaged or undiseased mammalian renal tissue indicates that said mammal is afflicted with kidney disease.

8. The method of claim 1 wherein said mammal is human.

9. A method of diagnosing renal tissue damage or disease comprising the steps of:
(a) contacting a sample of mammalian renal tissue with an agent for specifically detecting endogenous expression of OP-1 in said tissue;
(b) detecting whether OP-1 is expressed endogenously in said tissue; and
(c) diagnosing said damage or disease if said expression is absent.

10. A method of diagnosing renal tissue damage or disease comprising the steps of:
(a) contacting a sample of mammalian renal tissue with an agent for specifically detecting endogenous expression of OP-1 in said tissue;
(b) detecting a level of endogenous expression of OP-1 in said tissue; and
(c) comparing said level of endogenously expressed OP-1 in said tissue with a reference level of OP-1 endogenously expressed in undamaged or undiseased mammalian renal tissue to diagnose said damage or disease.

11. The method of claim 9 or 10 wherein said agent is a nucleic acid probe that hybridizes specifically with RNA transcribed from an OP-1 gene present in cells of said tissue.

12. The method of claim 11 wherein said probe hybridizes specifically with RNA encoding an OP-1 polypeptide.

13. The method of claim 12 wherein said probe hybridizes specifically with RNA encoding a nonconserved fragment of said OP-1 polypeptide.

14. The method of claim 13 wherein said fragment is located N-terminal to a conserved C-terminal seven-cysteine domain of a mature OP-1 polypeptide.

15. The method of claim 13 wherein said fragment is located in the prodomain of said OP-1 polypeptide.

16. The method of claim 11 wherein said probe hybridizes specifically with RNA transcribed from a 3' noncoding region immediately following the stop codon of said OP-1 gene.

17. The method of claim 11 comprising the additional step of extracting poly(A)+RNA from said sample, said agent being contacted in step (a) with said poly(A)+RNA.

18. The method of claim 17 comprising the further additional step of blotting said poly(A)+RNA onto a nitrocellulose membrane.

19. The method of claim 18 comprising the still further additional step of electrophoretically fractionating said poly (A)+RNA prior to said step of blotting.

20. The method of claim 19 wherein said nucleic acid probe hybridizes specifically with a 4.0, 2.4, 2.2 or 1.8 kb RNA transcript of said OP-1 gene.

21. The method of claim 11 comprising the additional steps of:
(a) contacting a sample of said mammalian renal tissue with a control nucleic acid probe that hybridizes specifically with RNA transcribed from a gene expressed uniformly in mammalian tissues;
(b) detecting a level of expression of said gene in said tissue; and
(c) comparing the endogenous expression level of OP-1 with the expression level of said gene.

22. The method of claim 21 comprising the further additional step of comparing the relative expression levels of OP-1 and said gene in said tissue, with the relative expression levels of OP-1 and said gene in undamaged or undiseased mammalian renal tissue.

23. The method of claim 21 wherein said gene is transcriptional elongation factor.

24. The method of claim 9 or 10 wherein said mammalian renal tissue is human renal tissue.

25. The method of claim 24 wherein said tissue is obtained from a human afflicted with renal tissue damage.

26. The method of claim 25 wherein said human is afflicted with renal tissue degeneration.

27. The method of claim 26 wherein said human is afflicted with kidney disease.

* * * * *